(12) United States Patent
Kristie et al.

(10) Patent No.: US 8,871,789 B2
(45) Date of Patent: Oct. 28, 2014

(54) METHOD OF PREVENTING OR TREATING VIRAL INFECTION

(71) Applicant: The United States of America, as represented by the Secretary, Department of Health and Human Services, Washington, DC (US)

(72) Inventors: Thomas Michael Kristie, Silver Spring, MD (US); Yu Liang, Gaithersburg, MD (US); Jodi Vogel, Bethesda, MD (US); David J. Maloney, Point of Rocks, MD (US); Ganesha Rai Bantukallu, Arlington, VA (US); Anton Simeonov, Bethesda, MD (US); Ajit Jadhav, Chantilly, VA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/747,406

(22) Filed: Jan. 22, 2013

(65) Prior Publication Data

US 2013/0123344 A1    May 16, 2013

Related U.S. Application Data

(63) Continuation-in-part of application No. PCT/US2011/044835, filed on Jul. 21, 2011
(60) Provisional application No. 61/366,563, filed on Jul. 22, 2010.

(51) Int. Cl.
*A61K 31/47* (2006.01)
(Continued)

(52) U.S. Cl.
CPC .............. *A61K 31/551* (2013.01); *A61K 31/496* (2013.01); *A61K 31/165* (2013.01);
(Continued)

(58) Field of Classification Search
USPC ......................................... 514/311, 646, 649
See application file for complete search history.

(56) References Cited

U.S. PATENT DOCUMENTS

| 4,409,243 A | 10/1983 | Lieb |
| 2004/0198840 A1 | 10/2004 | Deloach |
| 2010/0015174 A1 | 1/2010 | Fernandez-Pol et al. |

FOREIGN PATENT DOCUMENTS

| EP | 649 656 A1 | * 10/1994 |
| JP | 10-203967 | * 8/1998 |

(Continued)

OTHER PUBLICATIONS

Rose et al, Selective Inhibitors of the JMJD2 Histone Demethylases: Combined Nondenaturing Mass Spectrometric Screening and Crystallographic Approaches, published online Jan. 2010, J. Med. Chem., 53: 1810-1818.*

(Continued)

*Primary Examiner* — Shengjun Wang
(74) *Attorney, Agent, or Firm* — Leydig, Voit & Mayer, Ltd.

(57) ABSTRACT

Disclosed are compounds and pharmaceutical compositions containing compounds that inhibit JMJD2 proteins, including those of the formula (I):

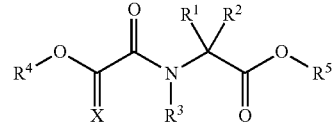

wherein $R^1$, $R^2$, $R^3$, $R^4$, and $R^5$ are as defined herein or pharmaceutically acceptable salts thereof. Also disclosed is a method of preventing or treating a viral infection of a host, comprising administering to the host an effective amount of an inhibitor of the JMJD2 family of histone demethylases, for example, a compound of the formula (I). The viral infection may be a primary infection, reactivation of a virus after latency in a host, or may be in a mammal that has undergone, is undergoing, or will undergo immunosuppressive therapy.

26 Claims, 60 Drawing Sheets

(51) Int. Cl.

| | |
|---|---|
| A61K 31/535 | (2006.01) |
| A61K 31/497 | (2006.01) |
| C07D 239/42 | (2006.01) |
| A61K 31/496 | (2006.01) |
| A61K 31/165 | (2006.01) |
| A61K 31/7088 | (2006.01) |
| A61K 31/505 | (2006.01) |
| A61K 31/44 | (2006.01) |
| A61K 45/06 | (2006.01) |
| C07D 215/14 | (2006.01) |
| A61K 31/198 | (2006.01) |
| A61K 31/166 | (2006.01) |
| A61K 31/195 | (2006.01) |
| A61K 31/135 | (2006.01) |
| A61K 31/00 | (2006.01) |
| A61K 31/225 | (2006.01) |
| A61K 31/551 | (2006.01) |
| A61K 31/137 | (2006.01) |
| A61K 31/194 | (2006.01) |
| A61K 31/506 | (2006.01) |
| A61K 31/444 | (2006.01) |
| C07C 233/56 | (2006.01) |
| A61K 31/5377 | (2006.01) |

(52) U.S. Cl.
CPC ........... *A61K 31/7088* (2013.01); *A61K 31/505* (2013.01); *A61K 31/44* (2013.01); *A61K 45/06* (2013.01); *C07D 215/14* (2013.01); *A61K 31/198* (2013.01); *A61K 31/166* (2013.01); *A61K 31/195* (2013.01); *A61K 31/135* (2013.01); *A61K 31/00* (2013.01); *A61K 31/225* (2013.01); *A61K 31/47* (2013.01); *A61K 31/137* (2013.01); *A61K 31/194* (2013.01); *A61K 31/506* (2013.01); *A61K 31/444* (2013.01); *C07C 233/56* (2013.01); *A61K 31/5377* (2013.01)
USPC ... 514/311; 514/314; 514/233.5; 514/253.06; 514/256

(56) References Cited

FOREIGN PATENT DOCUMENTS

| | | |
|---|---|---|
| JP | 2004-292399 | 10/2004 |
| WO | WO 99/40908 A1 | 8/1999 |
| WO | WO 2006/071608 A2 | 7/2006 |
| WO | WO 2006/133396 A2 | 12/2006 |
| WO | WO 2007/006581 A2 | 1/2007 |
| WO | WO 2010/011845 A2 | 1/2010 |

OTHER PUBLICATIONS

Rohde et al. "hydroxyquinolines inhibit ribonucleic acid-dependent hydroxyribonucleic acid polymerase and inactivate Rous Sarcoma Virus and Herpes Simplex Virus," Antimicrobial Agents and Chemotherapy, 1976, vol. 10, No. 2, pp. 234-240.*
JP 10-203967 machine translation.*
Baas, "Transcription prescription for herpes," *SciBX*, 2, 1-3 (2009), published online Dec. 3, 2009.
Chakraborty et al., "N-Acylanilines, Herbicide-CHA Chimera, and Amino Acid Analogues as Novel Chemical Hybridizing Agents for Wheat (*Triticum aestivum* L.)," *J. Agric. Food Chem.*, 53 (20), 7899-7907 (2005), published online Sep. 10, 2005.
Chang et al., "Histone Demethylase JMJD2A Regulates Kaposi's Sarcoma-Associated Herpesvirus Replication and is Targeted by a Viral Transcriptional Factor," *J. Virol.*, 85 (7), 3283-3293 (2011), published online Jan. 12, 2011.
Chau et al., "Cell Cycle Association of the Retinoblastoma Protein Rb and the Histone Demethylase LSD1 with the Epstein-Barr Virus Latency promoter Cp," *J. Virol.*, 82 (7), 3428-3437 (2008), published online Jan. 23, 2008.
Cole, "Chemical probes for histone-modifying enzymes," *Nat. Chem. Biol.*, 4 (10), 590-597 (2008), published online Sep. 17, 2008.
Cunliffe et al., "Novel Inhibitors of Prolyl 4-hydroxylase. 3. Inhibition by the Substrate Analogue N-Oxaloglycine and its derivatives," *J. Med. Chem.*, 35, 2652-2658 (1992).
Fauconnier, "Inhibitory action of succinic acid on the multiplication of influenza virus in embryonated eggs," *Comptes Rendus Hebdomadaires des Seances De L'Academie Des Sciences*, 239 (25), 1886-1888 (1954).
Gilmore et al., "Orthogonal Synthesis of Indolines and Isoquinolines via Aryne Annulation," *J. Am. Chem. Society*, 130 (5), 1558-1559 (2008), published online Jan. 15, 2008.
Gray et al., "Functional Characterization of JMJD2A, a Histone Deacetylase- and Retinoblastoma-binding Protein," *J. Biol. Chem.*, 280 (31), 28507-28518 (2005), published online May 31, 2005.
Hamada et al., "Design, Synthesis, Enzyme-Inhibitory Activity, and Effect on Human Cancer Cells of a Novel Series of Jumonji Domain-Containing Protein 2 Histone Demethylase Inhibitors," *J. Med. Chem.*, 53 (15), 5629-5638 (2010), published online Jul. 14, 2010.
Hamada et al., "Synthesis and activity of N-oxalylglycine and its derivatives as Jumonji C-domain-containing histone lysine demethylase inhibitors," *Bioorg. Med. Chem. Lett.*, 19 (10), 2852-2855 (2009), published online Mar. 26, 2009.
Hearn et al., "Cyclization of N-oxalyl-alpha-amino acid derivatives," Chemical Abstract No. 506665, published in 1968.
Hearn et al., "Cyclization of N-oxalyl-alpha-amino acid derivatives," *J. Org. Chem.*, 33 (10), 3980-3983 (1968).
Hörig et al., "From bench to clinic and back: Perspective on the 1st IQPC Translational Research conference," *J. Trans. Med.*, 2 (44), 1-8 (2004).
International Preliminary Report on Patentability, Application No. PCT/US2009/051557, dated Jan. 25, 2011.
International Preliminary Report on Patentability, Application No. PCT/US2011/044835, dated Jan. 22, 2013.
International Search Report, Application No. PCT/US2009/051557, dated Feb. 26, 2010.
International Search Report, Application No. PCT/US2011/044835, dated Dec. 12, 2011.
Invitation to Pay Additional Fees and, Where Applicable, Protest Fee, Application No. PCT/US2011/044835, dated Oct. 12, 2011.
King et al., "Quantitative high-throughput screening identifies 8-hydroxyquinolines as cell-active histone demethylase inhibitors," *PLoS One*, 5 (11) e15535 (2010).
Kolb et al., "Association of the cellular coactivator HCF-1 with the Golgi apparatus in sensory neurons," *J. Virol.*, 82 (19), 9555-9563 (2008), published online Jul. 30, 2008.
Kristie et al., "Control of α-herpesvirus IE gene expression by HCF-1 coupled chromatin modification activities," *Biochim. Biohpys. Acta.*, 1799 (3-4), 257-265 (2010), published online Aug. 12, 2009 (author manuscript).
Lee et al., "Histone H3 Lysine 4 Demethylation is a Target of Nonselective Antidepressive Medications," *Chem. Biol.*, 13 (6), 563-567 (2006) (with supplementary materials).
Liang et al., "Targeting the JMJD2 Histone Demethylases to Epigenetically Control Herpesvirus Infection and Reactivation from Latency," *Sci. Transl. Med.*, 5 (167ra5), 1-10 (2013) (with supplementary material).
Liang et al., "Inhibition of the histone demethylase LSD1 blocks α-herpesvirus lytic replication and reactivation from latency," *Nat. Med.*, 15 (11), 1312-1317 (2009), published online Oct. 25, 2009 (with supplementary materials).
Liang et al., "Inhibition of the histone demethylase LSD1 represses α-herpesvirus lyticreplication and reactivation from latency," Abstract International Herpesvirus Workshop (published Jul. 24, 2009).
Liang et al., "The JMJD2 family of histone demethylases cooperate with LSD1 to modulate repressive chromatin during HSV lytic infection and reactivation from latency," Abstract of Presentation at International Herpesvirus Workshop (published Jul. 20, 2010).

(56) References Cited

OTHER PUBLICATIONS

Liang et al., "The histone demethylase LSD1counters chromatin-mediated repression of infected α-herpesviruses," Abstract of Presentation at International Herpesvirus Workshop (published Jul. 19, 2008).
Lieb, "Invisible antivirals," *Int. J. Immunopharmac.*, 16 (1), 1-5 (1994).
Mecinović et al., "2-Oxoglutarate analogue inhibitors of prolyl hydroxylase domain 2," *Bioorganic & Med. Chem. Letters*, 19 (21), 6192-6195 (2009), published online Sep. 6, 2009.
Metzger et al., "LSD1 demethylates repressive histone marks to promote androgen-receptor-dependent transcription," *Nature*, 437 (7057), 436-439 (2005), published online Aug. 3, 2005 (with supplementary materials).
Mimasu et al., "Structurally Designed *trans*-2-Phenylcyclopropylamine Derivative Potently Inhibit Histone Demethylase LSDI/KDM1," *Biochemistry*, 49 (30), 6494-6503 (2010), published online Jun. 22, 2010.
Narayanan et al., "The coactivator host cell factor-1 mediates Set1 and MLL1 H3K4 trimethylation at herpesvirus immediate early promoters for initiation of infection," *PNAS*, 104 (26), 10835-10840 (2007), published online Jun. 19, 2007 (with supplementary materials).
New York Times, "Herpes Simplex In-Depth Report," http://health.nytimes.com/health/guides/disease/herpes-simples/print.html, 1-8 (2012).
Niaid press release—Certain Antidepressants May Inhibit Herpesvirus Infection and Reactivation (Oct. 26, 2009).
Partial International Search, Application No. PCT/US2011/044835, dated Oct. 12, 2011.
Patel et al., "Infections in solid-organ transplant recipients," *Clin. Microbiol. Rev.*, 10 (1), 86-124 (1997).
Presentation "The transcriptional coactivator HCF-1 mediates chromatin modifications for initiation of alpha herpesvirus infection," 13th International Conference on Immunobiology and Prophylaxis of Human Herpesvirus Infections (Nov. 5-8, 2007).
Presentation "The transcriptional coactivator HCF-1 mediates chromatin modifications for initiation of α-herpesvirus infection," Manipulation of Nuclear Processes by DNA Viruses conference (Mar. 3, 2008).
Rose et al., "Inhibitor Scaffolds for 2-Oxoglutarate-Dependent Histone Lysine Demethylases," *J. Med. Chem.*, 51 (22), 7053-7056 (2008), published online Oct. 23, 2008 (with supplementary material).
Rose et al., "Selective Inhibitors of the JMJD2 Histone Demethylases: Combined Nondenaturing Mass Spectrometric Screening and Crystallographic Approaches," *J. Med. Chem.*, 53 (4), 1810-1818 (2010), published online Jan. 20, 2010 (with supplementary material).
Schäfer et al., "Failure in an option: learning from unsuccessful proof-of-concept trials," *Drug Discover*, 13 (21/22), 913-916 (2008), published online Jun. 17, 2008.
Schmidt et al., "*trans*-2-Phenylcyclopropylamine is a mechanism-Based Inactivator of the Histone Demethylase LSD1," *Biochemistry*, 46 (14), 4408-4416 (2007), published online Mar. 17, 2007 (with supplementary materials).
Shi et al., "Histone Demethylation Mediated by the Nuclear Amine Oxidase Homolog LSD1," *Cell*, 119 (7), 941-953 (2004).
Stitt, "Infection in the Transplant Recipient," Organ Transplant 2003 Medscape, http://www.medscape.com/viewarticle/45 1788_7 (2003).
Turk et al., "Antiretroviral activity and cytotoxicity of novel zidovudine (AZT) derivatives and the relation to their chemical structure," *Int. J. Antimicrob. Agents*, 20 (4), 282-288 (2002).
UCSF Medical Center, "AIDS Treatment," http://www.ucsfhealth.org/conditions/aids/treatment.html, 1-2 (2012).
Vogel et al., "An HCF-1 protein complex couples Set1/MLL1 histone methyl-transferases with the histone demethylase LSD1," Abstract of Presentation at International Herpesvirus Workshop (published Jul. 19, 2008).
Vogel et al., "HCF-1 mediated chromatin modulation during a-herpesvirus lytic infection and reactivation from latency," Abstract of Presentation at International Herpesvirus Workshop (published Jul. 22, 2011).
Whetstine et al., "Reversal of Histone Lysine Trimethylation by the JMJD2 Family of Histone Demethylases," *Cell*, 125 (3), 467-481 (2006), published online Apr. 6, 2006.
Whitlow et al., "Association of the transcriptional coactivator HCF-1 with immediate early gene promoters during initiation of HSV-1 reactivation from latency," Abstract International Herpesvirus Workshop (published Jul. 24, 2009).
Whitlow et al., "Recruitment of the Transcriptional Coactivator HCF-1 to Viral Immediate-Early Promoters during Initiation of Reactivation from Latency of Herpes Simplex Virus Type 1," *J. Virol.*, 83 (18), 9591-9595 (2009), published online Jul. 1, 2009 (with supplementary materials).
Wissman et al., "Cooperative demethylation by JMJD2C and LSD1 promotes androgen receptor-dependent gene expression," *Nat. Cell Biol.*, 9 (3), 347-353 (2007), published online Feb. 4, 2007.
Written Opinion of the International Searching Authority No. PCT/US2009/051557, dated Jan. 25, 2011.
Written Opinion of the International Searching Authority No. PCT/US2011/044835, dated Jan. 22, 2013.

* cited by examiner

Figure 2A
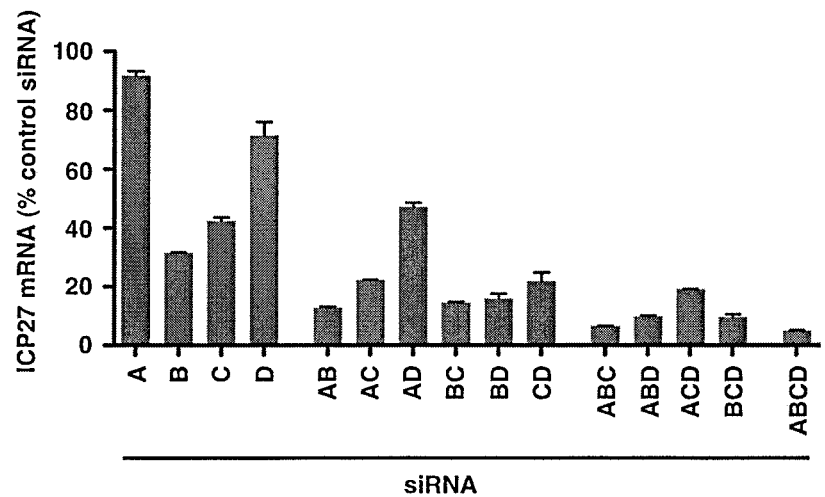
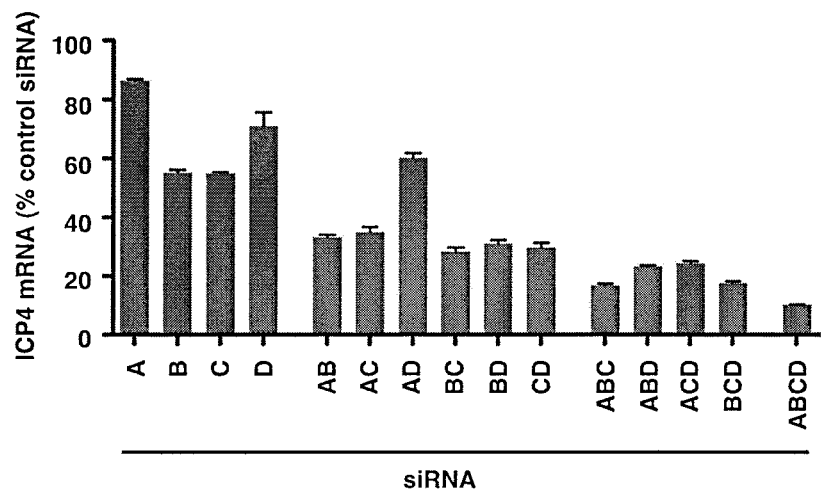
Figure 2B

SEQUENCE LISTING

```
<160> NUMBER OF SEQ ID NOS: 4

<210> SEQ ID NO 1
<211> LENGTH: 19
<212> TYPE: RNA
<213> ORGANISM: Artificial Sequence
<220> FEATURE:
<223> OTHER INFORMATION: Synthetic

<400> SEQUENCE: 1
gaaccgaccu ccaaacuuu                                              19

<210> SEQ ID NO 2
<211> LENGTH: 19
<212> TYPE: RNA
<213> ORGANISM: Artificial Sequence
<220> FEATURE:
<223> OTHER INFORMATION: Synthetic

<400> SEQUENCE: 2
gcaggcaccg uccacauuu                                              19

<210> SEQ ID NO 3
<211> LENGTH: 19
<212> TYPE: RNA
<213> ORGANISM: Artificial Sequence
<220> FEATURE:
<223> OTHER INFORMATION: Synthetic

<400> SEQUENCE: 3
gagaggacau cuacacuuu                                              19

<210> SEQ ID NO 4
<211> LENGTH: 21
<212> TYPE: RNA
<213> ORGANISM: Artificial Sequence
<220> FEATURE:
<223> OTHER INFORMATION: Synthetic

<400> SEQUENCE: 4
cuggaagaac cgcaucuaua a                                           21
```

METHOD OF PREVENTING OR TREATING VIRAL INFECTION

CROSS-REFERENCE TO RELATED APPLICATIONS

This patent application is a continuation-in-part of International Patent Application No. PCT/US2011/044835, filed Jul. 21, 2011, which claims the benefit of U.S. Provisional Patent Application No. 61/366,563, filed Jul. 22, 2010, each of which is incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,102 Byte ASCII (Text) file named "712011SequenceListing_ST25.txt" created on Jan. 22, 2013.

BACKGROUND OF THE INVENTION

Herpes viral infections, including herpes simplex virus type 1 (HSV-1) and type 2 (HSV-2) infections, are common infections worldwide. HSV-2 is the cause of most genital herpes and is generally sexually transmitted. In contrast, HSV-1 is usually transmitted via nonsexual contacts. Preexisting HSV-1 antibodies can alleviate clinical manifestations of subsequently acquired HSV-2. Furthermore, HSV-1 has become an important cause of genital herpes in some developed countries. Varicella Zoster virus characteristically produces vesicular pruritic disseminated lesions at varying degrees of maturity. It occurs most frequently in children, with prodromal malaise, pharyngitis and rhinitis, usually with fever and pruritus (chickenpox). Varicella Zoster virus may cause more severe illness in adults, where the lesions are localized and painful, and often involve the trunk (shingles). Additional manifestations of HSV viral infection may include encephalitis and keratitis. Cytomegalovirus is an additional herpesvirus which can cause considerable morbidity in infants and individuals with compromised immune systems.

Although proposals have been made for a cure for the above diseases, an unmet need continues to exist for methods of preventing or treating a viral infection of a host.

BRIEF SUMMARY OF THE INVENTION

The invention provides substances for use in preventing or treating a viral infection of a host, wherein the substance is an inhibitor of a JMJD2 protein.

For example, the invention provides a compound of the formula (I):

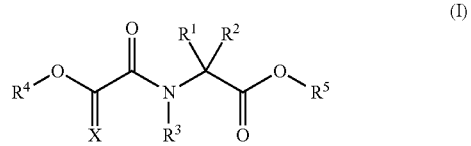

wherein $R^1$, $R^2$, $R^3$, $R^4$, and $R^5$ are as defined herein, as well as a pharmaceutical composition comprising a compound of formula (I), and a method of preventing or treating viral infection.

The invention provides a method of preventing or treating a viral infection of a host, comprising administering to the host an effective amount of an inhibitor of the JMJD2 family of histone demethylases, such as a compound described herein, wherein the administration of the inhibitor prevents or treats the viral infection.

The invention includes preventing or treating a viral infection where the viral infection is reactivation of a virus after latency in a host and/or is in a mammal that has undergone, is undergoing, or will undergo immunosuppression or immunosuppressive therapy.

The invention includes a method of inhibiting a member of the JMJD2 family of histone demethylases in a virus-infected host, comprising administering to the host an effective amount of a compound described herein.

BRIEF DESCRIPTION OF THE DRAWINGS

FIG. 2A is a bar graph, showing herpes simplex virus Immediate Early (IE) gene ICP27 mRNA levels after administration of siRNA directed against JMJD2a (A), JMJD2b (B), JMJD2c (C), JMJD2d (D), and combinations of these. FIG. 2B is a bar graph, showing herpes simplex virus Immediate Early gene ICP4 mRNA levels after administration of siRNA directed against A, B, C, and D, and combinations of these. In accordance with embodiments of the invention, the viral IE mRNA levels decrease after administration of siRNA directed against the JMJD2 family of histone demethylases.

FIG. 4 shows siRNA depletion of JMJD2 proteins results in accumulation of repressive chromatin on HSV-1 IE promoters. H3 represents total histone H3; K9me3 represents histone H3-lysine 9 trimethylation.

FIG. 8 shows DMOG inhibition of JMJD2 proteins results in accumulation of repressive chromatin on HSV-1 IE promoters. H3 represents total histone H3; K9me3 represents histone H3-lysine 9 trimethylation. DMSO is dimethyl sulfoxide.

and cellular controls (C) relative to cells transfected with control siRNAs. HeLa cells, transfected with siRNAs to JMJD2C or to the four JMJD2s, were infected with HSV-1 (0.1 PFU per cell) for 3 hours. ChIP assays used control immunoglobulin G (IgG), H3K9-me3, or histone H3 antibodies. Data are means±SEM.

Figure 31:
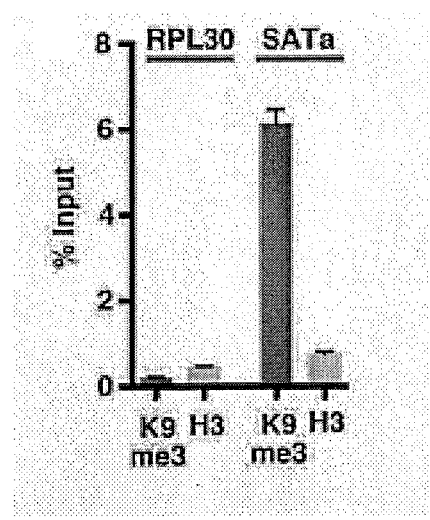

FIG. 31 is a bar graph that shows specificity of the H3K9-me3 ChIP, illustrated by a low level of H3K9-me3 associated with the active RPL30 loci and a high level associated with the repressed SATa region. Data are reflective of two independent experiments. HeLa cells, transfected with siRNAs to JMJD2C or to the four JMJD2s, were infected with HSV-1 (0.1 PFU per cell) for 3 hours. ChIP assays used control immunoglobulin G (IgG), H3K9-me3, or histone H3 antibodies. Data are means±SEM.

Figure 32:
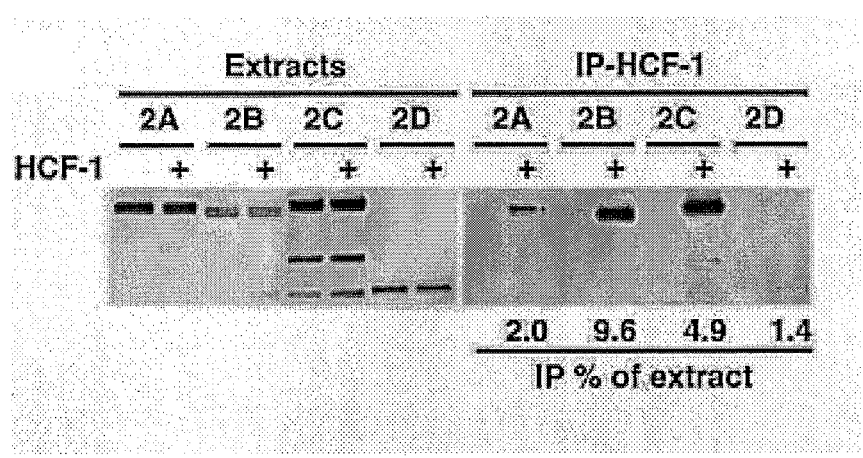

FIG. 32 shows Western blot of extracts and V5 immunoprecipitates (HCF-1) of 293F cells expressing HA-tagged JMJD2 or coexpressing HA-tagged JMJD2 and HCF-1-V5. The amounts of coimmunoprecipitated JMJD2 proteins are represented as percent of extract levels. HeLa cells, transfected with siRNAs to JMJD2C or to the four JMJD2s, were infected with HSV-1 (0.1 PFU per cell) for 3 hours. ChIP assays used control immunoglobulin G (IgG), H3K9-me3, or histone H3 antibodies. Data are means±SEM.

Figure 33:
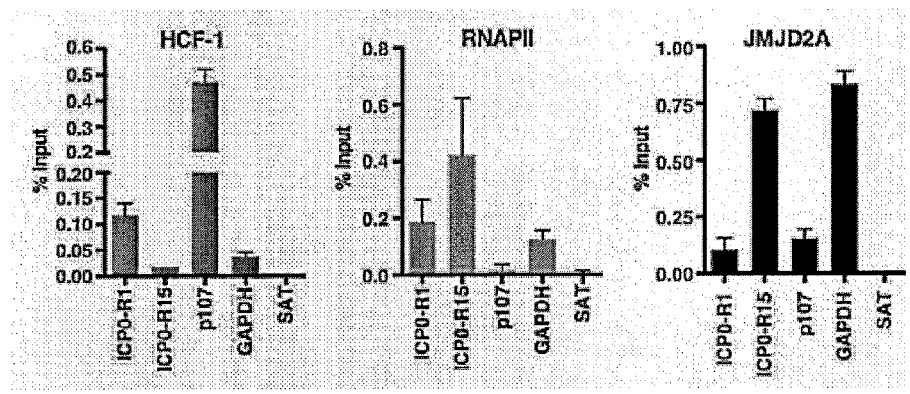
Figure 34:
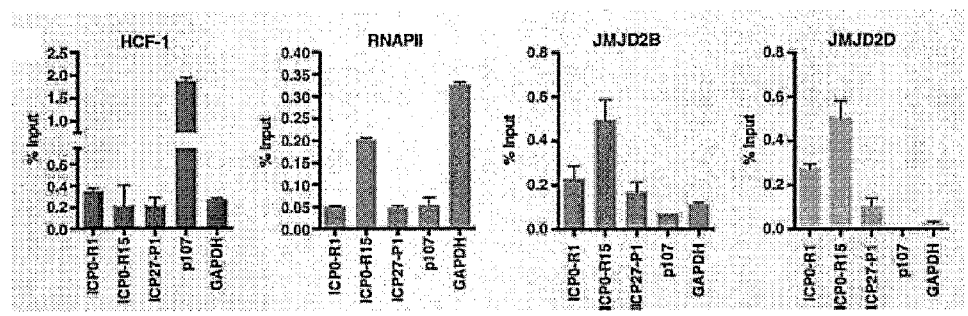

FIGS. 33 and 34 present bar graphs showing ChIP assays using antibodies to HCF-1, RNAPII, and JMJD2 proteins. Occupancy levels were determined for IE gene promoters (ICP0 and ICP27) and cellular controls (p107, GAPDH, and SATa). HeLa cells, transfected with siRNAs to JMJD2C or to the four JMJD2s, were infected with HSV-1 (0.1 PFU per cell) for 3 hours. ChIP assays used control immunoglobulin G (IgG), H3K9-me3, or histone H3 antibodies. Data are means±SEM.

Figure 35:
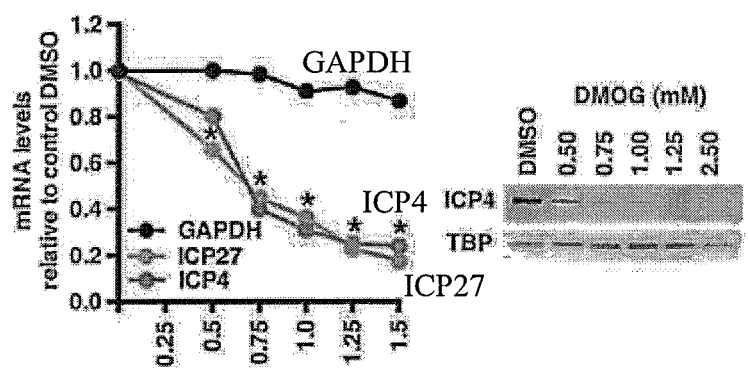

FIG. 35 shows HFF cells, treated with the indicated concentrations of the JMJD2 inhibitor DMOG for 4 hours, were infected with HSV-1 (0.1 PFU per cell). Levels of viral and cellular control mRNAs are expressed relative to cells treated with dimethyl sulfoxide (DMSO). *$P<0.0001$, two-way analysis of variance (ANOVA) with Dunnett's post hoc test. Viral IE (ICP4) and cellular (TBP) proteins were monitored by Western blot. Data are means±SEM.

Figure 36:
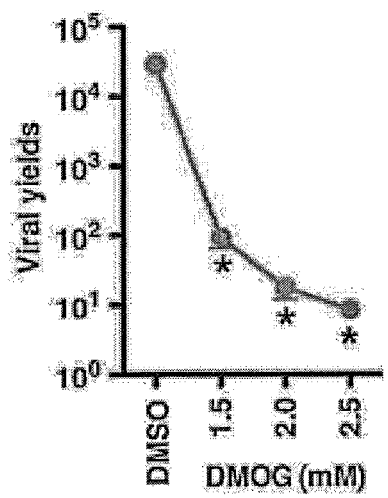

FIG. 36 shows viral yields from HFF cells infected with HSV-1 (0.1 PFU per cell) for 24 hours in the presence of DMSO or DMOG. *$P<0.0001$, one-way ANOVA with Dunnett's post hoc test. Data are means±SEM.

Figure 37:
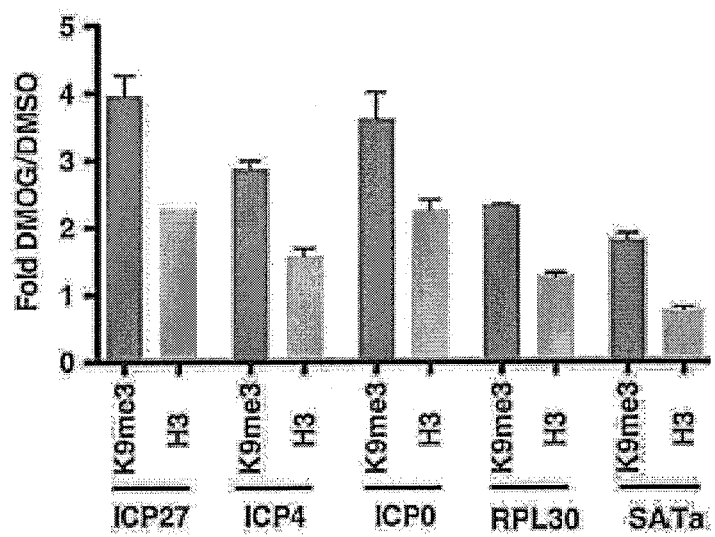

FIG. 37 shows HeLa cells treated with DMSO or 2.5 mM DMOG for 4 hours were infected with HSV-1 (0.1 PFU per cell) for 3 hours. ChIP assays were performed with IgG, H3K9-me3, or histone H3 antibodies. Levels of H3K9-me3 and histone H3 associated with IE promoters and cellular controls are expressed relative to cells treated with DMSO. The data are representative of two independent experiments. Data are means±SEM.

Figure 38:
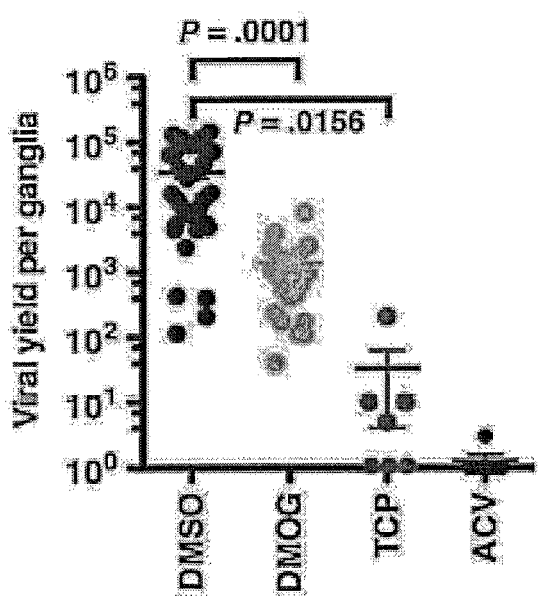

FIG. 38 shows HSV-1 latently infected trigeminal ganglia were explanted in the presence of DMSO, 2 mM DMOG, 2 mM TCP, or 100 mM acyclovir (ACV) for 2 days. Viral yields are the titer per ganglia (DMSO versus DMOG: $P=0.0001$, Wilcoxon matched-pairs signed rank test; n=20; DMSO versus TCP: $P=0.0156$; n=7). Data are means±SEM.

Figure 39:
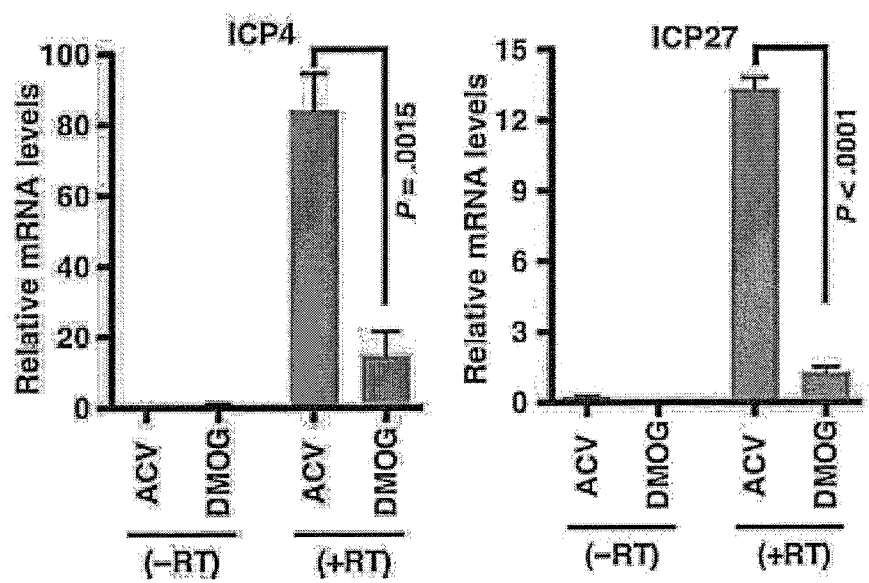
Figure 40:
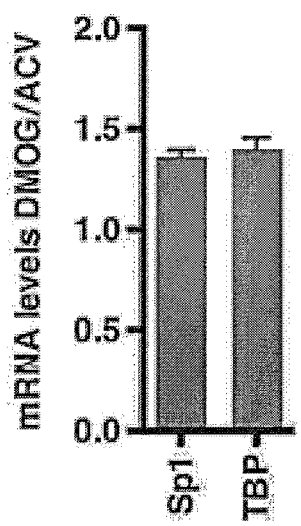
Figure 41:
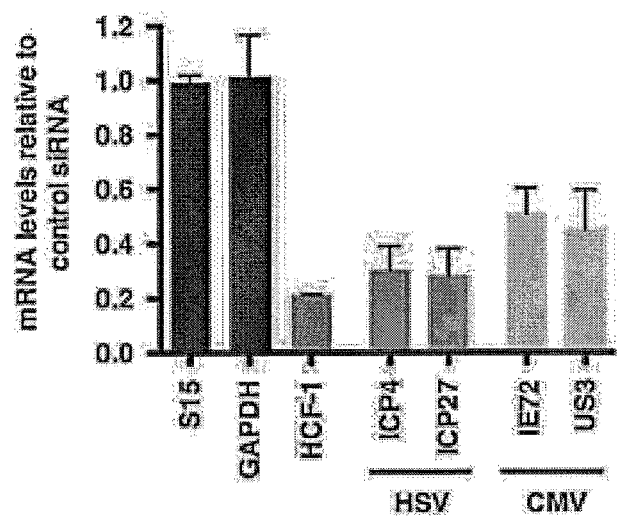
Figure 42:
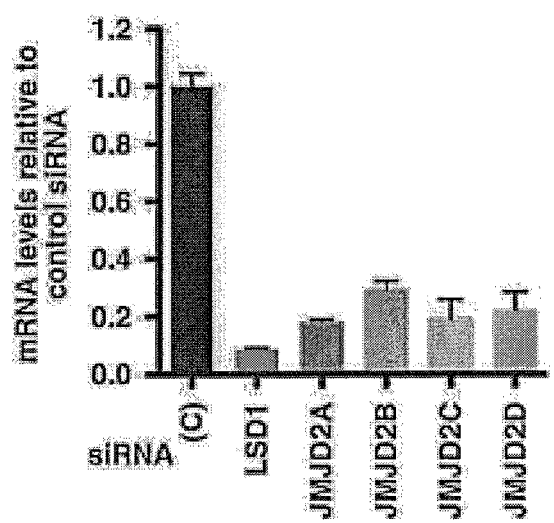
Figure 43:
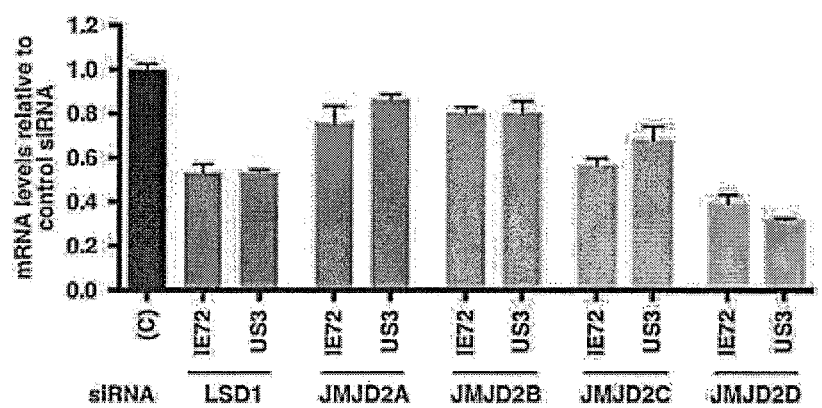
Figure 44:
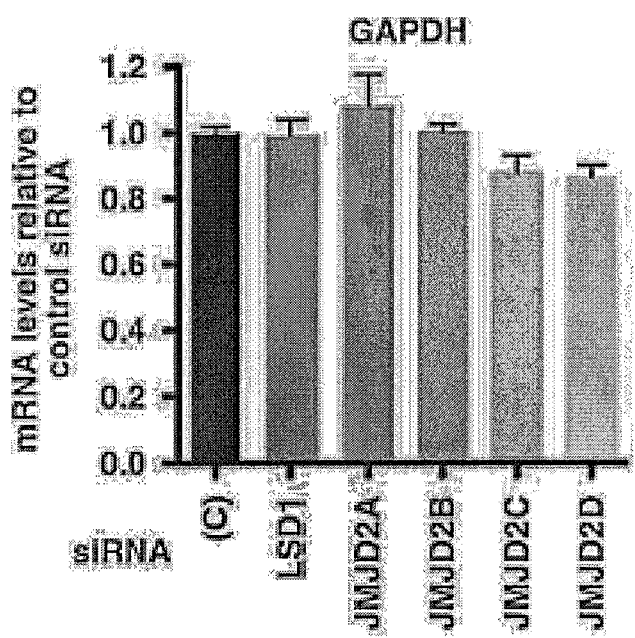

FIGS. 39 and 40 show HSV-1 latently infected trigeminal ganglia were explanted in the presence of 100 mMACV or 2 mMDMOG for 6 hours. The levels of viral IE (ICP4 and ICP27) and cellular (Sp1 and TBP) mRNAs were determined by nested reverse transcription-polymerase chain reaction (RT-PCR) or quantitative RT-PCR, respectively, and are relative to levels in 3T3 cells infected with HSV-1 [$6.5 \times 10^{-5}$ multiplicity of infection (MOIs), 4 hours] (paired two-tailed t test, P values as indicated, n=4). (—RT), control cDNA synthesis reactions without reverse transcriptase. Data are means±SEM.

FIGS. 41-44 show MRC-5 cells, transfected with control siRNA or siRNAs to HCF-1 (A), LSD1, or the JMJD2 members, were infected with HSV-1 or hCMV (0.1 PFU per cell) for 4 hours. JMJD2 and LSD1, viral IE (HSV-1 ICP4, ICP27), (hCMV IE72, US3), and control cellular mRNA levels were normalized to cellular control S15 mRNA levels and expressed as the ratios to cells transfected with control siRNA.

Figure 45:
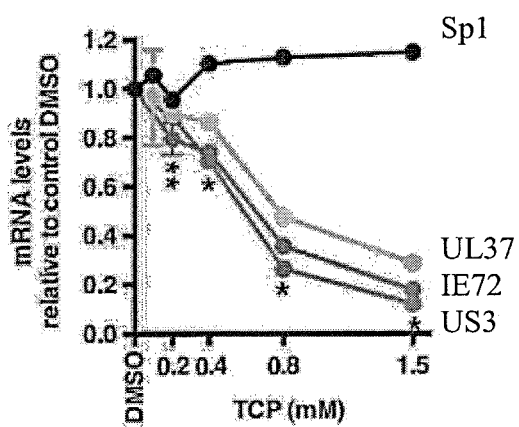
Figure 46:
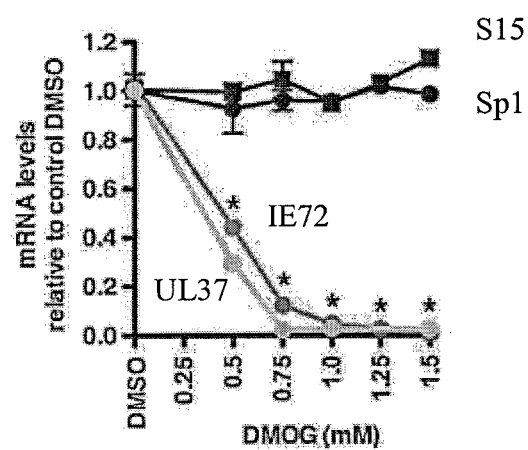

FIGS. 45 and 46 show MRC-5 cells were treated with DMSO or the indicated concentrations of LSD1 inhibitor TCP or DMOG for 3 hours, followed by infection with hCMV (0.1 PFU per cell) for 5 hours. The levels of viral IE (IE72, UL37, and US3) and control cellular (Sp1 and S15) mRNAs are expressed relative to cells treated with DMSO. *$P<0.0001$, **$P<0.002$, two-way ANOVA with Dunnett's post hoc test.

Figure 47:
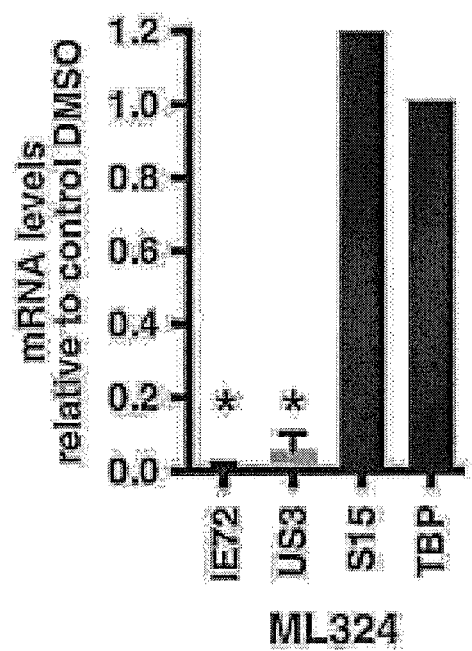

FIG. 47 shows MRC-5 cells were treated with DMSO or 50 mM ML324 for 3 hours, followed by infection with hCMV (0.1 PFU per cell) for 5 hours. mRNA levels of viral and cellular controls are expressed relative to cells treated with DMSO. Data are means±SEM. *$P<0.0001$, one-way ANOVA with Tukey's post hoc test.

Figure 48:
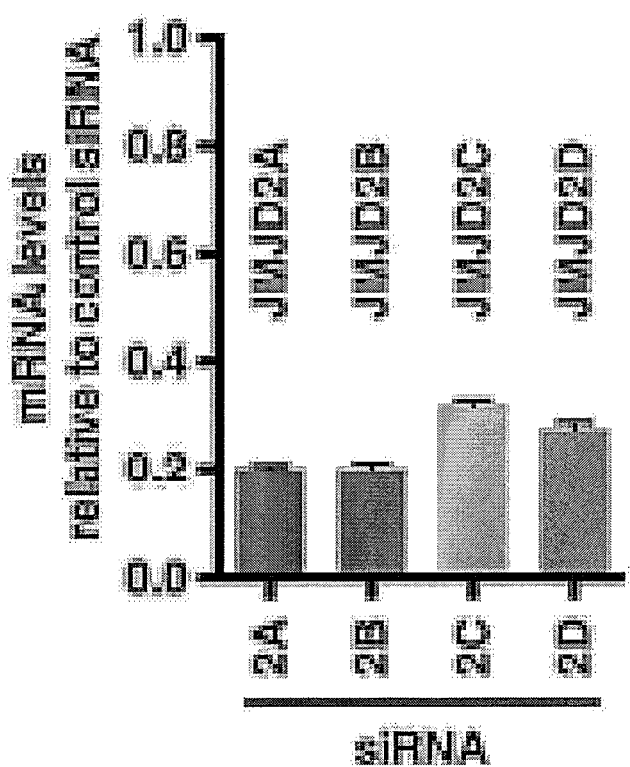
Figure 49:
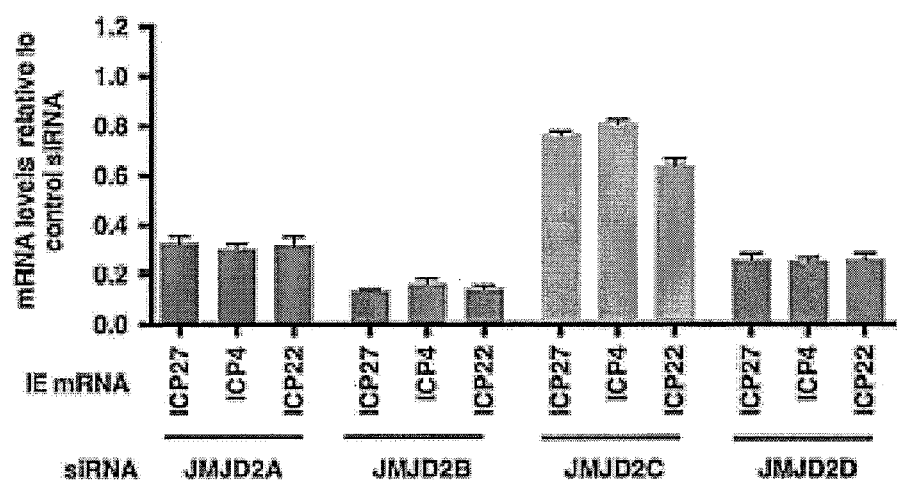
Figure 50:
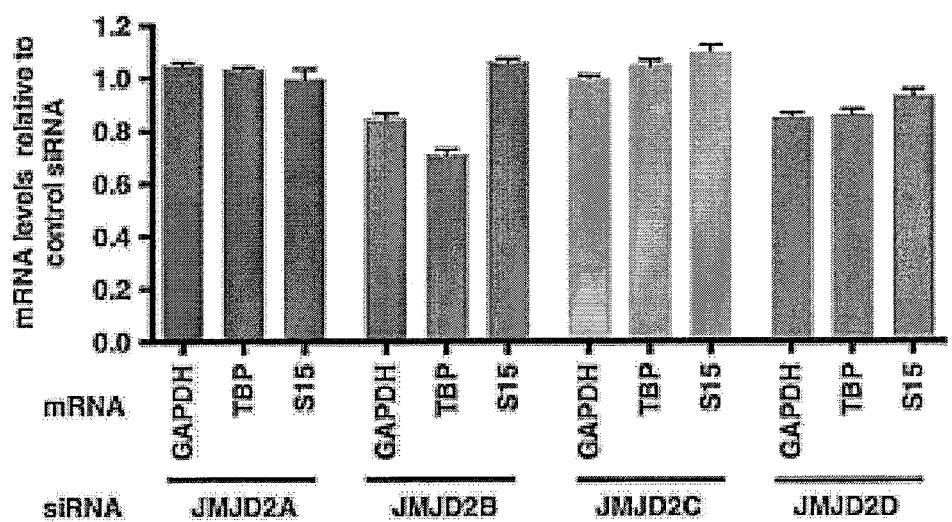
Figure 51:
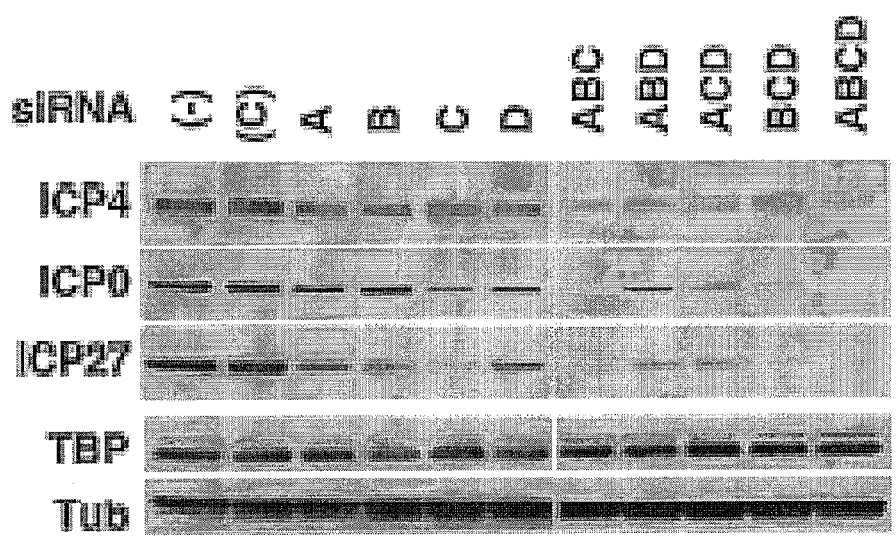

FIGS. 48-50 show MRC-5 cells were transfected with 5 nM of individual siRNA to JMJD2A, B, C, or D, followed by infection with HSV-1 (0.1 pfu/cell) for 2 h. The mRNA levels of the JMJD2 family members, HSV-1 viral IE genes (ICP 27, ICP4 ICP22), and cellular controls (GAPDH, TBP, S15) are expressed as ratios to the levels in cells transfected with control siRNA.

Figure 52:
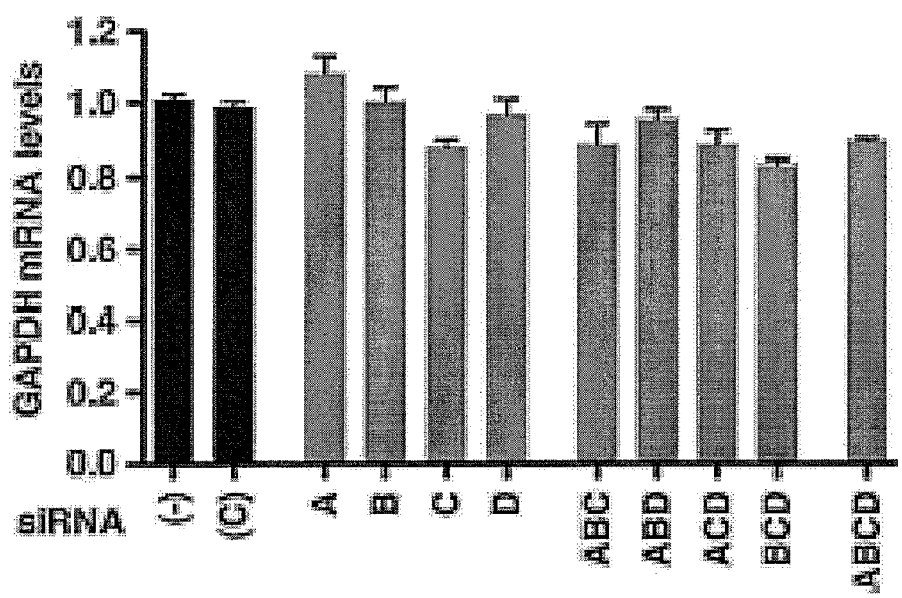
Figure 53:
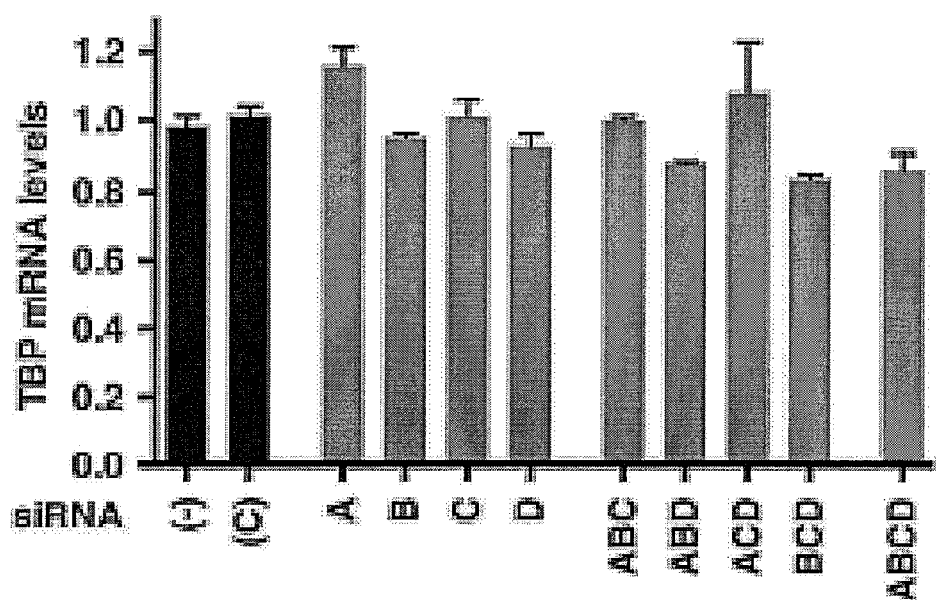

FIGS. 51-53 and FIG. 59 show HeLa cells were transfected with control, individual JMJD2, or combinations of JMJD2s siRNAs, followed by infection with HSV-1 (0.1 pfu/cell) for 2 h. FIGS. 52 and 53: mRNA levels of cellular controls GAPDH and TBP in cells depleted for individual and combinations of JMJD2 proteins. (–) no siRNA; (C), control siRNA.

Figure 54:
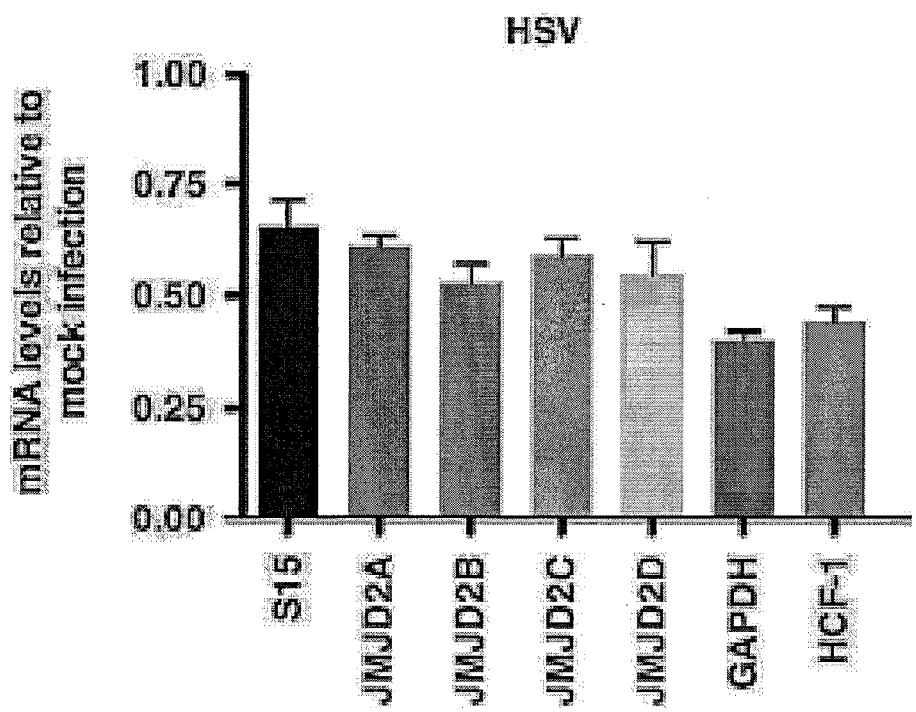
Figure 55:
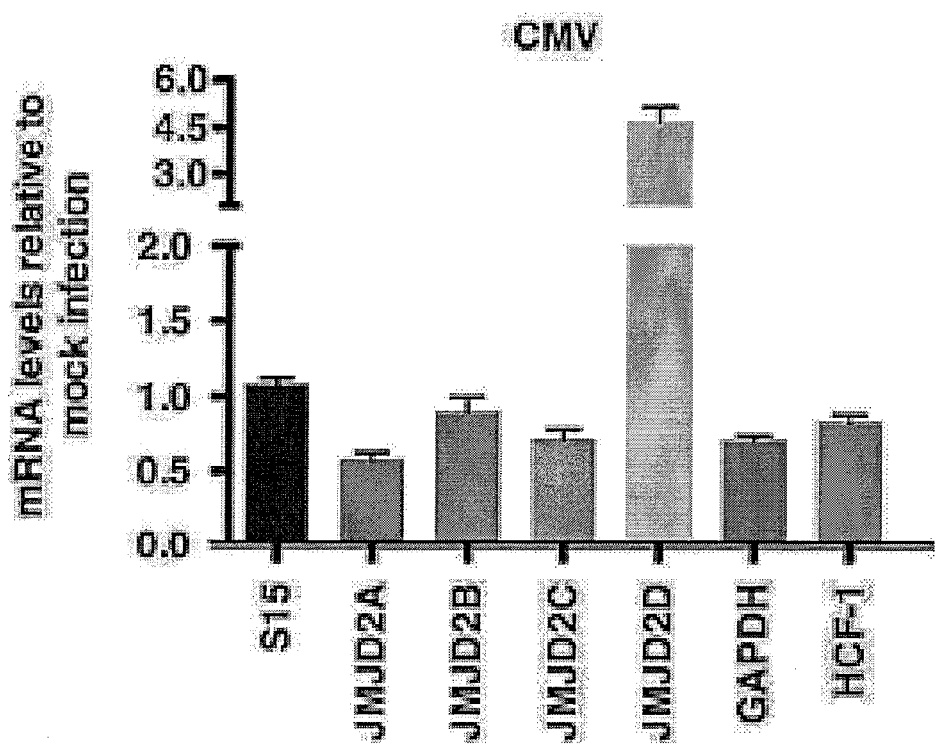
Figure 56:
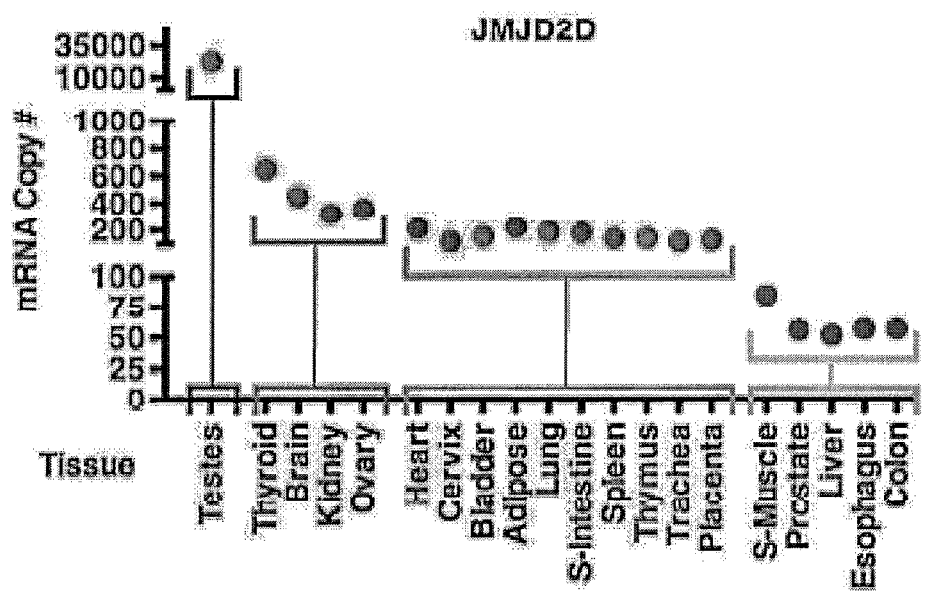
Figure 57:
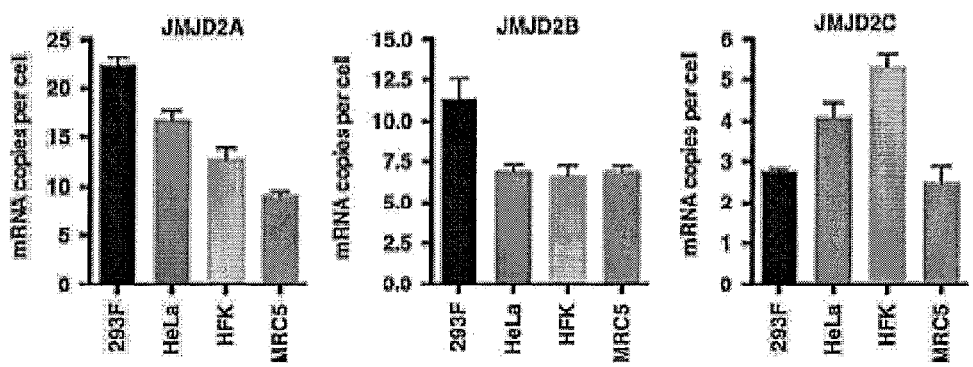
Figure 58:
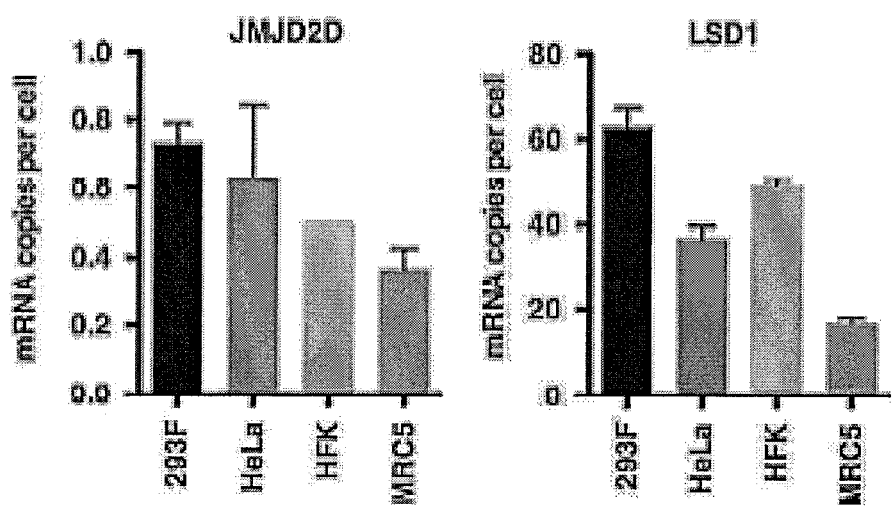
Figure 59:
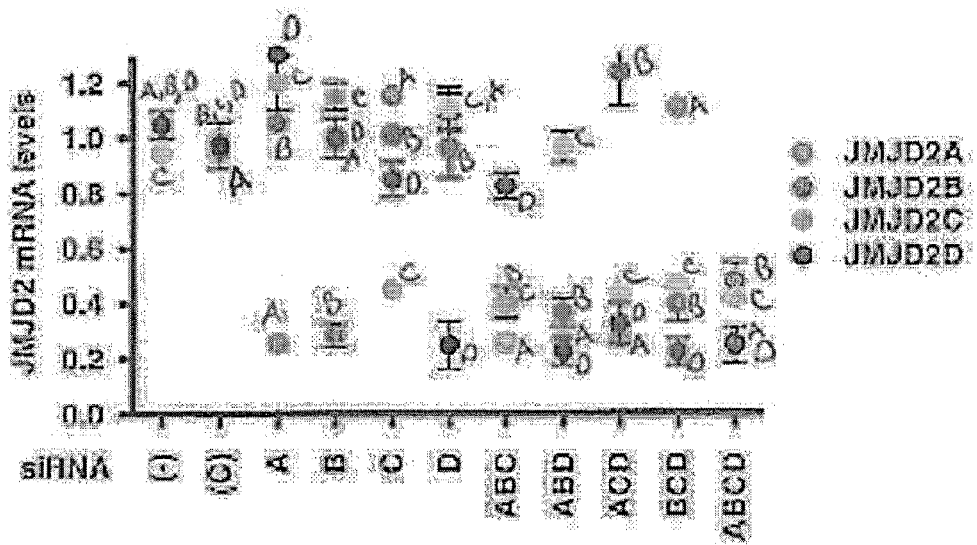
Figure 60:
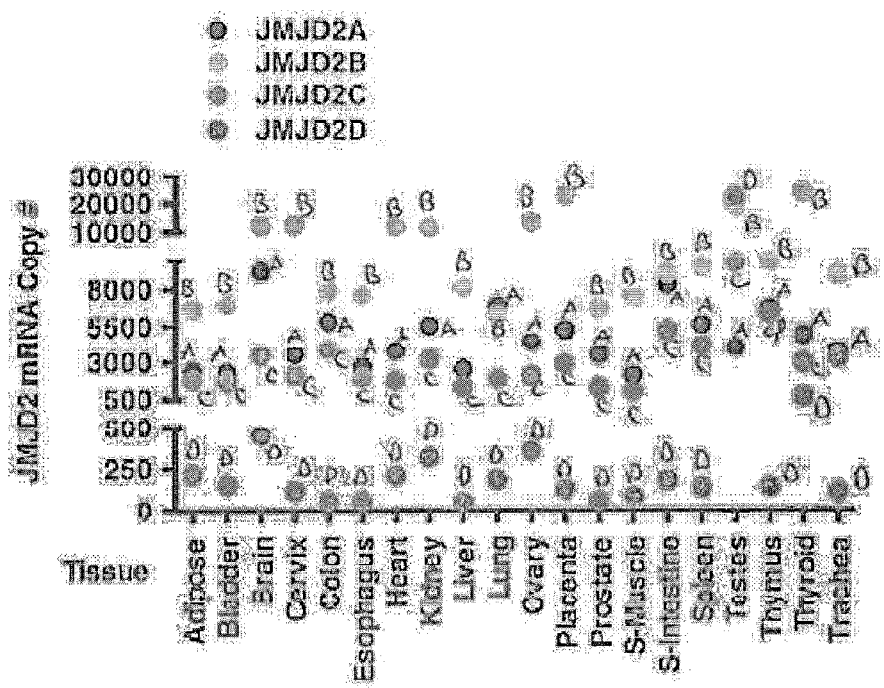

FIGS. 54 and 55 show HFF cells were mock-infected or infected with HSV-1 (10 pfu/cell) or hCMV (0.2 pfu/cell) for 2.5 hrs. The levels of JMJD2, HCF-1, and cellular control mRNAs are expressed relative to the levels in mock-infected cells. The data shown is representative of two independent experiments.

FIGS. 56-58 and 60 show the mRNA levels of JMJD2 family members were determined from equal amounts of RNA from the indicated tissues or cultured cells. Titrations of plasmid DNAs containing the JMJD2 genes were used as qPCR standards. The results are graphed as the absolute copy number per unit of RNA (tissue samples) or the absolute copy number per cell (cultured cells). JMJD2 mRNA copy numbers in tissues were determined using the First Choice Total RNA Survey Panel (Ambion).

DETAILED DESCRIPTION OF THE INVENTION

An embodiment of the invention provides a substance for use in preventing or treating a viral infection of a host, wherein the substance is an inhibitor of a JMJD2 protein.

In an embodiment of the invention, the invention provides a compound of the formula (I)

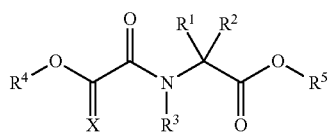 (I)

wherein $R^1$ and $R^2$ are each independently H or $C_1$-$C_6$ alkyl, or together form =$CH_2$, =CH—($C_1$-$C_6$ alkyl) or =C($C_1$-$C_6$ alkyl)($C_1$-$C_6$ alkyl) where the $C_1$-$C_6$ alkyl groups are the same or different; $R^3$ is H or a group of the formula —Y-L-W, wherein Y is linked to N and is $CH_2$, C=O, or NH, L is $C_1$-$C_8$ alkylenyl, $(CH_2)_m$—($C_6$-$C_{20}$ aryl)-$(CH_2)_n$, or $[(CH_2)_rO]_q$ $CH_2$, wherein m and n are each independently 0 to 6, q is 1 to 6, and r is 1 to 3, and W is $R^6$, $COR^6$, $SO_2R^6$, CH=$NR^7$, or $NHOR^7$, wherein $R^6$ is $NR^7R^7$, guanidinyl, a ureido moiety, a carbamate moiety, or $OR^7$, and each $R^7$ is independently H or $CH_3$; $R^4$ and $R^5$ are each independently H, $C_1$-$C_6$ alkyl, $C_6$-$C_{20}$ aryl, or $C_6$-$C_{20}$ aryl $C_1$-$C_6$ alkyl; and X is O, S, or NH; or a pharmaceutically acceptable salt thereof; with the provisos that when $R^4$ and $R^5$ are each H, X is O, and $R^1$ and $R^2$ are each H or one of $R^1$ and $R^2$ is H and the other of $R^1$ and $R^2$ is $C_1$-$C_6$ alkyl, then $R^3$ is not H,

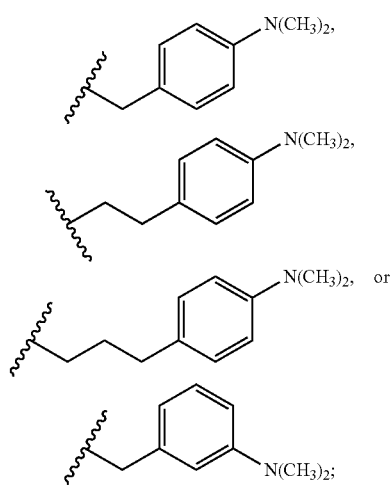

when $R^4$ and $R^5$ are each $C_1$-$C_6$ alkyl, X is O, and $R^1$ and $R^2$ are each H, then $R^3$ is not H or

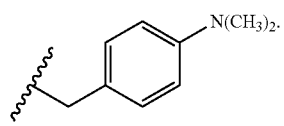 [SMILES: *Cc1ccc(N(C)C)cc1]

In another embodiment of the invention, the compound or salt is as described above, wherein $R^1$ and $R^2$ are each independently H or $C_1$-$C_6$ alkyl; $R^3$ is H or a group of the formula —Y-L-W, wherein Y is linked to N and is $CH_2$, C=O, or NH, L is $C_1$-$C_6$ alkylenyl, $(CH_2)_m$—($C_6$-$C_{20}$ aryl)-$(CH_2)_n$, or $(CH_2CH_2O)_qCH_2$, wherein m and n are each independently 0 to 6 and q is 1 to 6, and W is $R^6$, wherein $R^6$ is $NR^7R^7$ or $OR^7$, and each $R^7$ is independently H or $CH_3$; $R^4$ and $R^5$ are each independently H or $C_1$-$C_6$ alkyl; and X is O.

In yet another embodiment, the invention provides a compound as described above, wherein $R^1$, $R^2$, $R^4$, and $R^5$ are each independently H or $CH_3$.

In yet another embodiment, the invention provides a compound as described above, wherein $R^1$ and $R^2$ are both $C_1$-$C_6$ alkyl.

In another embodiment of the invention, the invention provides a method of preventing or treating a viral infection of a host, comprising administering to the host an effective amount of (a) a compound of the formula (I)

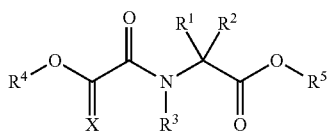 (I)

wherein $R^1$ and $R^2$ are each independently H or $C_1$-$C_6$ alkyl, or together form =$CH_2$, =CH—($C_1$-$C_6$ alkyl) or =C($C_1$-$C_6$ alkyl)($C_1$-$C_6$ alkyl) where the $C_1$-$C_6$ alkyl groups are the same or different; $R^3$ is H or a group of the formula —Y-L-W, wherein Y is linked to N and is $CH_2$, C=O, or NH, L is $C_1$-$C_8$ alkylenyl, $(CH_2)_m$—($C_6$-$C_{20}$ aryl)-$(CH_2)_n$, or $[(CH_2)_rO]_q$ $CH_2$, wherein m and n are each independently 0 to 6, q is 1 to 6, and r is 1 to 3, and W is $R^6$, $COR^6$, $SO_2R^6$, CH=$NR^7$, or $NHOR^7$, wherein $R^6$ is $NR^7R^7$, guanidinyl, a ureido moiety, a carbamate moiety, or $OR^7$, and each $R^7$ is independently H or $CH_3$; $R^4$ and $R^5$ are each independently H, $C_1$-$C_6$ alkyl, $C_6$-$C_{20}$ aryl, or $C_6$-$C_{20}$ aryl $C_1$-$C_6$ alkyl; and X is O, S, or NH; or a pharmaceutically acceptable salt thereof; wherein the administration of the compound prevents or treats the viral infection.

(b) a compound of the formula:

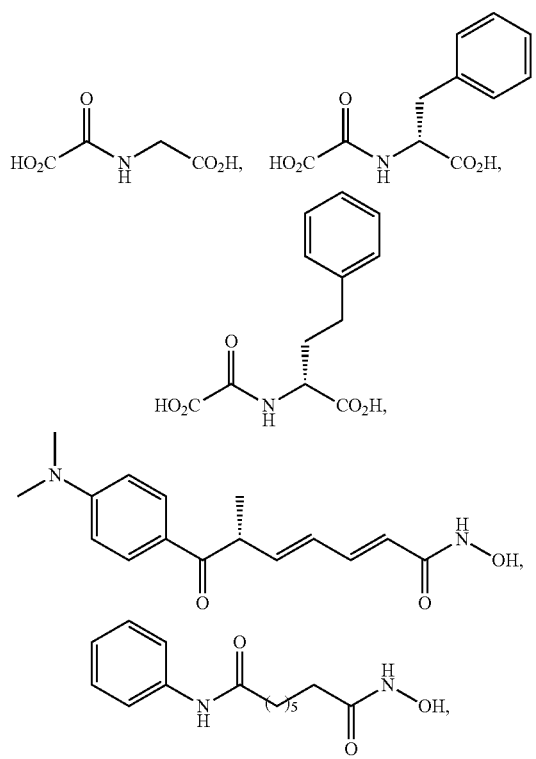

-continued
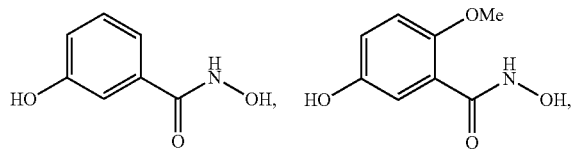
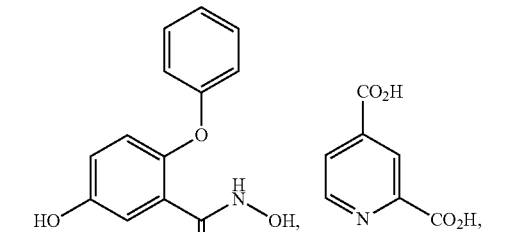
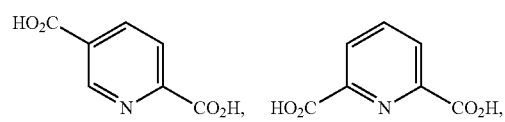
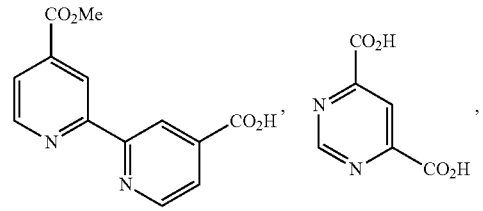
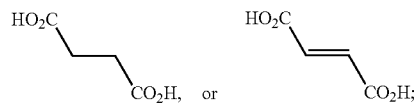
(c) a compound of the formula
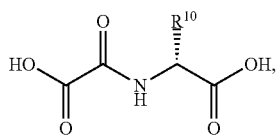
wherein $R^{10}$ is $CH_2SH$,
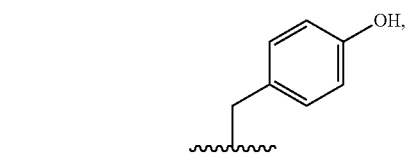 [SMILES: *Cc1ccc(O)cc1]
$CH_2Ph$,
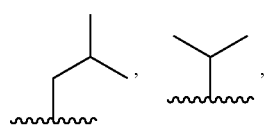
methyl, or $CH_2CH_2Ph$;
(d) a compound of the formula
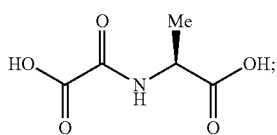 [SMILES: C[C@H](NC(=O)C(=O)O)C(=O)O]
(e) a compound of the formula
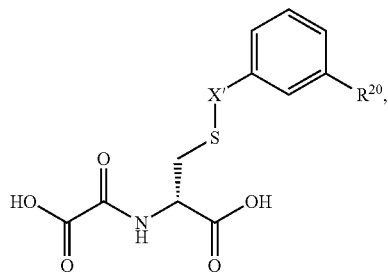
wherein $R^{20}$ is $OCH_3$ or H and X' is S or $CH_2$;
(f) a compound of the formula
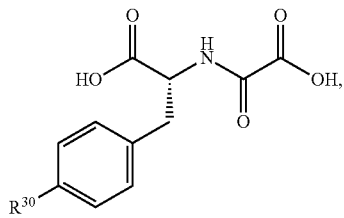
wherein $R^{30}$ is
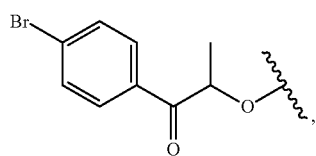
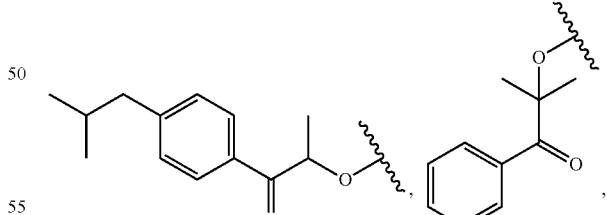
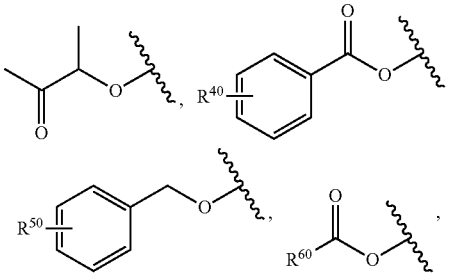

-continued

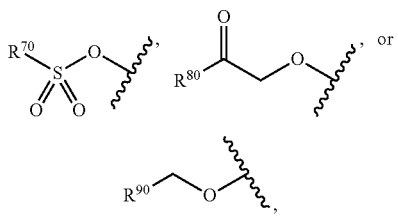

wherein $R^{40}$ is H, 2-methyl, 4-phenyl, 3-fluoro, 2,4-difluoro, 2-chloro, 3-methoxy, or 4-cyano, wherein $R^{50}$ is H, 2-methyl, 4-methyl, 2,4,6-trimethyl, 2-fluoro, 3,4-difluoro, 2-fluoro-3-trifluoromethyl, 4-chloro, 3-methoxy, 3-chloro, 2-nitro, 2-methoxy-5-nitro, 4-methoxycarbonyl, 3-cyano, or 4-(2,3,4-thiadiazolyl), wherein one, two, three, four, or five groups of $R^{40}$ or $R^{50}$ can be present on the phenyl ring, wherein $R^{60}$ is

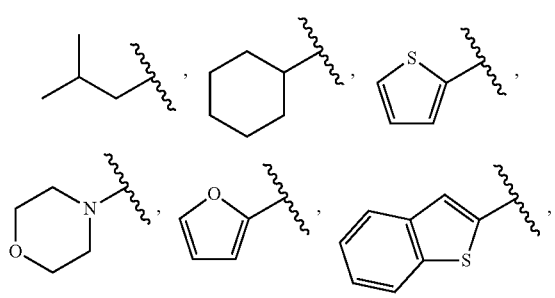

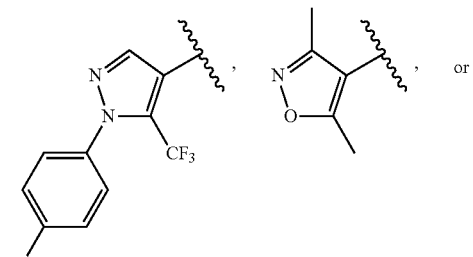

wherein $R^{70}$ is

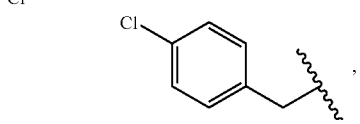

-continued

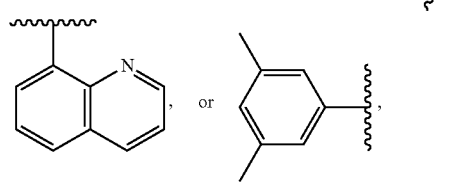

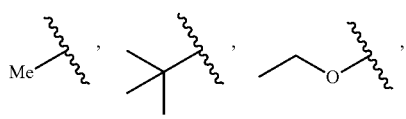

wherein $R^{80}$ is

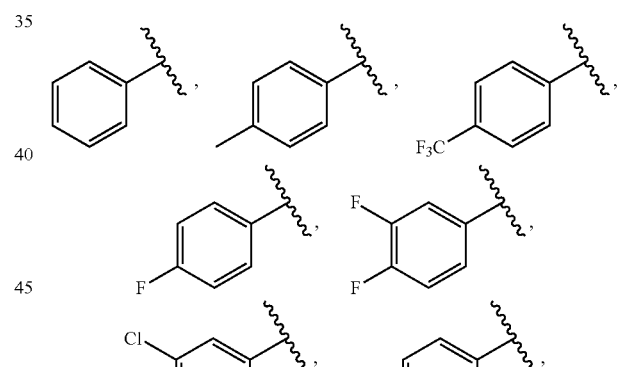

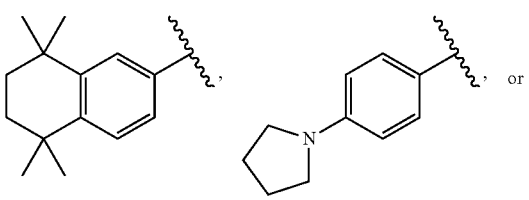

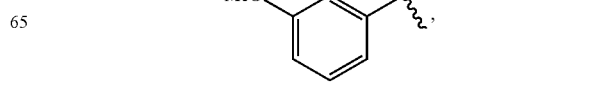

wherein $R^{90}$ is

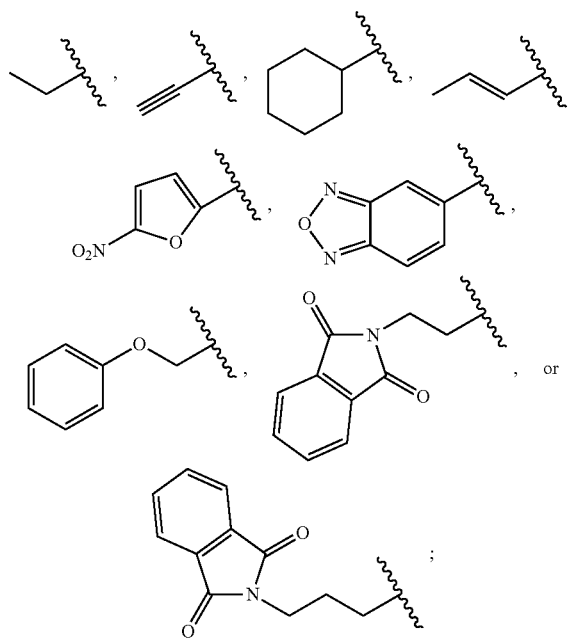

(g) a compound of the formula

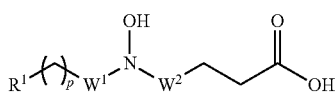

wherein $R^1$ is $C_1$-$C_4$ alkyl, NH($C_1$-$C_4$ alkyl), N($C_1$-$C_4$ alkyl) benzyl, N($C_1$-$C_4$ alkyl)($C_1$-$C_4$ alkyl) where the $C_1$-$C_4$ alkyl groups are the same or different; $W^1$ and $W^2$ are each independently CO or a N—C bond; and p is 0 to 11;

(h) a compound of the formula (II):

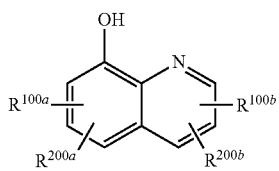

(II)

wherein
$R^{100a}$ and $R^{100b}$ are independently selected from H, $R^{300}$,

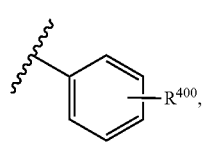

and $R^{600}$, wherein at least one of $R^{100a}$ and $R^{100b}$ is H;
$R^{200a}$ and $R^{200b}$ are independently selected from H and COOH, wherein at least one of $R^{200a}$ and $R^{200b}$ is H;
$R^{300}$ is selected from

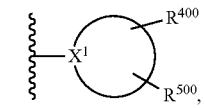 (i)

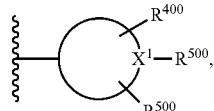 (ii)

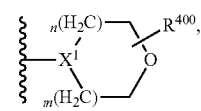 (iii)

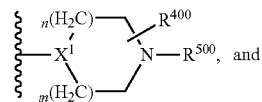 (iv)

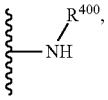 (v)

wherein $X^1$ is CH or N,
wherein the rings (i) and (ii) are 3 to 8 membered cycloaliphatic or heterocyclic rings,
wherein n is 0, 1, or 2, wherein m is 0, 1, or 2;
$R^{400}$ and $R^{500}$ are independently selected from
H, $R^{300}$, $R^{600}$, —($C_1$-$C_6$ alkyl)-$R^{300}$, ($C_1$-$C_6$ alkyl)-$R^{600}$, —C($X^3$)$X^4$—$R^{700}$, —C(O)—$R^{700}$, —NH—$R^{700}$, or $R^{400}$ and $R^{500}$ are taken together to form a heteroring, wherein $X^3$ is selected from O and S, and $X^4$ is selected from NH and O;
$R^{600}$ is selected from
H, NH$_2$, —NH($C_1$-$C_6$ alkyl), —N($C_1$-$C_6$ alkyl)($C_1$-$C_6$ alkyl), phenyl, and pyridine;
and
$R^{700}$ is selected from
H, $R^{300}$, —($C_1$-$C_6$ alkyl)-$R^{300}$, and —($C_1$-$C_6$ alkyl)-$R^{600}$; or (i) an siRNA directed against a member of the JMJD2 family of histone demethylases;
or a pharmaceutically acceptable salt thereof;
wherein the administration of the compound prevents or treats the viral infection.

In a further embodiment, the invention provides a substance as described herein for use in preventing or treating a viral infection of a host.

In a further embodiment, the invention provides the above method, wherein the compound of formula (I) is such that $R^1$ and $R^2$ are each independently H or $C_1$-$C_6$ alkyl; $R^3$ is H or a group of the formula —Y-L-W, wherein Y is linked to N and is CH$_2$, C=O, or NH, L is $C_1$-$C_6$ alkylenyl, (CH$_2$)$_m$—(C$_6$-C$_{20}$ aryl)-(CH$_2$)$_n$, or (CH$_2$CH$_2$O)$_q$CH$_2$, wherein m and n are each independently 0 to 6 and q is 1 to 6, and W is $R^6$, wherein $R^6$ is NR$^7$R$^7$ or OR$^7$, and each $R^7$ is independently H or CH$_3$; $R^4$ and $R^5$ are each independently H or $C_1$-$C_6$ alkyl; and X is O.

In a further embodiment, the invention provides the above method, wherein the compound of formula (I) is such that $R^1$, $R^2$, $R^4$, and $R^5$ are each independently H or CH$_3$.

In another embodiment, the invention provides the above method, wherein the compound of formula (I) is N-oxalylglycine, dimethyloxalylglycine, which has the structure

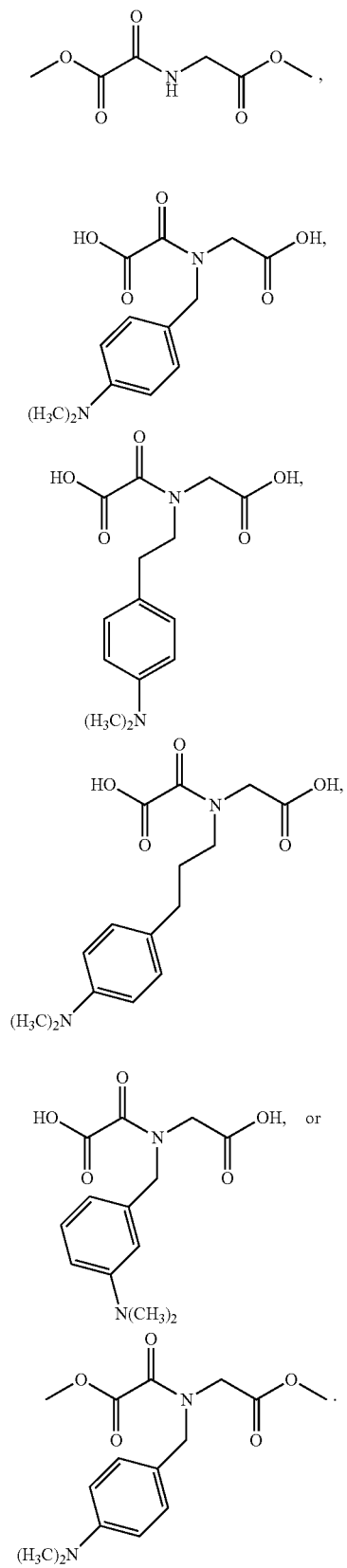
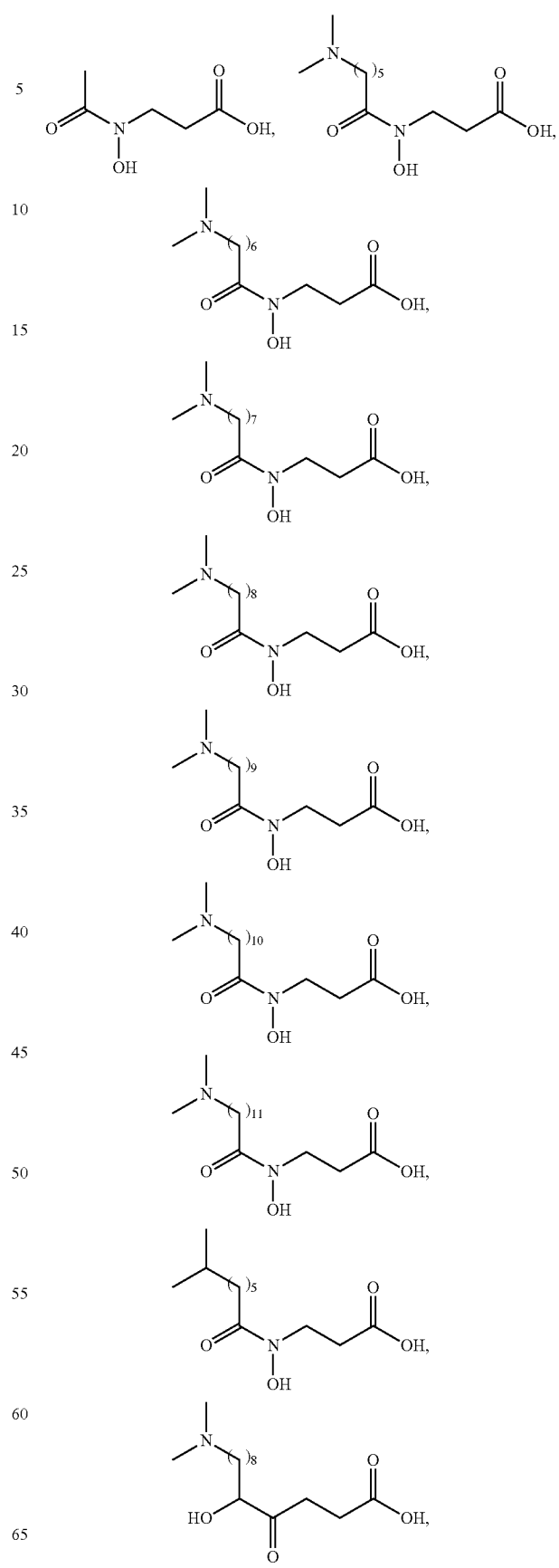
In another embodiment, the invention provides the above method, wherein the compound is

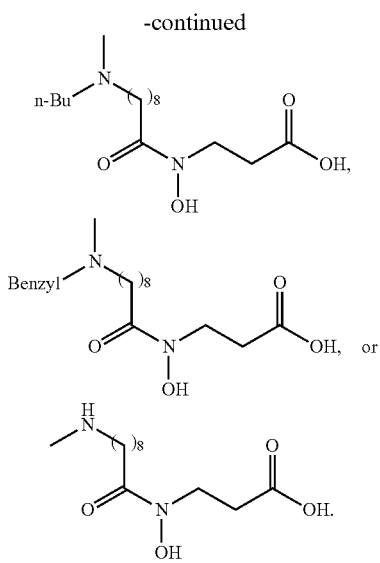

In another embodiment of the compounds of formula (II), the invention provides the following compounds and use of the compounds in the above method, wherein the compound is

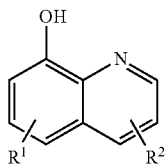

wherein
$R^1$ is selected from
H, COOH,

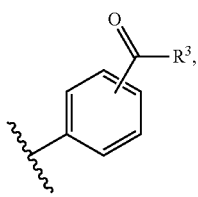

and dialkylaminoalkylaminocarbonylaryl,
$R^2$ is selected from
H, heterocyclyl, alkylheterocyclyl, aminoheterocyclyl, heterocyclylamino, arylalkylheterocyclyl, heterocyclylaryl, arylalkylheterocyclylalkylamino, heteroarylalkylheterocyclyl, heterocyclylcarbonylaryl, alkylheterocyclylcarbonylaryl, dialkylaminoalkylaminocarbonylaryl, cycloalkylheterocyclyl, and aminocarbonylaryl,
$R^3$ is selected from
heterocyclyl, alkylheterocyclyl, heterocyclylalkylamino, dialkylaminoalkylheterocyclylheterocyclyl, dialkylaminoalkylheterocyclyl, alkylheterocyclylalkylamino, and alkylheterocyclylamino,
wherein at least one of $R^1$ and $R^2$ is not H;
or a pharmaceutically acceptable salt thereof.

In certain embodiments of the compounds in the above paragraph, heterocyclyl is, e.g., piperazinyl, piperidinyl, 1,3-piperidinyl, morpholinyl, pyrrolidinyl, pyrrolopyrrolidinyl, or homopiperazinyl. In certain embodiments of the compounds in the above paragraph, aryl is, e.g., phenyl, pyridinyl, or pyrimidinyl. In certain embodiments of the compounds in the above paragraph, $R^3$ is, e.g., piperazinyl, methylpiperazinyl, piperazinylpropylamino, dimethylaminomethylpiperidinylpiperidinyl, dimethylaminopropylhexahydropyrimidinyl, morpholinylpropylamino, or methylpiperazinylpropylamino. In certain embodiments of the compounds in the above paragraph, $R^1$ is, e.g., dimethylaminopropylaminocarbonylphenyl or dimethylaminohexylaminocarbonylphenyl. In certain embodiments of the compounds in the above paragraph, $R^2$ is, e.g., dimethylaminopropylaminocarbonylphenyl, piperazinyl, methylpiperazinyl, morpholinyl, piperidinyl, aminopiperidinyl, pyrrolidinyl, pyrrolidinylamino, aminopyrrolidinyl, octahydropyrrolo[3,4-c]pyrrolyl, phenylmethylpiperazinyl, morpholinylphenyl, phenylethylpiperidinylmethylamino, pyridinylethylpiperidinyl, piperazinylcarbonylphenyl, methylpiperazinylcarbonylphenyl, methylaminopropylaminocarbonylphenyl, cyclopentylhomopiperazinyl, pyridinylpropylhomopiperazinyl, or aminocarbonylphenyl.

In another embodiment, the invention provides the following compounds and use of the compounds in the above method, wherein the compound is

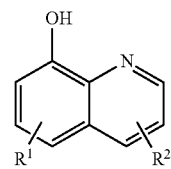

wherein
$R^1$ is selected from

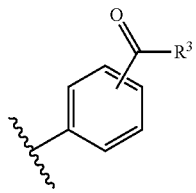

and dialkylaminoalkylaminocarbonylaryl,
$R^2$ is H, and
$R^3$ is selected from
heterocyclyl, alkylheterocyclyl, heterocyclylalkylamino, dialkylaminoalkylheterocyclylheterocyclyl, dialkylaminoalkylheterocyclyl, alkylheterocyclylalkylamino, and alkylheterocyclylamino,
or a pharmaceutically acceptable salt thereof.

In certain embodiments of the compounds in the above paragraph, heterocyclyl is, e.g., piperazinyl, piperidinyl, 1,3-piperidinyl, morpholinyl, pyrrolidinyl, pyrrolopyrrolidinyl, or homopiperazinyl. In certain embodiments of the compounds in the above paragraph, aryl is, e.g., phenyl, pyridinyl, or pyrimidinyl. In certain embodiments of the compounds in the above paragraph, $R^3$ is, e.g., piperazinyl, methylpiperazinyl, piperazinylpropylamino, dimethylaminomethylpiperidinylpiperidinyl, dimethylaminopropylhexahydropyrimidinyl, morpholinylpropylamino, or methylpiperazinylpropylamino. In certain embodiments of the compounds in the above paragraph, $R^1$ is, e.g., dimethylaminopropylaminocarbonylphenyl or dimethylaminohexylaminocarbonylphenyl. In certain embodiments of the compounds in the above paragraph, $R^2$ is, e.g., dimethylaminopropylaminocarbonylphenyl, piperazinyl, methylpiperazinyl, morpholinyl, piperidinyl, aminopiperidinyl, pyrrolidinyl, pyrrolidinylamino, aminopyrrolidinyl, octahydropyrrolo[3,4-c]pyrrolyl, phenylmethylpiperazinyl, morpholinylphenyl, phenylethylpiperidinylmethylamino, pyridinylethylpiperidinyl, piperazinyl carbonylphenyl, methylpiperazinylcarbonylphenyl, methylaminopropylaminocarbonylphenyl, cyclopentylhomopiperazinyl, pyridinylpropylhomopiperazinyl, or aminocarbonylphenyl.

In another embodiment, the invention provides the following compounds and use of the compounds in the above method, wherein the compound is

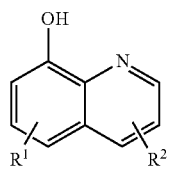

wherein $R^1$ is COOH, and $R^2$ is selected from

H, heterocyclyl, alkylheterocyclyl, aminoheterocyclyl, heterocyclylamino, arylalkylheterocyclyl, heterocyclylaryl, arylalkylheterocyclylalkylamino, heteroarylalkylheterocyclyl, heterocyclylcarbonylaryl, alkylheterocyclylcarbonylaryl, dialkylaminoalkylaminocarbonylaryl, cycloalkylheterocyclyl, and aminocarbonylaryl, or a pharmaceutically acceptable salt thereof.

In certain embodiments of the compounds in the above paragraph, heterocyclyl is, e.g., piperazinyl, piperidinyl, 1,3-piperidinyl, morpholinyl, pyrrolidinyl, pyrrolopyrrolidinyl, or homopiperazinyl. In certain embodiments of the compounds in the above paragraph, aryl is, e.g., phenyl, pyridinyl, or pyrimidinyl. In certain embodiments of the compounds in the above paragraph, $R^3$ is, e.g., piperazinyl, methylpiperazinyl, piperazinylpropylamino, dimethylaminomethylpiperidinylpiperidinyl, dimethylaminopropylhexahydropyrimidinyl, morpholinylpropylamino, or methylpiperazinylpropylamino. In certain embodiments of the compounds in the above paragraph, $R^1$ is, e.g., dimethylaminopropylaminocarbonylphenyl or dimethylaminohexylaminocarbonylphenyl. In certain embodiments of the compounds in the above paragraph, $R^2$ is, e.g., dimethylaminopropylaminocarbonylphenyl, piperazinyl, methylpiperazinyl, morpholinyl, piperidinyl, aminopiperidinyl, pyrrolidinyl, pyrrolidinylamino, aminopyrrolidinyl, octahydropyrrolo[3,4-c]pyrrolyl, phenylmethylpiperazinyl, morpholinylphenyl, phenyl ethylpiperidinylmethylamino, pyridinylethylpiperidinyl, piperazinylcarbonylphenyl, methylpiperazinylcarbonylphenyl, methylaminopropylaminocarbonylphenyl, cyclopentylhomopiperazinyl, pyridinylpropylhomopiperazinyl, or aminocarbonylphenyl.

In another embodiment, the invention provides the following compounds and use of the compounds in the above method, wherein the compound is a compound of formula (II) and is any of the following:

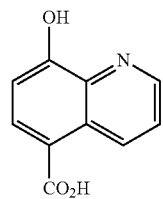 1

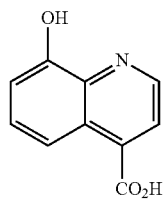 2

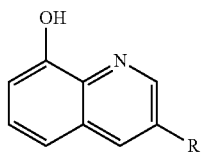 3

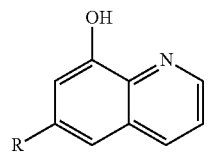 4-5

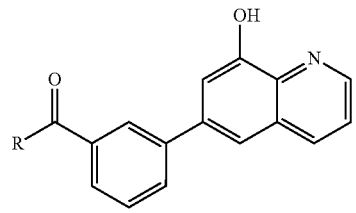 6-9 wherein R is

1  NA

2  NA

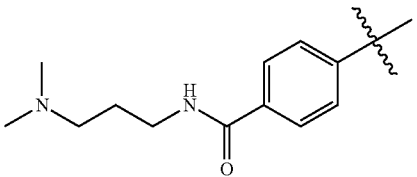 [SMILES: *c1ccc(C(=O)NCCCN(C)C)cc1] 3

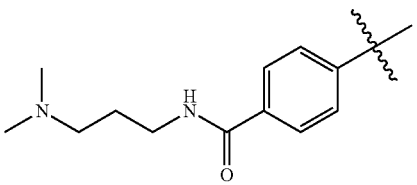 4

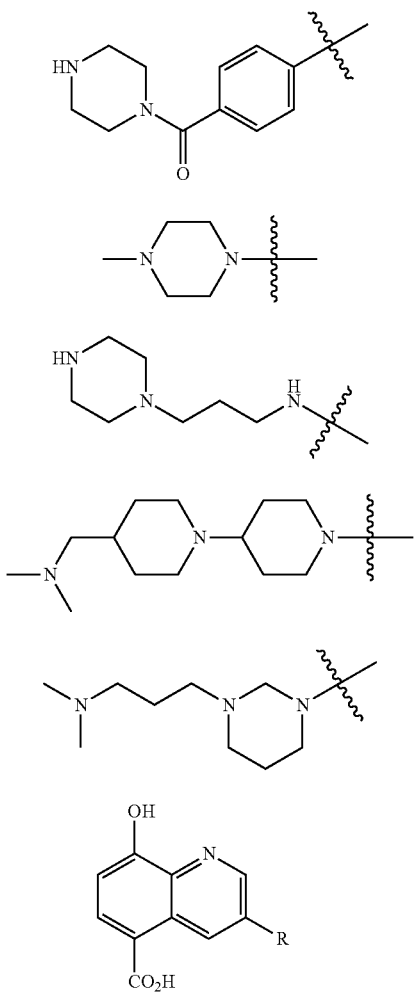
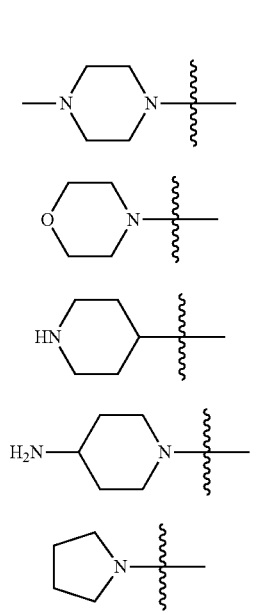
wherein R is
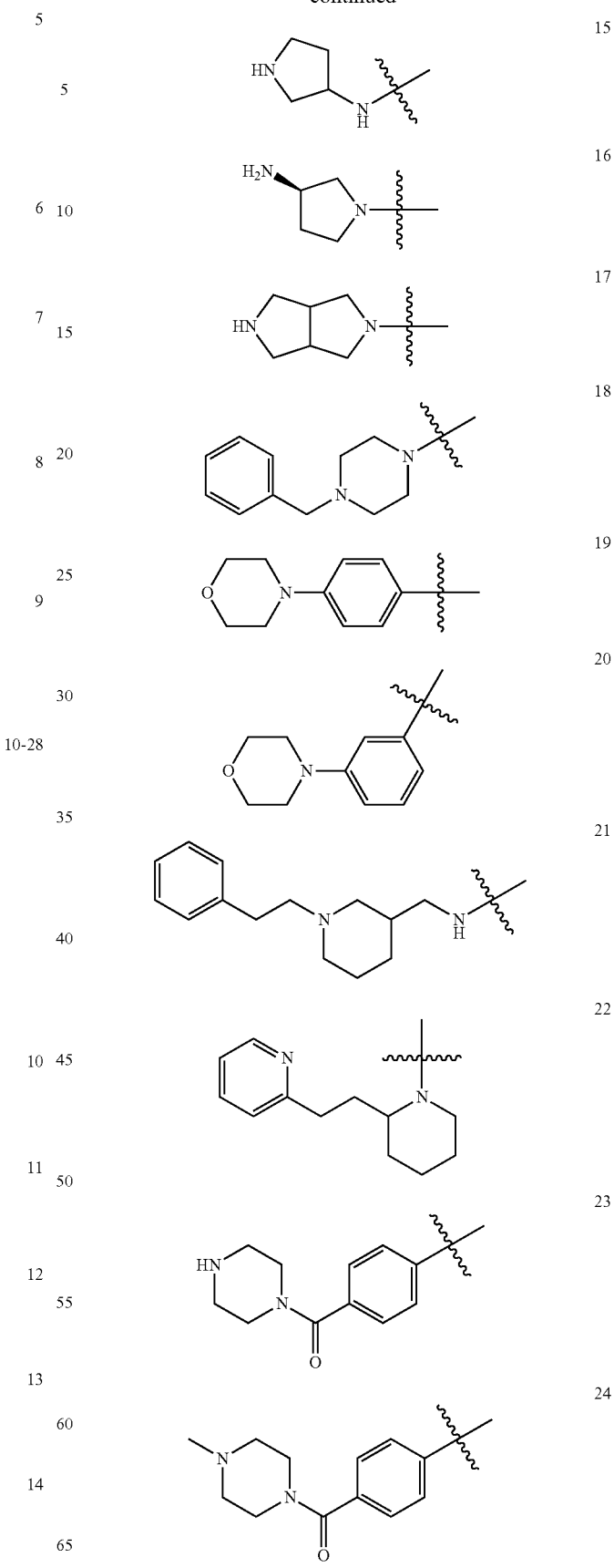

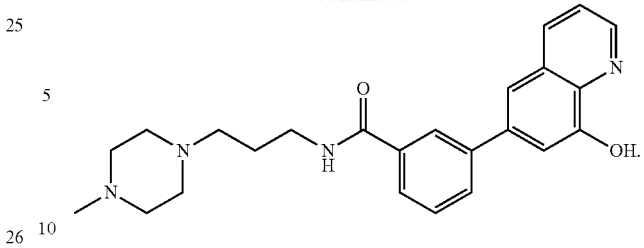

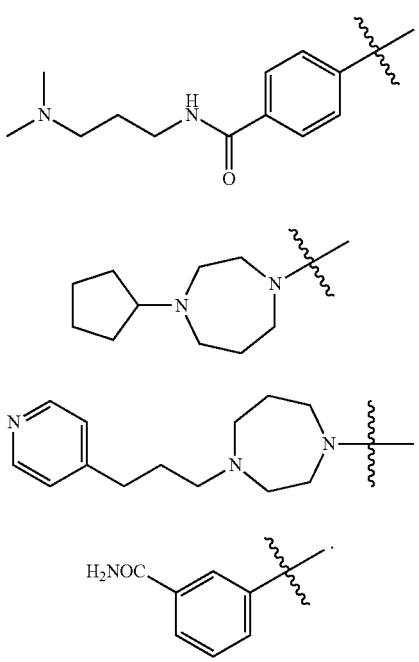

Additional examples include compounds of the formula:

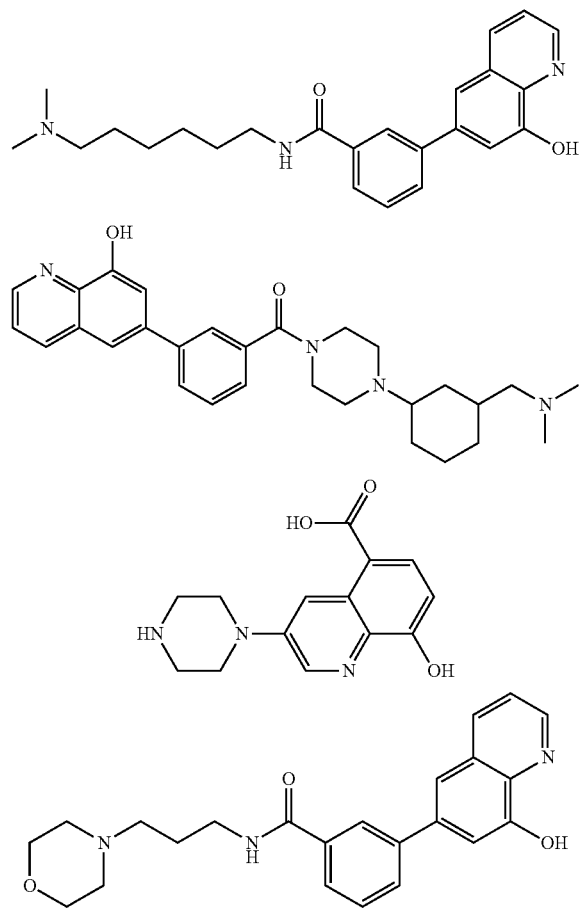

In yet another embodiment, the invention provides a method of preventing or treating reactivation of a virus after latency in a host, comprising administering to the host an effective amount of any compound as described above.

In yet another embodiment, the invention provides a method of preventing or treating a viral infection in a mammal that has undergone, is undergoing, or will undergo an organ or tissue transplant, comprising administering to the mammal an effective amount of any compound as described above.

In a further embodiment, the invention provides a method of inhibiting a member of the JMJD2 family of histone demethylases in a virus-infected host, comprising administering to the host an effective amount of any compound as described above.

In a further embodiment, the invention provides a substance as described herein for use in inhibiting a member of the JMJD2 family of histone demethylases in a virus-infected host.

A "host" may be considered a single cell, a tissue, an organ, or an individual organism, such as a mammal. The mammal can be any suitable mammal, such as a mammal selected from the group consisting of a mouse, rat, guinea pig, hamster, cat, dog, pig, cow, horse, and primate. In one embodiment, the mammal is a human.

A viral infection is present in a host when a virus replicates itself within the host. A virus contains its own genetic material but uses the machinery of the host to reproduce. The virus may reproduce immediately, whereby the resulting virions destroy a host cell to attack additional cells. This process is the viral lytic cycle. Alternatively, a virus may establish a quiescent infection in a host cell, lying dormant until environmental stimuli trigger re-entry into the lytic replication cycle. Such re-emergence or re-entry into the lytic replication cycle is termed reactivation. In an embodiment of the invention, the host has a viral infection or is at risk for viral infection but is free from cancer.

The viral infection may be due to a nuclear DNA viral infection such as a herpes viral infection. The herpesvirus may be, e.g., herpes simplex virus (HSV) type 1, herpes simplex virus type 2, varicella zoster virus (VZV), or cytomegalovirus (CMV). The herpesvirus may be Epstein-Barr virus (EBV), Kaposi's Sarcoma-Associated herpesvirus, herpes simiae virus, herpes lymphotropic virus, human herpesvirus-7 (HHMV-7), or human herpesvirus-8 (HHMV-8).

Viral infections especially pose a threat to individuals that have suppressed (immunosuppressed) or otherwise compromised (immunocompromised) immune systems. For example, individuals with HIV/AIDS, diabetes, or cancer often have reduced ability to ward off additional and/or opportunistic viral infections due to immune systems that are adversely affected by the underlying, primary infection or condition. Therefore, preventing or treating viral infection or re-activation is especially important for these individuals.

Another embodiment of the invention provides a method of preventing or treating a viral infection in a mammal that has undergone, is undergoing, or will undergo an organ or tissue transplant, comprising administering to the mammal an effective amount of any of the compounds described above, wherein the administration of the inhibitor(s) prevents or treats the viral infection. A non-limiting example would be to administer an effective amount of an inhibitor of the JMJD2 family of histone demethylases and/or a dimethyloxalylglycine or analog thereof to a mammal undergoing immunosuppressive therapy and who is suspected of being infected with virus.

Other inhibitors of the JMJD2 family of histone demethylases can be used. A suitable inhibitor includes a nucleic acid (e.g., RNA), protein, small molecule, or antibody that specifically binds to a JMJD2 histone demethylase, inhibits translation of a JMJD2 histone demethylase, inhibits transcription of a JMJD2 histone demethylase, or otherwise interferes with the biological expression and/or activity of a JMJD2 histone demethylase. One such inhibitor is an RNA interference (RNAi) inhibitor. The RNAi inhibitor may comprise any RNA sequence that is complementary to the target JMJD2 histone demethylase nucleic acid or a portion thereof, and include small inhibitor RNA (siRNA) directed against any of the members of the JMJD2 family (a, b, c, and/or d). Antibodies and RNAi inhibitors of JMJD2 histone demethylases can be prepared using routine techniques.

Methylation of chromatin, a reversible modification mediated by histone methyl-transferases and demethylases, is a significant component of cellular transcriptional regulation. Such chromatin modifications also impact invading viral pathogens that rely upon the host cell transcriptional apparatus. During infection of cells by viruses, the assembly and modification of chromatin on the viral genomes has the potential to determine the progression of lytic infection as well as control recurrent latency-reactivation cycles. Without intending to be bound by any theory, HCF-1 is a cellular transcriptional coactivator that is required for the expression of the immediate early genes (IE), such as the IE genes of α-herpesviruses HSV-1 and VZV-1, during the initiation of lytic infection. Viruses, such as HSV and VZV, utilize virion-encapsidated transcriptional activators to recruit the HCF-1-Set/MLL1 histone methyl-transferase (HMT) complexes to the viral IE promoters, resulting in histone H3-lysine 4 (H3K4) trimethylation and initiation of IE gene transcription. Furthermore, depletion of HCF-1 results in an increase in the levels of repressive histone H3-lysine 9 (H3K9) methylation, providing a central role for HCF-1 in modulating chromatin modifications that determine viral gene expression. A description of the role of HCF-1 in reactivation from latency is set forth in Whitlow and Kristie (J. Virol., 2009, 83:9591-5); Kolb and Kristie (J. Virol., 2008, 82:9555-63); and Kristie, Liang, and Vogel (Biochim. Biophys. Acta., 2010, 1799:257-65 (published online Aug. 12, 2009). The JMJD2 family members interact with HCF-1 and have been shown to possess H3K9 demethylase activity which is important for the activation of nuclear hormone receptor-dependent transcription, cell fate determination, and cell cycle progression.

LSD1 (also known as BHC110) also interacts with HCF-1 and has been shown to possess H3K9 demethylase activity. LSD1 demethylates lysine residues via a flavin-adenine-dinucleotide-dependent reaction that is inhibited by MAOIs and siRNA (International Patent Application No. PCT/US2009/051557, published as WO 2010/011845, which is incorporated by reference). Inhibition of LSD1 activity not only results in a block to viral IE gene expression in lytic infection but also prevents the reactivation of HSV from latency in a mouse ganglia explant model system, indicating that HCF-1 chromatin modulation complexes play a role in the viral latency-reactivation cycle. Either the JMJD2 family of histone demethylases or LSD1, or both simultaneously, may be inhibited to achieve inhibition of viral infection or reactivation. Inhibitors of LSD1 include the MAOIs Pargyline, SELEGILINE, and tranylcypromine (TCP).

As used herein, unless otherwise specified, the term "alkyl" means a saturated straight chain or branched non-cyclic hydrocarbon having an indicated number of carbon atoms (e.g., $C_1$-$C_{20}$, $C_1$-$C_{10}$, $C_1$-$C_4$, etc.). Representative saturated straight chain alkyls include -methyl, -ethyl, -n-propyl, -n-butyl, -n-pentyl, -n-hexyl, -n-heptyl, -n-octyl, -n-nonyl and -n-decyl; while representative saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like.

The term "cycloalkyl," as used herein, means a cyclic alkyl moiety containing from, for example, 3 to 6 carbon atoms, preferably from 5 to 6 carbon atoms. Examples of such moieties include cyclopropyl, cyclobutyl, cyclopentyl, cyclohexyl, and the like.

The term "heterocyclyl" means a cycloalkyl moiety having one or more heteroatoms selected from nitrogen, sulfur, and/or oxygen. Preferably, a heterocyclyl is a 5 or 6-membered monocyclic ring and contains one, two, or three heteroatoms selected from nitrogen, oxygen, and/or sulfur. The heterocyclyl can be attached to the parent structure through a carbon atom or through any heteroatom of the heterocyclyl that results in a stable structure. Examples of such heterocyclic rings are pyrrolinyl, pyranyl, piperidyl, tetrahydrofuranyl, tetrahydrothiopheneyl, and morpholinyl.

As used herein, unless otherwise specified, the term "alkylamino" means —NH(alkyl) or —N(alkyl)(alkyl), wherein alkyl is defined above. As used herein, unless otherwise specified, the term "cycloalkylamino" means —NH(cycloalkyl) or —N(cycloalkyl)(cycloalkyl), wherein cycloalkyl is defined above.

The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise $4n+2$ π electrons, according to Hückel's Rule, wherein $n=1$, 2, or 3.

The term "heteroaryl" refers to aromatic 4, 5, or 6 membered monocyclic groups, 9 or 10 membered bicyclic groups, and 11 to 14 membered tricyclic aryl groups having one or more heteroatoms (O, S, or N). Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The nitrogen and sulfur atoms may optionally be oxidized, and the nitrogen atoms may optionally be quaternized. Illustrative examples of heteroaryl groups are pyridinyl, pyridazinyl, pyrimidyl, pyrazinyl, triazinyl, pyrrolyl, pyrazolyl, imidazolyl, (1,2,3),- and (1,2,4)-triazolyl, pyrazinyl, pyrimidinyl, tetrazolyl, furyl, thiophenyl, isothiazolyl, thiazolyl, isoxazolyl, oxadiazolyl, oxazolyl, pyrrolo[2,3-c]pyridinyl, pyrrolo[3,2-c]pyridinyl, pyrrolo[2,3-b]pyridinyl, pyrrolo[3,2-b]pyridinyl, pyrrolo[3,2-d]pyrimidinyl, and pyrrolo[2,3-d]pyrimidinyl.

Whenever a range of the number of atoms in a structure is indicated (e.g., a $C_1$-$C_8$, $C_1$-$C_6$, $C_1$-$C_4$, or $C_1$-$C_3$ alkyl, haloalkyl, alkylamino, alkenyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, haloalkyl, alkylamino, alkenyl, etc.) referenced herein encompasses and specifically describes 1, 2, 3, 4, 5, 6, 7, or 8 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 2-3 carbon atoms, 2-4 carbon atoms, 2-5 carbon atoms, 2-6 carbon atoms, 2-7 carbon atoms, 2-8 carbon atoms, 3-4 carbon atoms, 3-5 carbon atoms, 3-6 carbon atoms, 3-7 carbon atoms, 3-8 carbon atoms, 4-5 carbon atoms, 4-6 carbon atoms, 4-7 carbon atoms, 4-8 carbon atoms, 5-6 carbon atoms, 5-7 carbon atoms, 5-8 carbon atoms, 6-7 carbon atoms, or 6-8 carbon atoms, as appropriate).

An inhibitor of the JMJD2 family of histone demethylases and/or any compound or RNAi described above can be administered in a composition (e.g., pharmaceutical composition) that can comprise at least one carrier (e.g., a pharmaceutically acceptable carrier), as well as other therapeutic agents (e.g., other inhibitors of the JMJD2 family of histone demethylases). The composition can be administered by any suitable route, including parenteral, topical, oral, or local administration. One embodiment of the invention is topical administration of an inhibitor of the JMJD2 family of histone demethylases. Such topical administration may be accomplished using a gel, cream or lotion formulation for, e.g., the clearance of cold sores (HSV-1), genital sores (HSV-2), shingles (VZV), or herpetic keratitis.

The pharmaceutically acceptable carrier (or excipient) is preferably one that is chemically inert to the inhibitor of the JMJD2 family of histone demethylases and one that has little or no side effects or toxicity under the conditions of use. Such pharmaceutically acceptable carriers include, but are not limited to, water, saline, Cremophor EL (Sigma Chemical Co., St. Louis, Mo.), propylene glycol, polyethylene glycol, alcohol, and combinations thereof. The choice of carrier will be determined in part by the particular inhibitor of the JMJD2 family of histone demethylases as well as by the particular method used to administer the composition. Accordingly, there is a wide variety of suitable formulations of the composition.

Preservatives may be used in the pharmaceutical composition. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may be used in the pharmaceutical composition and may include, for example, citric acid and sodium citrate, phosphoric acid and potassium phosphate, and various other acids and salts. A mixture of two or more buffering agents optionally may be used. The buffering agent or mixtures thereof are typically present in an amount of about 0.001% to about 4% by weight of the total composition.

The following formulations for oral, nasal, parenteral (e.g., subcutaneous, intravenous, intraarterial, intramuscular, intradermal, interperitoneal, and intrathecal), and rectal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art. A component of the formulation may serve more than one function.

The inhibitors of the JMJD2 family of histone demethylases, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inhibitors of the JMJD2 family of histone demethylases may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations may include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets.

The inhibitors of the JMJD2 family of histone demethylases may be administered as an injectable formulation. The requirements for effective pharmaceutical carriers for injectable compositions are well known to those of ordinary skill in the art. See Pharmaceutics and Pharmacy Practice, J. B. Lippincott Co., Philadelphia, Pa., Banker and Chalmers, eds., pages 238-250 (1982), and ASHP Handbook on Injectable Drugs, Toissel, 4th ed., pages 622-630 (1986).

Topical formulations, including those that are useful for transdermal drug release, are well known to those of skill in the art and are suitable in the context of embodiments of the invention for application to skin.

The concentration of a compound of embodiments of the invention in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, Remington: The Science and Practice of Pharmacy, Lippincott Williams & Wilkins, 21st ed. (2005).

In addition to the aforedescribed pharmaceutical compositions, the inhibitors of the JMJD2 family of histone demethylases can be formulated as inclusion complexes, such as cyclodextrin inclusion complexes, or liposomes. Liposomes can serve to target the inhibitor of the JMJD2 family of histone demethylases to a particular tissue. Liposomes also can be used to increase the half-life of the inhibitor of the JMJD2 family of histone demethylases. Many methods are available for preparing liposomes, as described in, for example, Szoka et al., Ann. Rev. Biophys. Bioeng., 9, 467 (1980) and U.S. Pat. Nos. 4,235,871, 4,501,728, 4,837,028, and 5,019,369.

When inhibitors of the JMJD2 family of histone demethylases are administered with one or more additional therapeutic agents, including additional inhibitors of the JMJD2 family of histone demethylases or with inhibitors of the LSD1 protein as the additional therapeutic agents, one or more additional therapeutic agents can be coadministered to the mammal. By "coadministering" is meant administering one or more additional therapeutic agents and the inhibitors of the JMJD2 family of histone demethylases sufficiently close in time such that these can enhance the effect of one or more additional therapeutic agents. In this regard, the inhibitors of the JMJD2 family of histone demethylases can be administered first and the one or more additional therapeutic agents can be administered second, or vice versa, to provide for sequential administration. Alternatively, the inhibitors of the JMJD2 family of histone demethylases and the one or more additional therapeutic agents can be administered simultaneously. Inhibitors of the JMJD2 family of histone demethylases and the one or more additional therapeutic agents also can be administered cyclically.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The terms "treat," "prevent," and "inhibit" as well as words stemming therefrom, as used herein, do not necessarily imply 100% or complete treatment, prevention, or inhibition. Rather, there are varying degrees of treatment, prevention, or inhibition of which one of ordinary skill in the art recognizes as having a potential benefit or therapeutic effect. In this respect, the inventive methods can provide any amount of any level of treatment, prevention, or inhibition of a condition associated with, e.g., JMJD2 histone demethylase activity, such as demethylation of histones, in a host. Furthermore, the treatment, prevention, or inhibition provided by the inventive methods can include treatment, prevention, or inhibition of one or more conditions or symptoms of the disease being treated, prevented, or inhibited. Also, for purposes herein, "prevention" or "inhibiting" can encompass delaying the onset of the disease or a symptom or condition thereof.

An "effective amount" refers to a dose that is adequate to prevent, treat, or inhibit a condition associated with, e.g., JMJD2 histone demethylase activity. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the compound selected, method of administration, timing and frequency of administration as well as the existence, nature, and extent of any adverse side-effects that might accompany the administration of a particular compound and the desired physiological effect. For example, the dose of the inhibitor to be administered for treating a condition associated with, e.g., JMJD2 histone demethylase activity, can be about 0.1 mg to about 10 g per day (e.g., 0.5 mg, 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 2 g, 3 g, 4 g, 5 g, 6 g, 7 g, 8 g, 9 g, or ranges of any of the values described herein). The dose of the inhibitor to be administered for preventing a condition associated with, e.g., JMJD2 histone demethylase activity, can be less than the dose for treating such a condition, e.g. about 0.001 mg/kg per day to about 1 mg/kg per day (e.g., 0.001 mg/kg, 0.005 mg/kg, 0.01 mg/kg, 0.05 mg/kg, 0.1 mg/kg, 0.5 mg/kg, 1 mg/kg, or ranges of any of the values described herein). Alternatively or in addition, the dose of inhibitor to be administered for prevention or treatment can be 0.001 mg/kg to 200 mg/kg per day (e.g., 0.01 mg/kg, 0.05 mg/kg, 0.1 mg/kg, 0.5 mg/kg, 1 mg/kg, 5 mg/kg, 10 mg/kg, 50 mg/kg, 100 mg/kg, 150 mg/kg, or ranges of any of the values described herein). It will be appreciated by one of skill in the art that various diseases or disorders could require prolonged treatment involving multiple administrations, perhaps using inhibitors of the JMJD2 family of histone demethylases in each or various rounds of administration.

The following examples further illustrate the invention but, of course, should not be construed as in any way limiting its scope.

EXAMPLE 1

This example demonstrates the inhibition of members of the JMJD2 family of histone demethylases by siRNA, in accordance with an embodiment of the invention.

The antibodies and primers used in this study are described in Liang, Vogel, Narayanan & Kristie, Nature Med., 2009, 15:1312-1317, incorporated herein by reference.

siRNA sequences used were

```
                                    (SEQ ID NO: 1)
    JMJD2A:  GAACCGACCUCCAAACUUU (SEQ ID NO: 2)
    JMJD2B:  GCAGGCACCGUCCACAUUU
```

Figure 1:
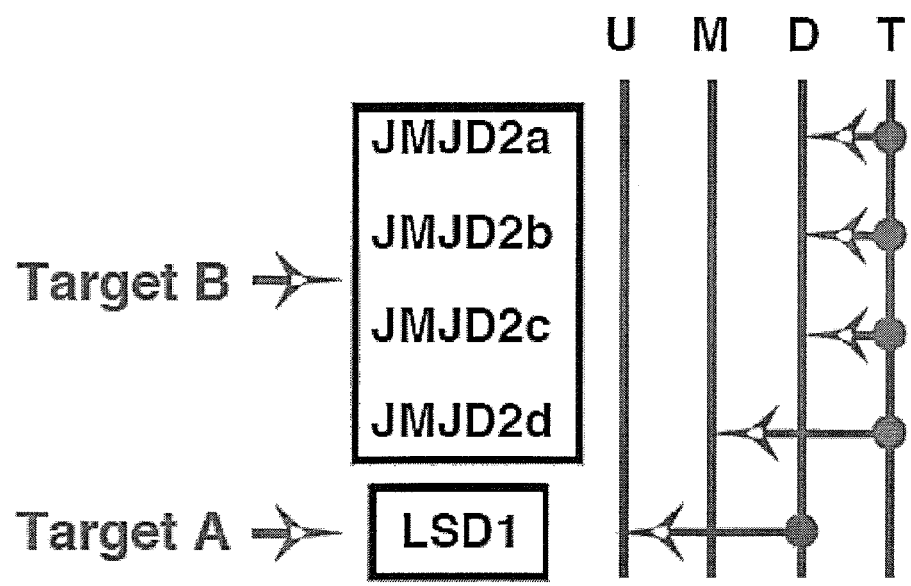
FIG. 1 shows histone H3-Lysine 9 demethylases and their respective target specificity. LSD1 can demethylate di- (D) and mono- (M) methyl-lysine to the unmethylated state (U). In contrast, most members of the JMJD2 family convert a tri-methyl-lysine (T) to di-methyl.
Figure 3:
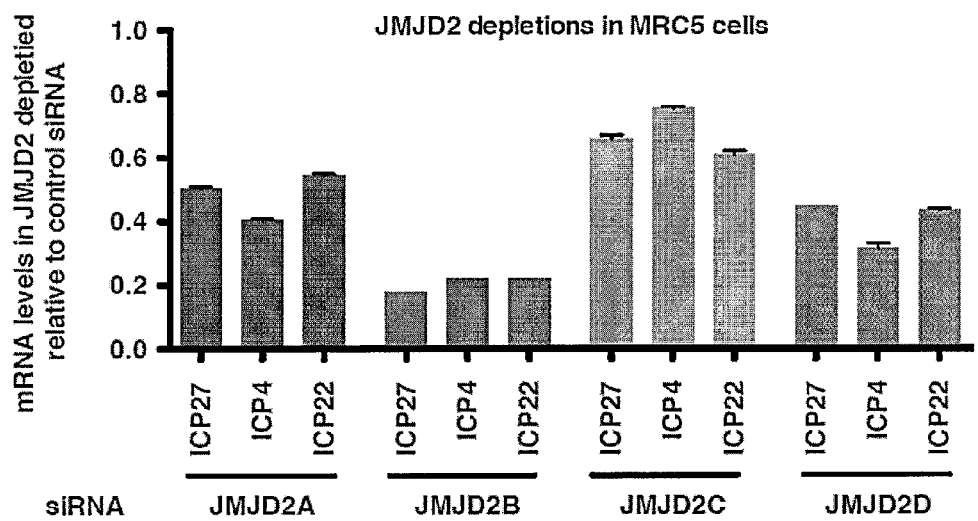
FIG. 3 is a bar graph, showing the impact of depletion of members of the JMJD2 family on HSV IE gene expression in MRC5 cells. In accordance with embodiments of the invention, the viral IE mRNA levels decrease after administration of siRNA directed against the JMJD2 family of histone demethylases.
Figure 4:
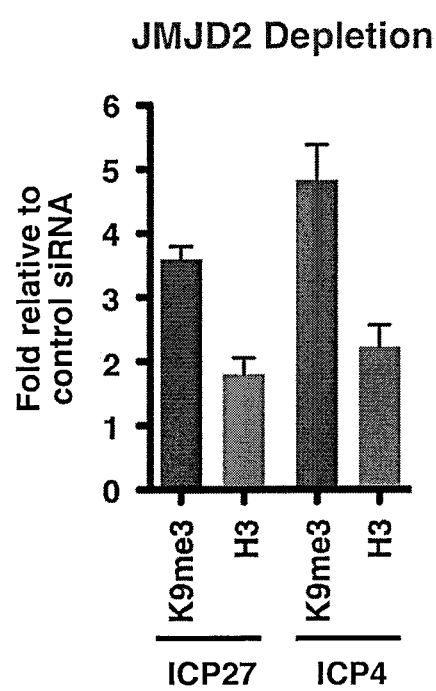
FIG. 4 shows a bar graph of levels of tri-methylated lysine 9 of histone H3 or total histone H3 associated with viral IE promoters for ICP27 and ICP4 in the presence of JMJD2 siRNA. In accordance with an embodiment of the invention.

```
                                    (SEQ ID NO: 3)
    JMJD2C:  GAGAGGACAUCUACACUUU (SEQ ID NO: 4)
    JMJD2D:  CUGGAAGAACCGCAUCUAUAA.
``` siRNA depletion of JMJD2 family members reduces HSV-1 IE gene expression. FIGS. 2A and 2B show herpes simplex virus Immediate Early genes ICP27 and ICP4 mRNA levels after administration of siRNA directed against JMJD2a (A), JMJD2b (B), JMJD2c (C), JMJD2d (D), and combinations of these. Hela cells were transfected with 1 nmol of siRNAs against the indicated JMJD2 histone demethylase or control siRNA for 48 hrs. Cells were subsequently infected with 0.1 PFU/cell HSV-1 for 2 hrs. Total RNA was extracted, reverse-transcribed, and cDNAs were quantitated by qPCR using primers to relevant genes of interest. FIG. 3 is a bar graph, showing the impact of depletion of members of the JMJD2 family on HSV IE gene expression in MRC5 cells, using similar methods.

siRNA depletion of JMJD2 proteins results in accumulation of repressive chromatin on HSV-1 IE promoters (FIG. 4). Hela cells were transfected with siRNAs against JMJD2 family demethylases. Forty-eight hours later, cells were infected with 0.1 pfu/cell of HSV-1 for 3 hrs. Standard Chromatin-Immunoprecipitation procedures were preformed (Liang, Vogel, Narayanan, Peng & Kristie, 2009, Nature Med 15:1312-17) to determine the levels of total histone H3 or tri-methylated histone H3 associated with the indicated viral IE promoters.

Figure 5:
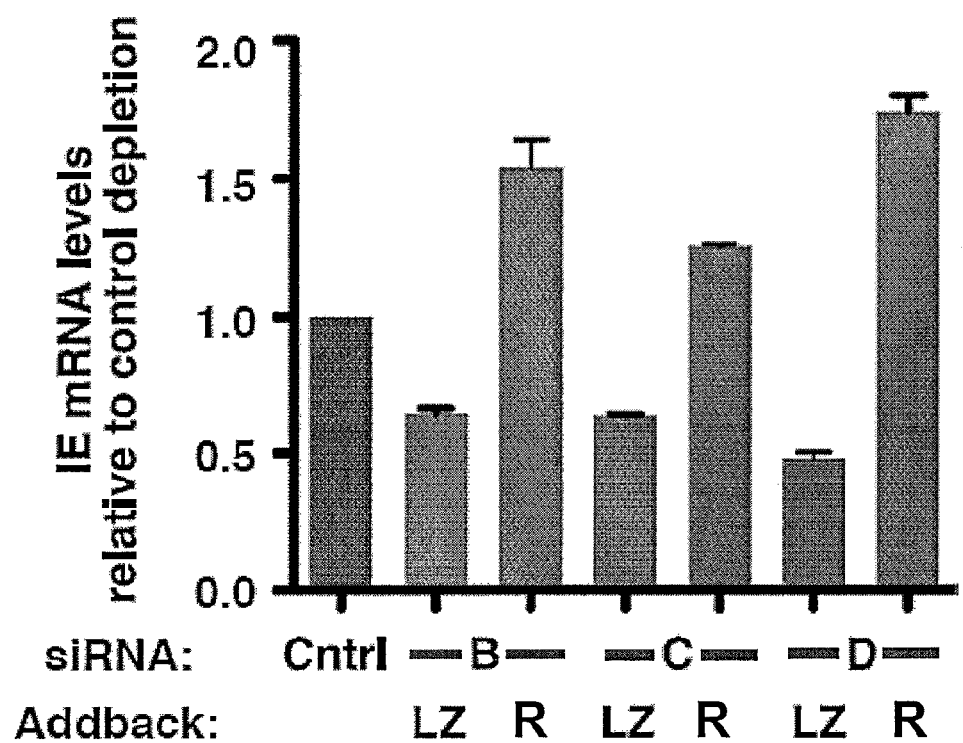
FIG. 5 is a bar graph showing recovery of herpes simplex virus Immediate Early gene ICP4 mRNA levels after administration of control siRNA (Cntrl) or siRNA directed against JMJD2b (B), JMJD2c (C), or JMJD2d (D). Post depletion, cells were transfected with plasmids expressing control LacZ (bars labeled "LZ") or siRNA resistant JMJD2s (bars labeled "R"). In accordance with embodiments of the invention, depletion of JMJD2s decrease viral IE mRNA expression and viral IE expression is recovered upon expression of siRNA resistant JMJD2 proteins.

FIG. 5 shows recovery of HSV-1 IE gene expression by siRNA resistant JMJD2 family members. Herpes simplex virus Immediate Early gene ICP4 mRNA levels were measured after administration of control siRNA or siRNA directed against JMJD2s (sequences provided above). Post depletion, cells were transfected with plasmids expressing control LacZ or siRNA resistant JMJD2s. Plasmids expressing siRNA resistant JMJD2 mRNAs were generated by site-specific mutagenesis according to standard protocols. Cells were subsequently infected with 0.1 PFU/cell HSV-1 for 2 hrs. Total RNA was extracted, reverse-transcribed, and cDNAs were quantitated by qPCR using primers to viral IE genes.

Inhibition of the activity of the JMJD2 demethylase family results in reduced accumulation of viral IE mRNAs and decreased viral yields during lytic infection of cells. siRNA depletion analyses demonstrate that all four members of the JMJD2 family contribute to viral IE gene transcription in a synergistic manner.

EXAMPLE 2

This Example demonstrates the inhibition of the catalytic activity of members of the JMJD2 family of histone demethylases by a small molecule inhibitor that blocks viral immediate early gene expression during lytic infection with HSV-1 and reactivation from latency, in accordance with an embodiment of the invention.

Antibodies and primers used are described in Liang, Vogel, Narayanan & Kristie, Nature Med., 2009, 15:1312-1317.

Figure 6:
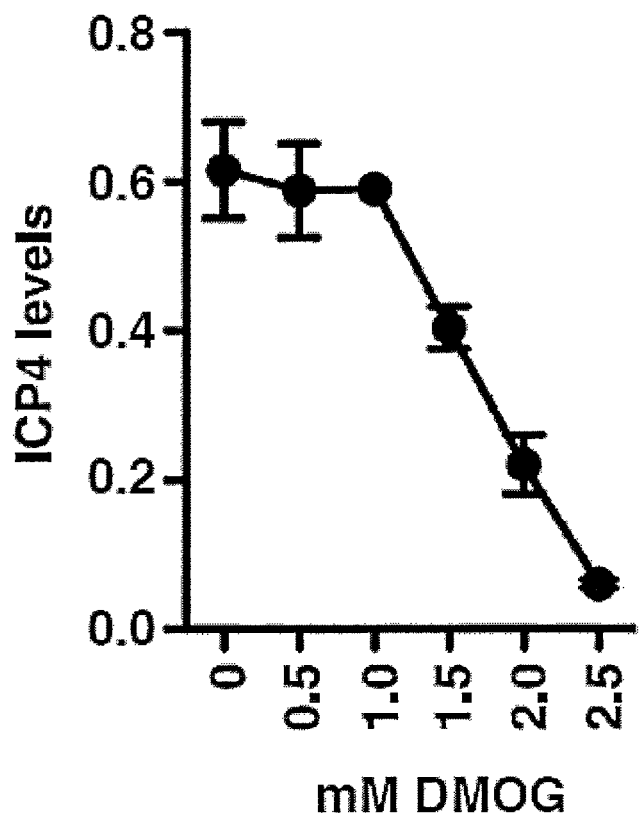
FIG. 6 is a line graph, showing herpes simplex virus ICP4 protein levels at increasing concentrations of N-methoxy-oxoacetyl-glycine methyl ester (dimethyloxalylglycine, or DMOG). In accordance with an embodiment of the invention, the viral ICP4 protein level decreases as the concentration of DMOG increases.

HSV-1 IE protein levels of ICP4 decrease in cells infected in the presence of DMOG. HeLa cells were infected with HSV-1 at 0.1 PFU/cell for 3 hrs in the presence of increasing concentrations of DMOG. Cells were harvested and the levels of viral IE proteins (ICP4 shown) were determined by quantitative western blot analyses. As the concentration of DMOG is increased, the levels of ICP4 decrease (FIG. 6).

Figure 7:
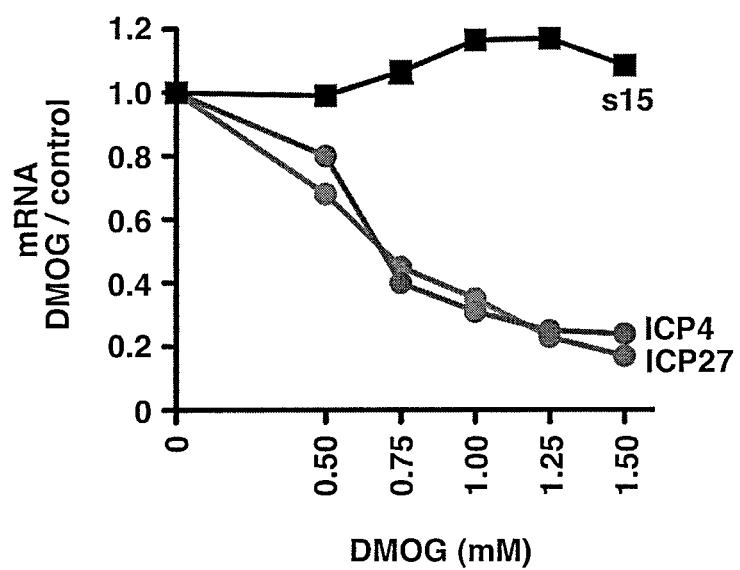
FIG. 7 shows a line graph of HSV-1 IE mRNA levels in cells infected in the presence of DMOG. In accordance with an embodiment of the invention, the HSV-1 mRNA levels of ICP4 and ICP27 decrease with increasing concentration of DMOG, whereas control mRNA (s15) does not.

HSV-1 IE mRNA levels of ICP4 and ICP27 decrease in cells infected in the presence of DMOG. Human foreskin fibroblast (HFF) cells were infected with HSV-1 at 0.1 PFU/cell for 3 hrs in the presence of increasing concentrations of DMOG. Cells were harvested and the levels of viral IE (ICP4, ICP27) and cell control (s15) mRNAs were assessed by qRT-PCR. As the concentration of DMOG is increased, the mRNA levels of ICP4 and ICP27 decrease, whereas that of the control mRNA (s15) does not (FIG. 7).

Figure 8:
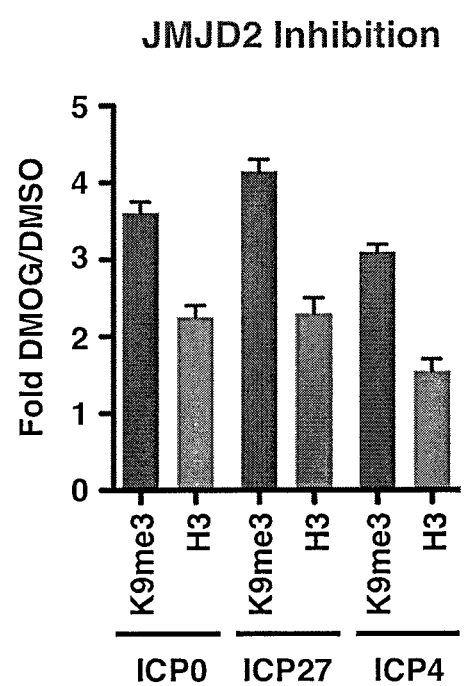
FIG. 8 shows a bar graph of levels of tri-methylated histone H3 or total histone H3 associated with viral IE promoters for ICP0, ICP27, and ICP4 in the presence of DMOG. In accordance with an embodiment of the invention.

DMOG inhibition of JMJD2 proteins results in accumulation of repressive chromatin on HSV-1 IE promoters (FIG. 8). Hela cells were pretreated with 2 mM DMOG for 4 hours prior to infection. Cells were infected with 0.1 pfu/cell of HSV-1 for 3 hrs. Standard Chromatin-Immunoprecipitation procedures were preformed (Liang, Vogel, Narayanan, Peng & Kristie, 2009, Nature Med 15:1312-17) to determine the levels of total histone H3 or tri-methylated histone H3 associated with the indicated viral IE promoters.

Figure 9:
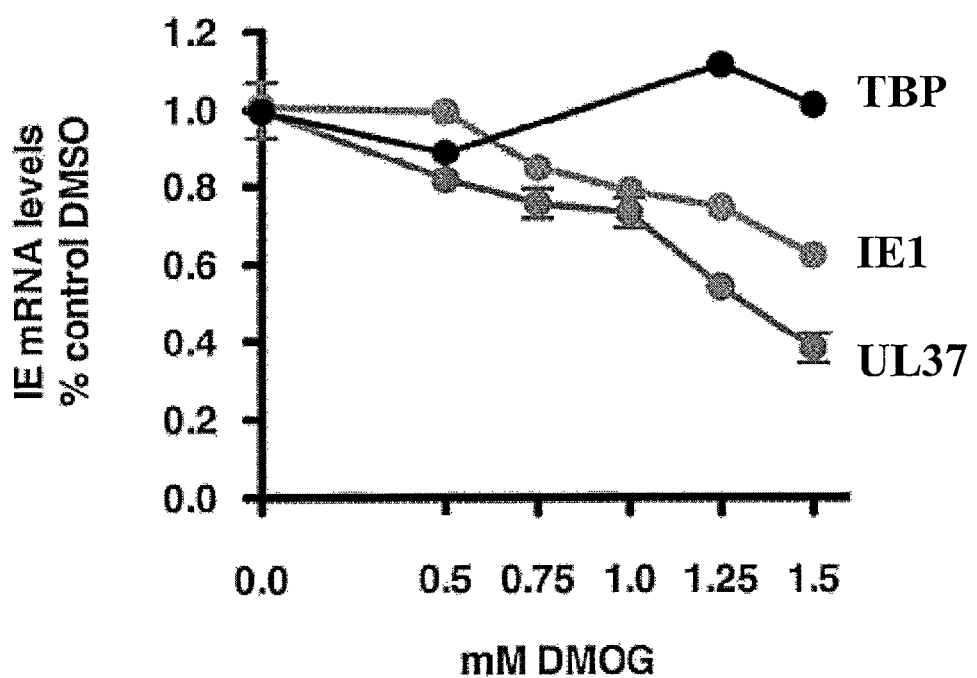
FIG. 9 is a line graph of cytomegalovirus (CMV) IE gene expression (IE1 and UL37) and control TBP in the presence of increasing concentrations of DMOG. In accordance with an embodiment of the invention, the CMV mRNA levels of IE1 and UL37 decrease with increasing concentration of DMOG, whereas control mRNA (Tata Binding Protein, TBP) does not.

CMV IE gene expression (IE1 and UL37) and control TBP (Tata binding Protein) in the presence of increasing concentrations of DMOG were also studied (FIG. 9). HFF were pretreated with the indicated concentration of DMOG for 3.5 hrs and infected with CMV for 4 hrs. Total RNA was extracted, reverse-transcribed, and cDNAs were quantitated by qPCR using primers to viral IE genes or control genes. As the concentration of DMOG is increased, the mRNA levels of IE7 and UL37 decrease, whereas that of the control mRNA (TBP) does not.

Figure 10:
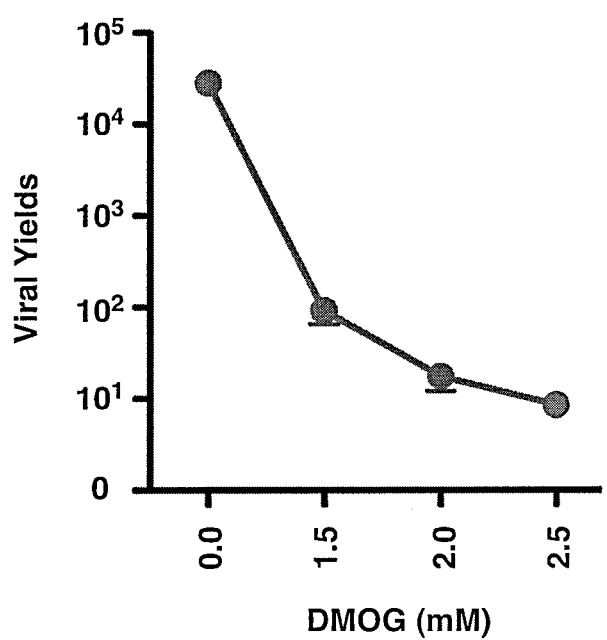
FIG. 10 shows a line graph of HSV-1 lytic viral yields in the presence of DMOG. In accordance with an embodiment of the invention, viral yields decrease with increasing concentration of DMOG.

HSV-1 lytic viral yields decrease in the presence of DMOG (FIG. 10). HFF cells were pretreated with DMSO control or JMJD2 inhibitor DMOG for 5 hrs and infected with 0.1 pfu/cell of HSV-1 for 24 hrs in the presence of DMSO or DMOG. The yield of infectious virus derived from each treatment were determined by tittering on Vero cells according to standard procedures.

Figure 11:
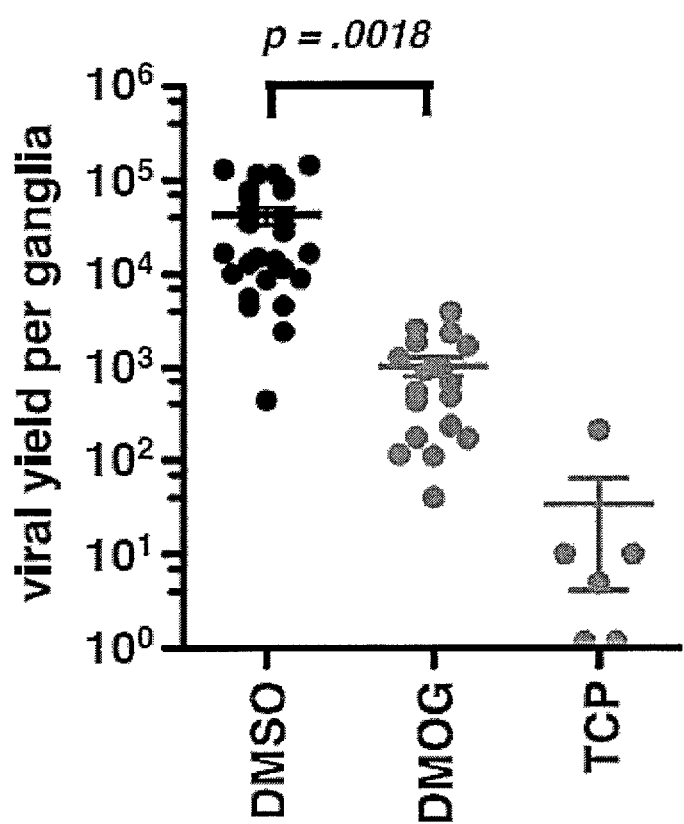
FIG. 11 shows a dot plot of viral yields from explanted latently infected ganglia in the presence of control vehicle DMSO, DMOG, or tranylcypromine (TCP). In accordance with an embodiment of the invention, the viral yield decreases after administration of DMOG or an inhibitor of the LSD1 protein, TCP.

Viral yields decrease from HSV-1 latently infected ganglia explanted in the presence of LSD1 or JMJD2 inhibitors (FIG. 11). Balb/c mice were infected with $5 \times 10^6$ PFU HSV-1 (strain F) per eye after corneal scarification. Latently infected mice were sacrificed 45 days post clearance of the primary infection and trigeminal ganglia were rapidly explanted into culture in the presence of 2 mM DMOG, 2 mM TCP, or control (DMSO or ACV, acyclovir) for 48 hours. Post explant incubation, the ganglia were homogenized and briefly sonicated. The reactivated viral yield of each ganglia was determined by titering the clarified supernatant on Vero cells. Statistical comparisons were made using Wilcoxon signed rank test (paired ganglia) with a statistical significance of <0.05. Each data point was the result of a single ganglia divided and treated in the presence and absence of DMSO and DMOG or DMSO and TCP. Therefore, a Wilcoxon signed rank test was used to assess differences between each treated and untreated sample. The significant difference between DMSO control and DMOG was p=0.0018. This test used an exact p-value for small sample sizes with an a level of 0.05. n=20. Analyses were made using Prism (V5.0a) and are expressed as the mean+/−s.e.m. No viral yields are obtained in the presence of ACV.

Figure 12:
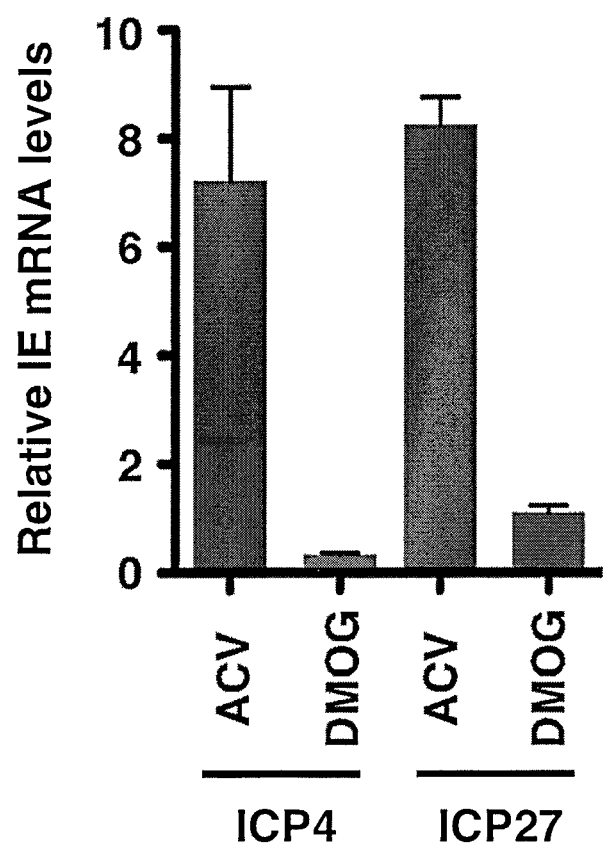
FIG. 12 shows a bar graph of the relative mRNA levels in HSV-1 latently infected trigeminal ganglia explanted in the presence of either acyclovir (ACV) or DMOG at 7 hours post explant. Total RNA was isolated and subjected to reverse transcription. The resulting cDNAs were analyzed for viral Immediate Early ICP4 and ICP27 mRNAs relative to an infected cell standard by nested or qPCR. In accordance with an embodiment of the invention, DMOG reduces the levels of viral mRNAs in explanted/reactivated ganglia.

IE gene transcription is repressed in explanted latently infected sensory ganglia in the presence of DMOG (FIG. 12). Total RNA was extracted from ganglia of latently infected mice explanted in the presence of control ACV or DMOG for 7 hours. Random primed cDNA was produced from total RNA using RNAqueous-4PCR and RETROscript (Ambion, Austin, Tex., USA) according to the manufacturer's recommendations. cDNAs were quantitated by nested PCR or qPCR using primers specific for the HSV-1 ICP4 and ICP27 IE mRNAs.

Given the chemical mechanism by which LSD1 functions, the protein is only capable of removing mono- and dimethylation. As repressive tri-methylated H3-Lys9 is readily detected early in viral infection, an additional histone demethylase(s) with the complementing activity is required in cooperation with LSD1 to effectuate viral replication.

Inhibition of JMJD2 activities results in reduced viral IE mRNAs and viral yield during reactivation from latency demonstrating that inhibition of JMJD2 activities blocks viral reactivation from latency.

EXAMPLE 3

This example demonstrates the inhibition of the catalytic activity of members of the JMJD2 family of histone demethylases by small molecule inhibitors that block viral immediate early gene expression during lytic infection with HSV-1 and reactivation from latency, in accordance with an embodiment of the invention.

All experiments were performed as described in Liang et al., Sci. Transl. Med. 5, 167ra5 (2013). N-(3-(dimethylamino)propyl)-4-(8-hydroxyquinolin-6-yl)benzamide (designated ML324) has the following characteristics: N-(3-(dimethylamino)propyl)-4-(8-hydroxyquinolin-6-yl) benzamide (1). LC-MS: rt (min)=3.033; $^1$H NMR (400 MHz, DMSO-$d_6$) δ 1.84-1.98 (m, 2H), 2.79 (s, 3H), 2.80 (s, 3H), 3.12 (ddd, J=10.2 Hz, 5.4 Hz and 5.2 Hz, 2H), 3.37 (q, 2H), 7.50 (s, 1H), 7.66 (dd, J=8.2 Hz and 4.3 Hz, 1H), 7.84 (s, 1H), 7.88-7.94 (m, 2H), 7.96-8.02 (m, 2H), 8.50 (d, J=8.2 Hz, 1H), 8.71 (t, J=5.6 Hz, 1H), 8.90 (d, J=4.1 Hz, 1H), 9.34 (brs, 1H); HRMS (ESI) m/z $(M+H)^+$ $C_{21}H_{24}N_3O_2$, 350.1867. found 350.1863.

Figure 13:
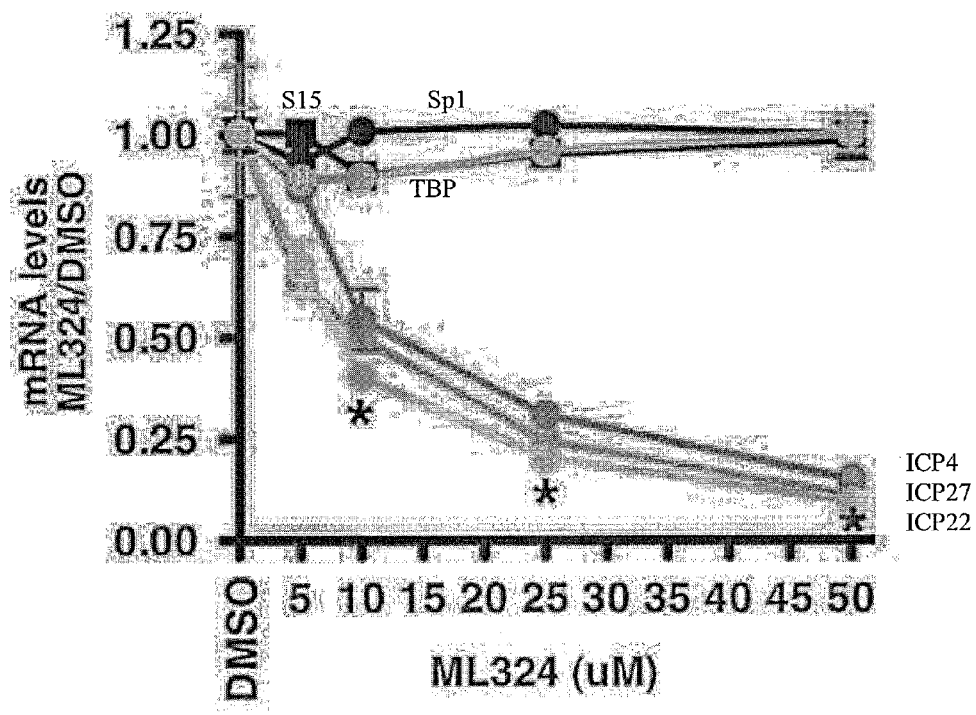
FIG. 13 is a line graph showing viral IE (ICP4, ICP27, and ICP22) and control (S15, Sp1, and TBP) mRNA levels in HFF cells treated with DMSO or the indicated concentrations of ML324 for 3 hours and infected with HSV-1 (0.1 PFU per cell) for 3 hours. *$P<0.0001$, two-way ANOVA with Tukey's post hoc test. Data are means±SEM.
Figure 14:
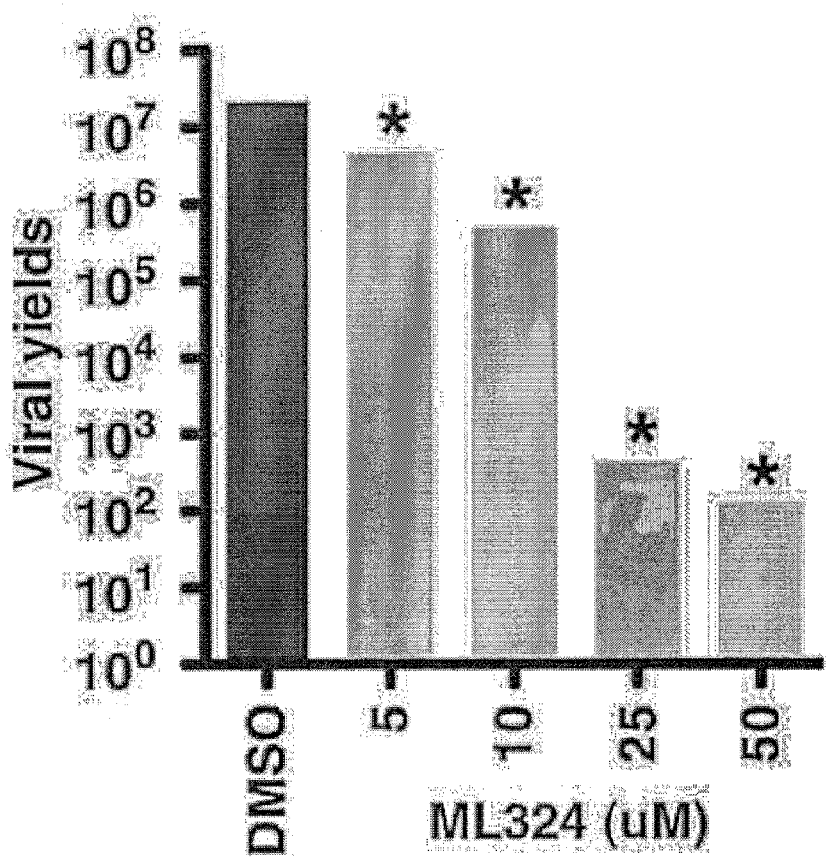
FIG. 14 is a bar graph showing viral yields from HFF cells treated with DMSO or ML324 for 3 hours and infected with HSV-1 (0.1 PFU per cell) for 24 hours in the presence of the drugs. *$P<0.004$, one-way ANOVA with Dunnett's post hoc test. Data are means±SEM.
Figure 15:
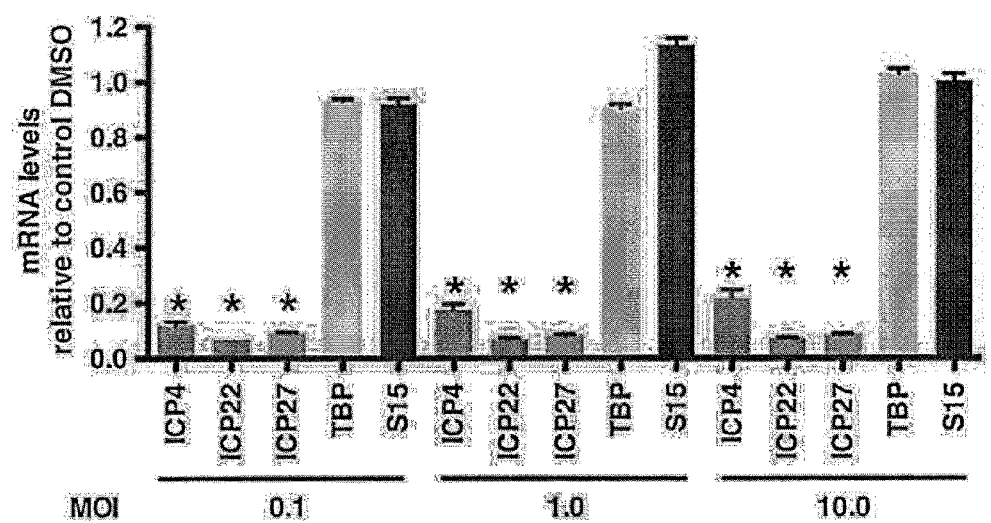
FIG. 15 is a bar graph showing MRC-5 cells treated with DMSO or 50 mM ML324 that were infected with HSV-1 at the indicated multiplicity of infection (MOI). Viral IE and cellular mRNA levels were quantitated at 2 hours after infection. *$P<0.0001$, two-way ANOVA with Tukey's post hoc test. Data are means±SEM.
Figure 16:
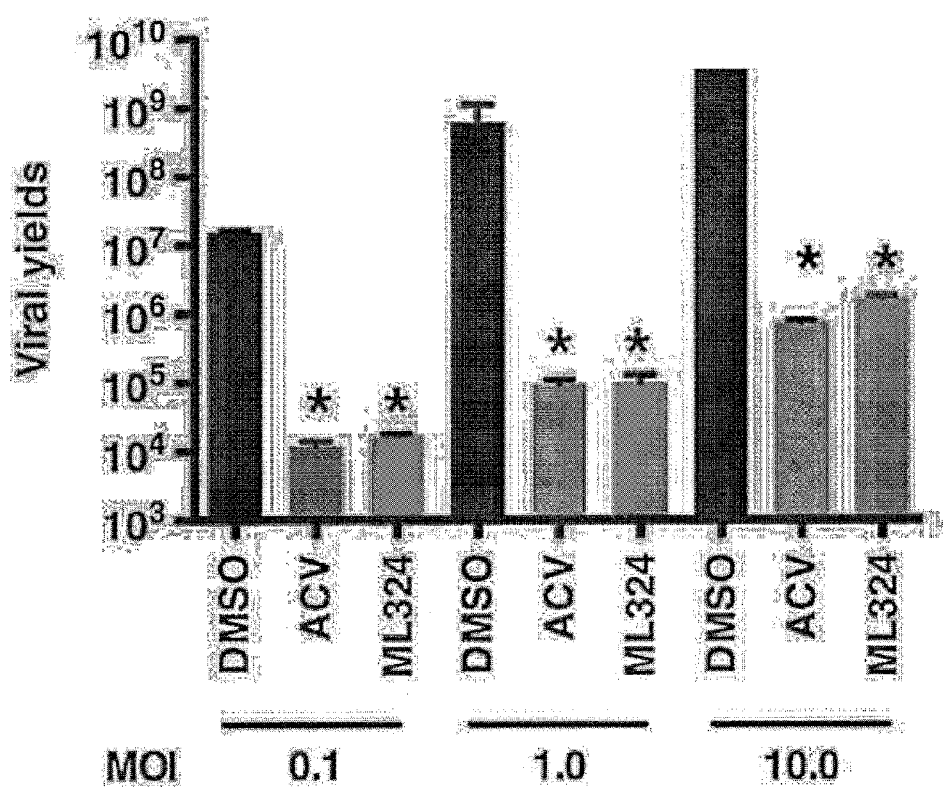
FIG. 16 is a bar graph showing MRC-5 cells treated with DMSO or 50 mM ML324 that were infected with HSV-1 at the indicated MOI. Viral yields were determined at 24 hours after infection. *$P<0.0001$, two-way ANOVA with Tukey's post hoc test. Data are means±SEM.
Figure 17:
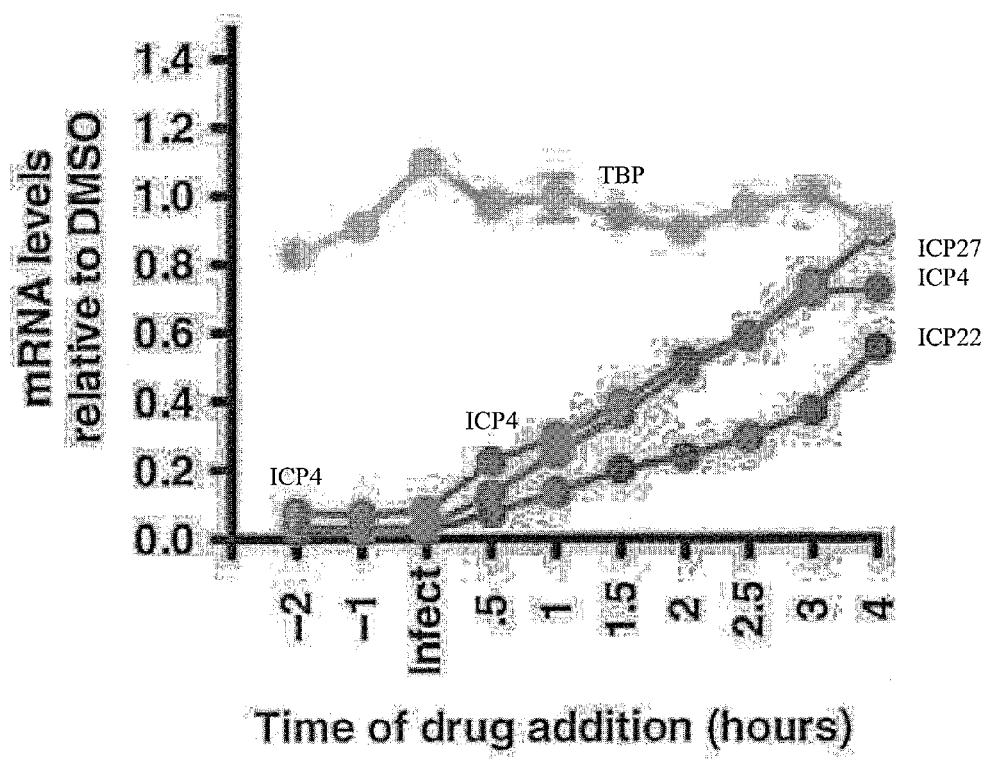
FIG. 17 is a line graph showing MRC-5 cells that were treated with DMSO or ML324 at the indicated time relative to infection with HSV-1 (1.0 MOI). Viral and cellular mRNA levels were determined at 4 hours after infection. Data are means±SEM.

ML324 was highly effective in reducing IE gene expression with an $IC_{50}$~10 mM (FIG. 13). ML324 was ~75-fold more efficient than DMOG. Additionally, ML324 (i) reduced viral yields in a dose-dependent manner (~5 logs at 50 mM, FIG. 14); (ii) blocked viral IE gene transcription and reduced viral yields when cells were infected at high multiplicity of infection (MOI; FIGS. 15 and 16); and (iii) suppressed IE gene transcription, even when added at times after infection (>50% reduction at 2 hours after infection; FIG. 17). As further evidence for the efficacy of ML324, cells were infected with HSV to allow for a productive cycle of infection, followed by treatment with DMSO, ACV, or ML324. ML324 markedly suppressed the formation of HSV plaques (Table 1) and the spread of infection to adjacent cells as visualized by immunofluorescence staining for the HSV DNA replication protein UL29.

TABLE 1

Plaque assay of Vero cells infected with HSV-1 at the indicated MOI for 12 hours, followed by the addition of DMSO, ACV (100 mM), or ML324 (50 mM) for 48 hours.

| | # Plaques | |
| --- | --- | --- |
| MOI | .001 | .01 |
| DMSO | >110 | >>>* |
| ACV | 1 | 8 |
| ML324 | 0 | 2 |

*Indistinguishable plaques

Figure 18:
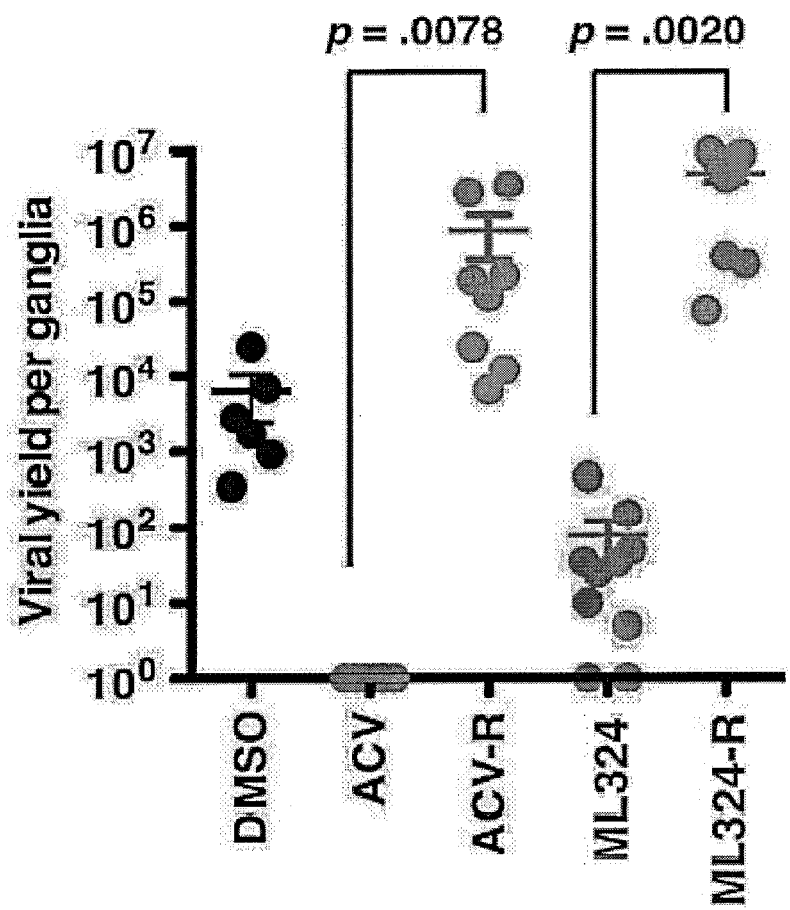
FIG. 18 is a dot plot showing latently infected ganglia that were explanted in the presence of DMSO, ACV (100 mM), or ML324 (50 mM) for 48 hrs. Viral yields were determined from one half of each ganglia at 48 hrs (DMSO, ACV, ML324) and from the other half of each ganglia after drug reversal for an additional 72 hrs (ACV-R, ML324-R) [Wilcoxon matched pairs signed rank test, ACV vs ACV-R n=8, ML324 vs ML324-R n=10]. Data are means±SEM.
Figure 19:
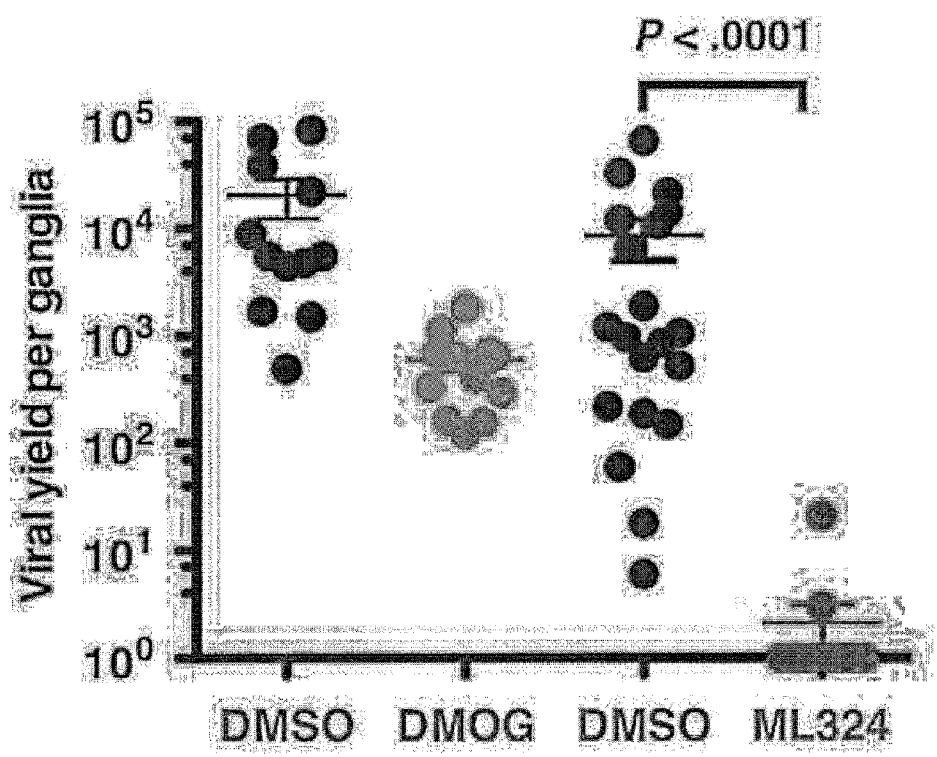
FIG. 19 is a dot plot showing viral yields from HSV-1 latently infected trigeminal ganglia that were explanted in the presence of DMSO, or 2 mM DMOG or 50 mM ML324 for 48 hours (DMSO versus DMOG: P=0.0015, Wilcoxon matched-pairs signed rank test; n=12; DMSO versus ML324: $P<0.0001$; n=20). Data are means±SEM.
Figure 20:
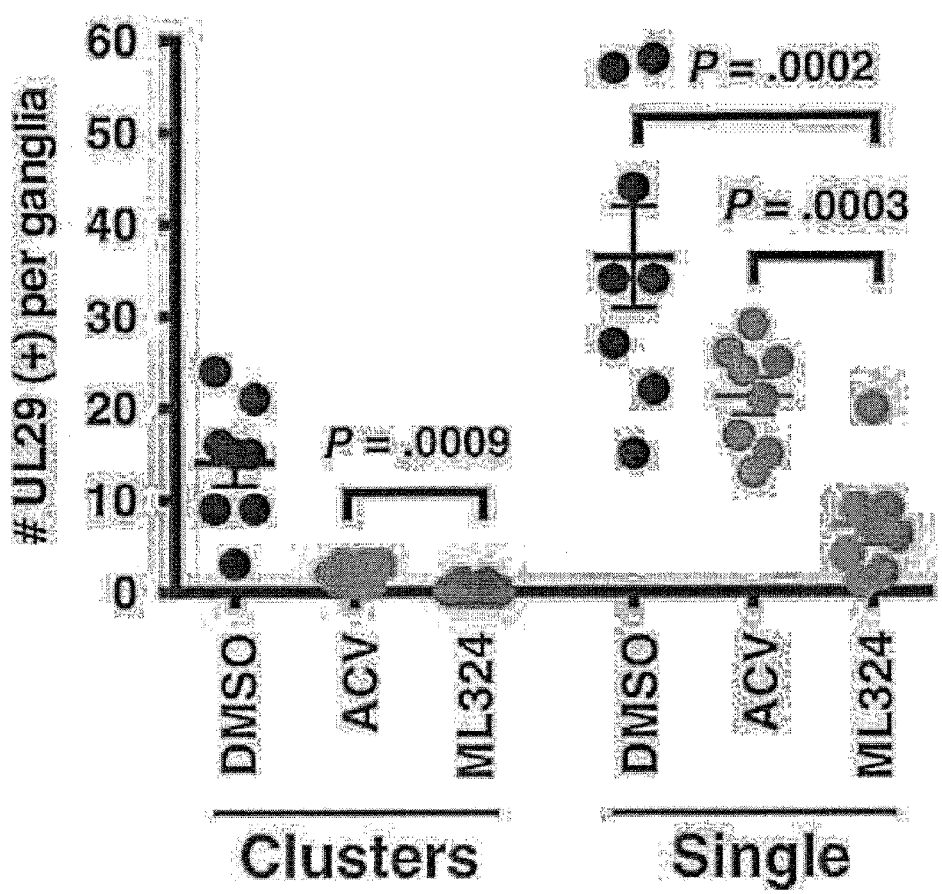
FIG. 20 is a dot plot showing latently infected trigeminal ganglia that were explanted in the presence of DMSO, 100 mM ACV, or 50 mM ML324 for 48 hours. The total number of UL29+ neurons per ganglia is graphed, representing the number of neurons undergoing viral reactivation. Data are means±SEM.
Figure 21:
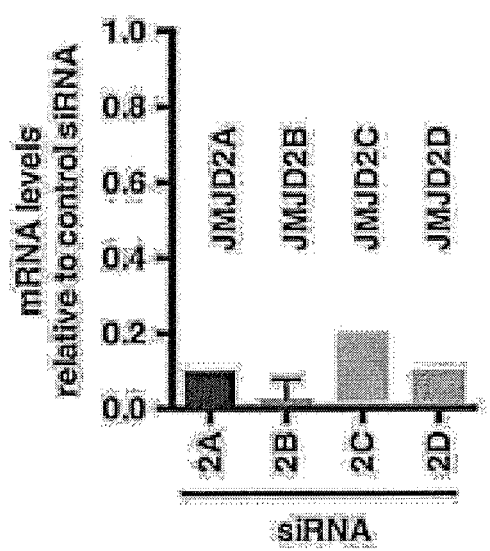
FIG. 21 is a bar graph showing JMJD2 mRNA levels in the homologous siRNA-transfected cells. HeLa cells, depleted of JMJD2A, JMJD2B, JMJD2C, and JMJD2D, were infected with HSV-1 [0.1 plaque-foaming unit (PFU) per cell] for 2 hours. mRNA levels are relative to the levels in control siRNA-transfected cells. Data are reflective of two independent experiments and represented as means±SEM.
Figure 22:
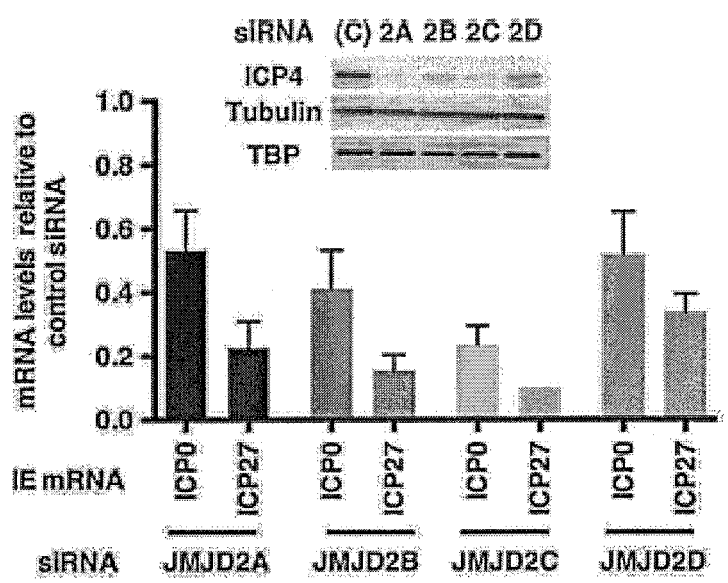
FIGS. 22 and 23 are bar graphs showing mRNA levels HSV IE (ICP0 and ICP27) and cellular control (S15 and TBP) mRNA levels in JMJD2-depleted cells. HSV IE ICP4 protein and cellular controls (tubulin, TBP, and Western blot) in cells transfected with control or JMJD2 siRNAs. HeLa cells, depleted of JMJD2A, JMJD2B, JMJD2C, and JMJD2D, were infected with HSV-1 [0.1 plaque-forming unit (PFU) per cell] for 2 hours. mRNA levels are relative to the levels in control siRNA-transfected cells. Data are reflective of two independent experiments and represented as means±SEM.
Figure 23:
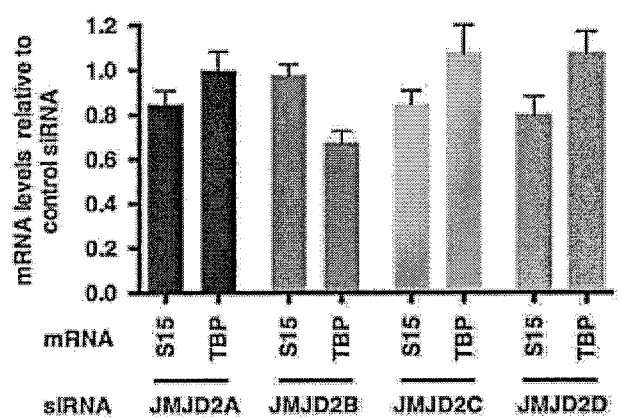
Figure 24:
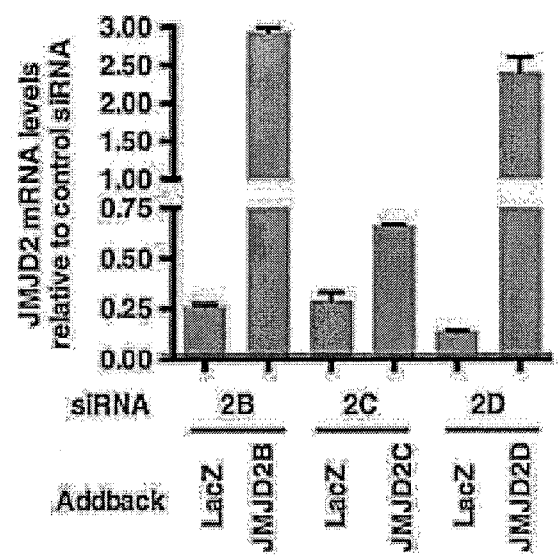
FIGS. 24 and 25 are bar graphs showing cells expressing control (LacZ) or siRNA-resistant JMJD2B, JMJD2C, orcJMJD2D were transfected with siRNAs to the homologous JMJD2 and infected with HSV-1 (0.1 PFU per cell). mRNA levels of the respective JMJD2 (D) and viral IE ICP4 genes (E) were normalized to cellular S15 and are relative to control siRNA-transfected cells. HeLa cells, depleted of JMJD2A, JMJD2B, JMJD2C, and JMJD2D, were infected with HSV-1 [0.1 plaque-forming unit (PFU) per cell] for 2 hours. mRNA levels are relative to the levels in control siRNA-transfected cells. Data are reflective of two independent experiments and represented as means±SEM.
Figure 25:
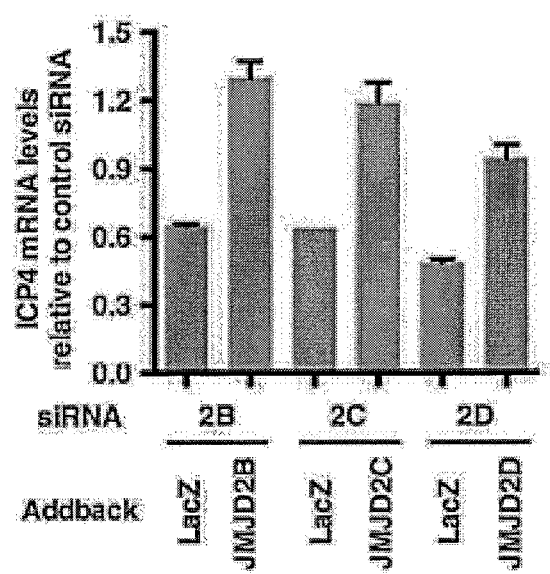
Figure 26:
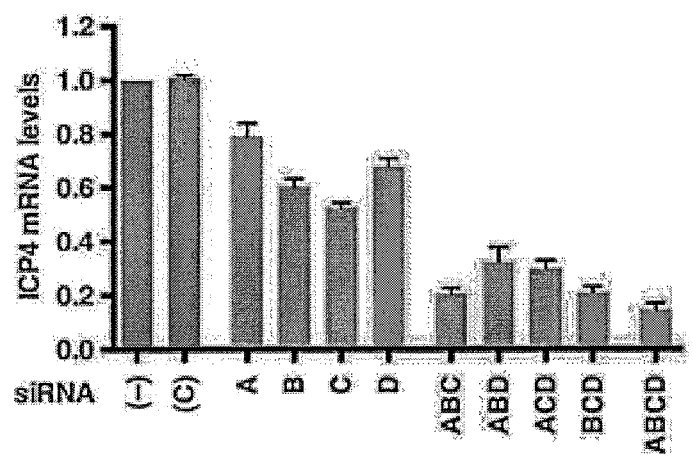
FIGS. 26 and 27 are bar graphs showing HeLa cells were transfected with 1 nM of control, individual JMJD2, or combinations of JMJD2 siRNAs, followed by infection with HSV-1 (0.1 PFU per cell) for 2 hours. mRNA levels of each JMJD2, viral IE (ICP4 and ICP27), and cellular controls [glyceraldehyde-3-phosphate dehydrogenase (GAPDH) and TBP;] are relative to control-transfected cells. (–), no siRNA; (C), control siRNA. Data are reflective of two independent experiments and represented as means±SEM. HeLa cells, depleted of JMJD2A, JMJD2B, JMJD2C, and JMJD2D, were infected with HSV-1 [0.1 plaque-forming unit (PFU) per cell] for 2 hours. mRNA levels are relative to the levels in control siRNA-transfected cells. Data are reflective of two independent experiments and represented as means±SEM.
Figure 27:
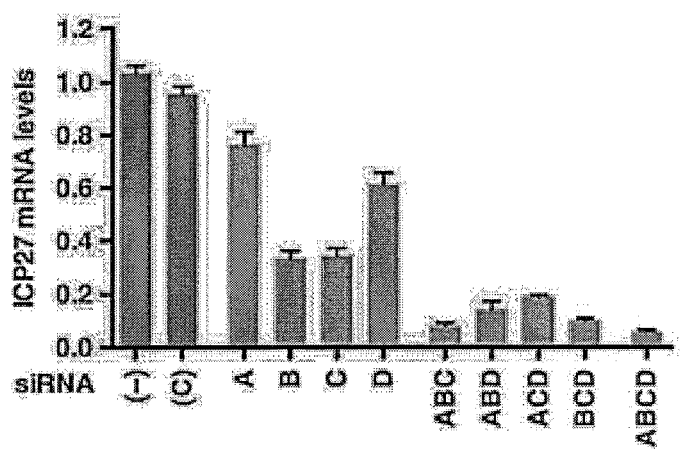
Figure 28:
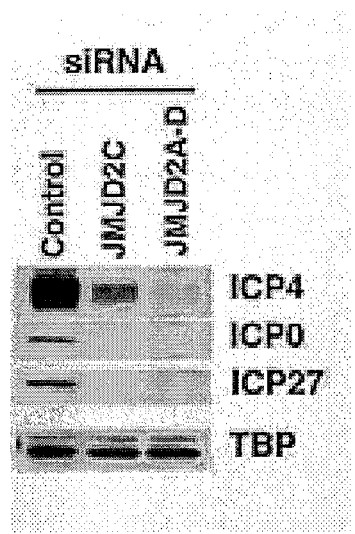
FIG. 28 shows levels of viral IE proteins (ICP4, ICP0, and ICP27) and cellular control TBP were monitored by Western blot. HeLa cells, transfected with siRNAs to JMJD2C or to the four JMJD2s, were infected with HSV-1 (0.1 PFU per cell) for 3 hours. ChIP assays used control immunoglobulin G (IgG), H3K9-me3, or histone H3 antibodies.
Figure 29:
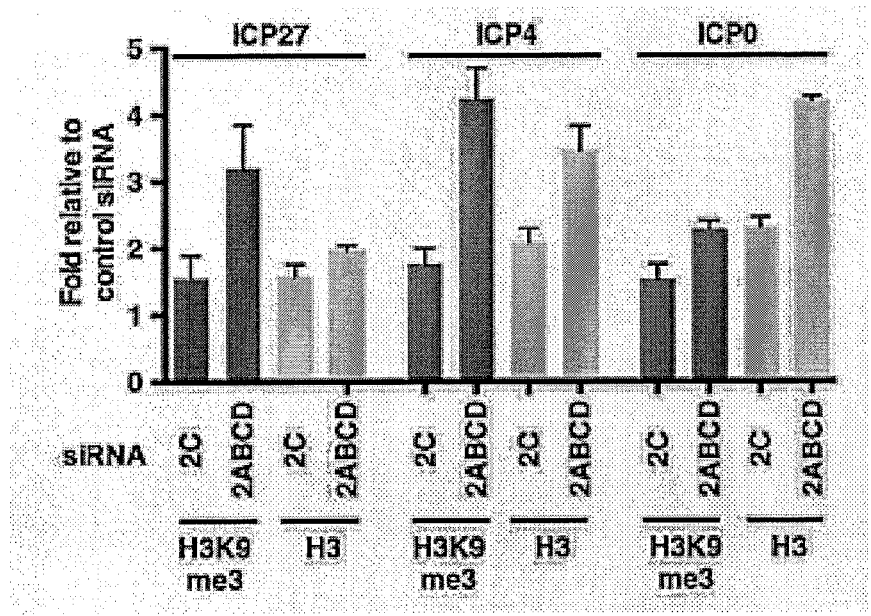
FIGS. 29 and 30 are bar graphs that show levels of H3K9-me3 and histone H3 associated with viral IE promoters (B)
Figure 30:
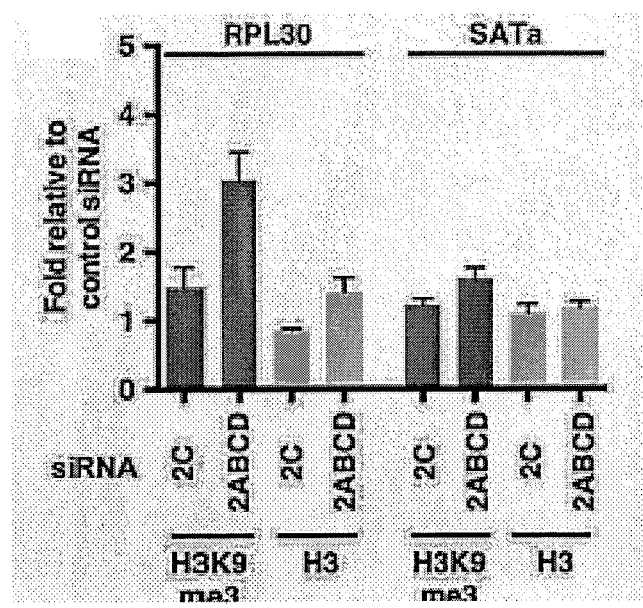

ML324 was next assessed in the mouse sensory ganglia explants model where it was highly effective at reducing the level of viral reactivation at a significantly lower concentration (4.5-log reduction, 50 mM, P<0.0001) than DMOG (~1.5-log reduction, 2 mM, P=0.0015) (FIG. 19). Furthermore, ML324 suppressed the primary viral reactivation events as determined by immunofluorescence staining of explanted ganglia sections (FIG. 20). Ganglia treated with DMSO exhibited viral lytic gene (UL29) expression in isolated neurons and in clusters of neurons and support cells (112 clusters in 48 ganglia sections), illustrating the spread of the reactivated viral infection in the ganglia. ACV-treated ganglia exhibited a reduced number of UL29+ cell clusters (15 clusters in 48 ganglia sections) and isolated neurons (primary reactivating events) relative to DMSO. ML324-treated ganglia exhibited the most significant reduction in UL29+ cell clusters (2 clusters in 48 ganglia sections) and isolated UL29+ neurons relative to both DMSO (P=0.0002) and ACV (P=0.0003) (FIG. 20). Reduction in reactivation by ML324 was not due to the inability of the ganglia to support viral replication as demonstrated by robust viral replication after ML324 withdrawal (FIG. 18).

EXAMPLE 4

This example demonstrates that additional compounds inhibit JMJD2E histone demethylase, in accordance with an embodiment of the invention.

TABLE 2

All Compounds synthesized at NCGC. $IC_{50}$ values were measured using the AlphaLISA ® assay protocol (Beaudet et al., Nat. Meth., 2008, 5, an8-an9) in triplicate. Compound 4 is ML324. Compounds 3, 4, and 6-9 also have an antiviral impact. $IC_{50}$ values are for JMJD2E.

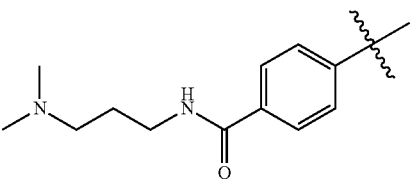

| | R | $IC_{50}$ (µM) |
|---|---|---|
| 1 | NA | 0.84 |
| 2 | NA | 3.07 |
| 3 | | 11.97 |
| 4 | | 0.92 |
| 5 | | 1.62 |

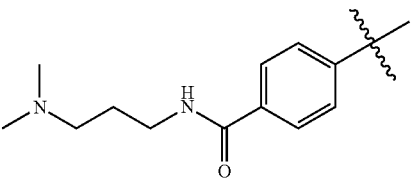 [SMILES: *c1ccc(C(=O)NCCCN(C)C)cc1]

TABLE 2-continued

| # | R | IC₅₀ (µM) |
|---|---|---|
| 6 | *N-methylpiperazinyl* | 4.27 |
| 7 | *piperazinyl-propyl-NH-* | 1.24 |
| 8 | *dimethylamino-methyl-piperidinyl-piperidinyl-* | 0.99 |
| 9 | *dimethylamino-propyl-hexahydropyrimidinyl-* | 1.52 |

TABLE 3

All Compounds synthesized at NCGC. IC₅₀ values were measured using the AlphaLISA ® assay protocol in triplicate. IC₅₀ values are for JMJD2E.

Structure 10-28: 8-hydroxyquinoline-5-carboxylic acid with R group at 3-position

| # | R | IC₅₀ (µM) |
|---|---|---|
| 10 | *N-methylpiperazinyl* | 2.25 |
| 11 | *morpholinyl* | 1.74 |
| 12 | *piperidinyl (NH)* | 1.33 |
| 13 | *4-aminopiperidinyl* | 1.57 |
| 14 | *pyrrolidinyl* | 2.24 |
| 15 | *3-pyrrolidinylamino-* | 1.76 |
| 16 | *3-aminopyrrolidinyl-* | 1.17 |
| 17 | *octahydropyrrolo[3,4-b]pyrrolyl-* | 1.47 |
| 18 | *4-benzylpiperazinyl-* | 4.98 |
| 19 | *4-morpholinophenyl-* | 4.18 |

TABLE 3-continued

All Compounds synthesized at NCGC. IC$_{50}$ values were measured using the AlphaLISA ® assay protocol in triplicate. IC$_{50}$ values are for JMJD2E.

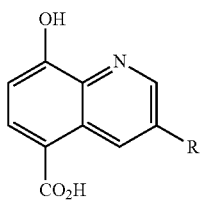

10-28

| | R | IC$_{50}$(μM) |
|---|---|---|
| 20 | 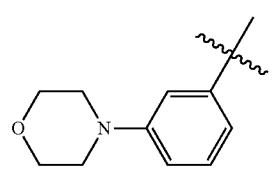 [SMILES: *c1cccc(N2CCOCC2)c1] | 5.11 |
| 21 | 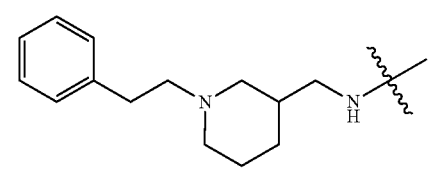 [SMILES: *NCC1CCCN(CCc2ccccc2)C1] | 2.10 |
| 22 | 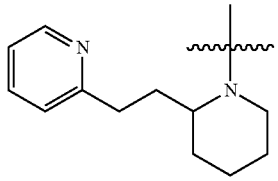 [SMILES: *N1CCCCC1CCc1ccccn1] | 4.66 |
| 23 | 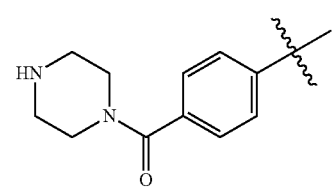 [SMILES: *c1ccc(C(=O)N2CCNCC2)cc1] | 3.61 |

TABLE 3-continued

All Compounds synthesized at NCGC. IC$_{50}$ values were measured using the AlphaLISA ® assay protocol in triplicate. IC$_{50}$ values are for JMJD2E.

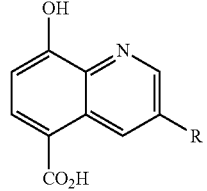

10-28

| | R | IC$_{50}$(μM) |
|---|---|---|
| 24 | 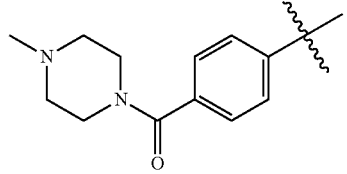 [SMILES: *c1ccc(C(=O)N2CCN(C)CC2)cc1] | 4.63 |
| 25 | 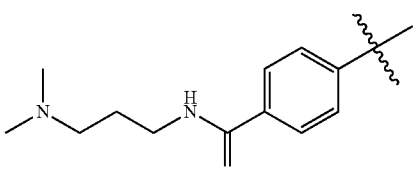 | 1.41 |
| 26 | 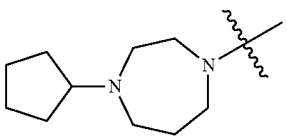 [SMILES: *N1CCCN(C2CCCC2)CC1] | 2.08 |
| 27 | 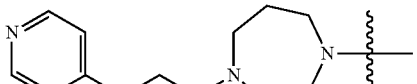 | 1.71 |
| 28 | 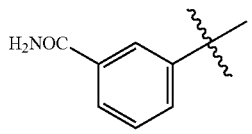 [SMILES: *c1cccc(C(N)=O)c1] | 4.90 |

TABLE 4

Additional compounds. These compounds also have an antiviral impact.

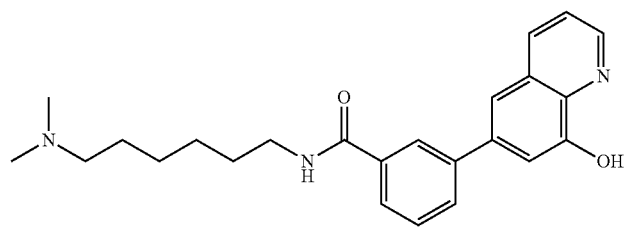 [SMILES: CN(C)CCCCCCNC(=O)c1cccc(-c2cc(O)c3ncccc3c2)c1]

TABLE 4-continued

Additional compounds. These compounds also have an antiviral impact.

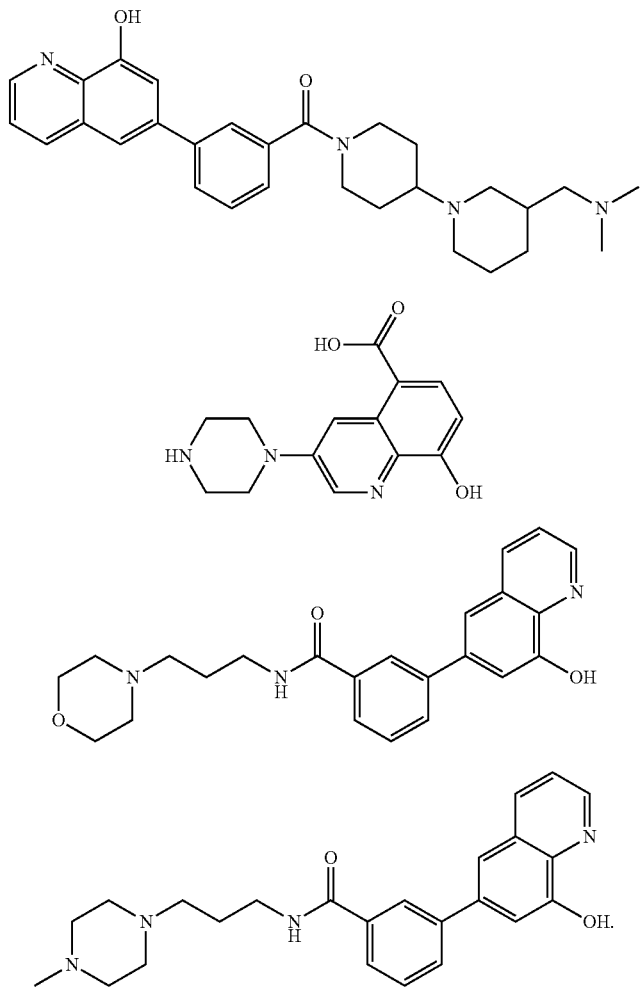

EXAMPLE 5

This example demonstrates additional biological data in FIGS. 21-60, in accordance with embodiments of the invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating herpesvirus infection of a host, the method comprising administering to the host an effective amount of a substance, wherein the substance is an inhibitor of a JMJD2 protein and is a compound of

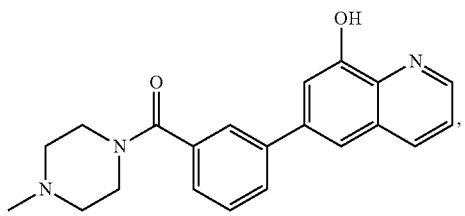

-continued

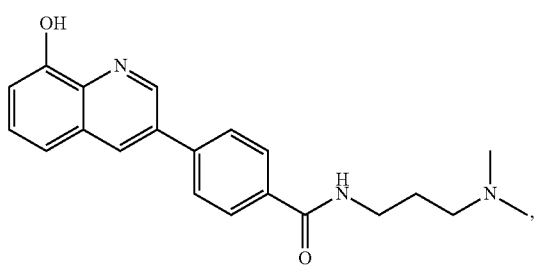

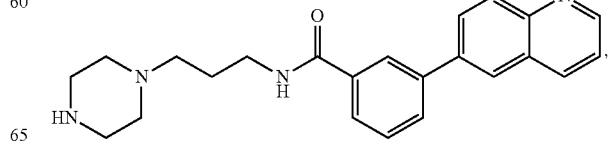

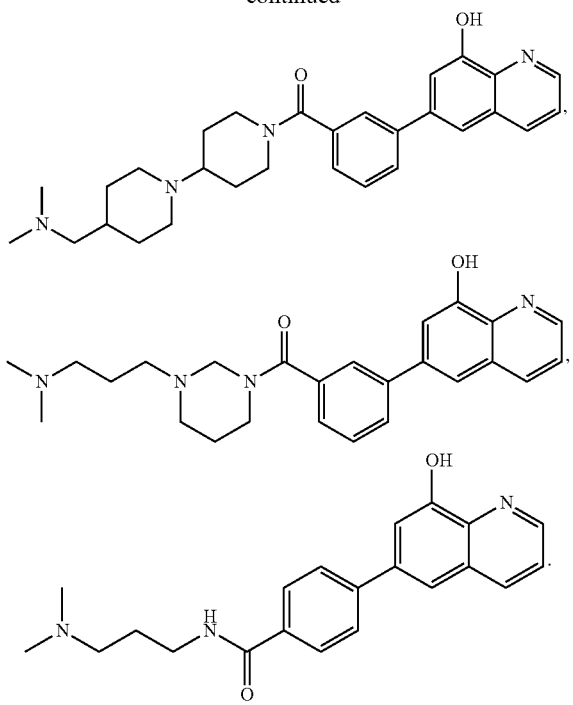

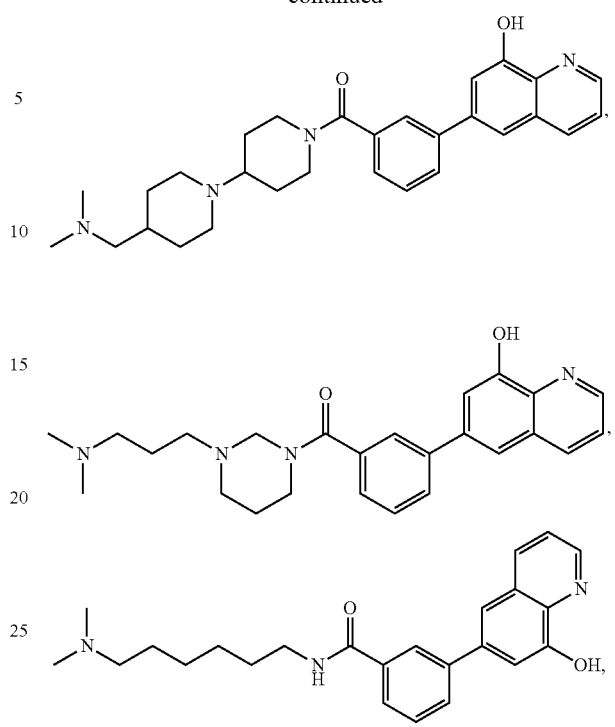

2. A method of inhibiting a member of the JMJD2 family of histone demethylases in a herpesvirus-infected host, the method comprising administering to the host an effective amount of a substance, wherein the substance is a compound of

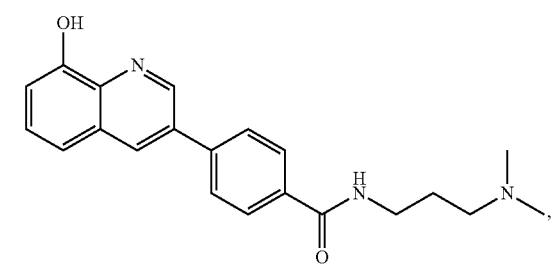

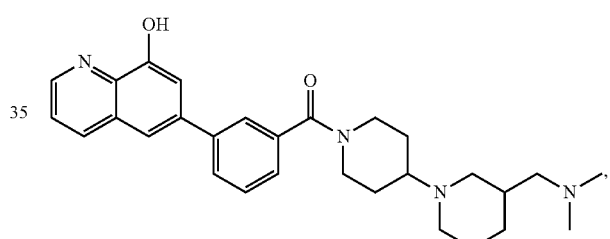

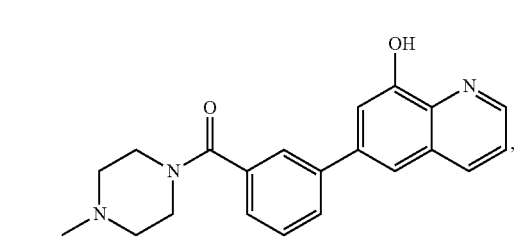

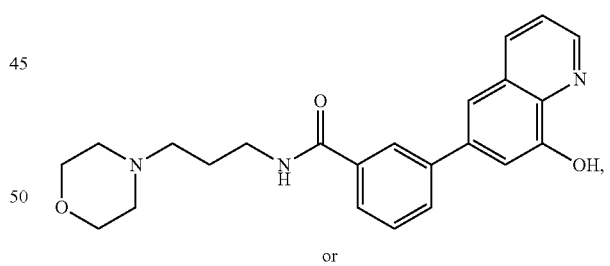

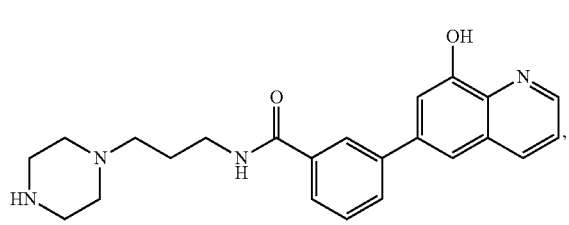

or

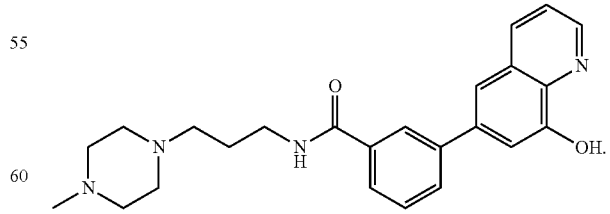

3. A method of treating herpesvirus infection of a host, the method comprising administering to the host an effective amount of a substance, wherein the substance is an inhibitor of a JMJD2 protein and is the compound of

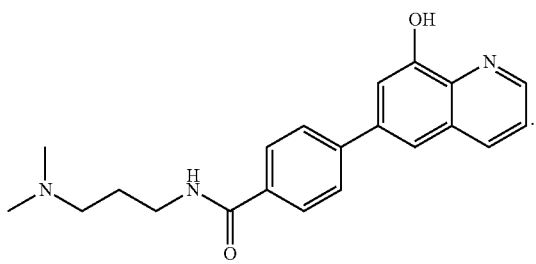 [SMILES: CN(C)CCCNC(=O)c1ccc(-c2cc(O)c3ncccc3c2)cc1]

4. A method of inhibiting a member of the JMJD2 family of histone demethylases in a herpesvirus-infected host, the method comprising administering to the host an effective amount of a substance, wherein the substance is the compound of

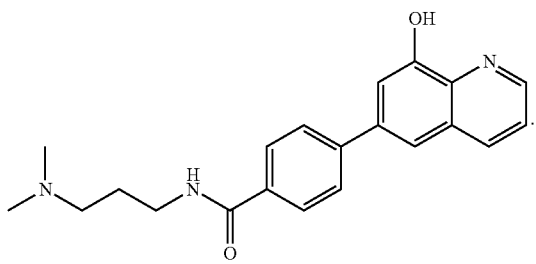 [SMILES: CN(C)CCCNC(=O)c1ccc(-c2cc(O)c3ncccc3c2)cc1]

5. The method of claim 1, wherein the compound is

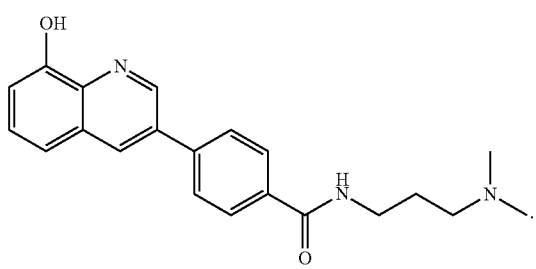 [SMILES: CN(C)CCCNC(=O)c1ccc(-c2cnc3c(O)cccc3c2)cc1]

6. The method of claim 1, wherein the compound is

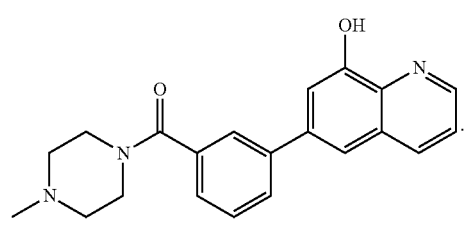 [SMILES: CN1CCN(C(=O)c2cccc(-c3cc(O)c4ncccc4c3)c2)CC1]

7. The method of claim 1, wherein the compound is

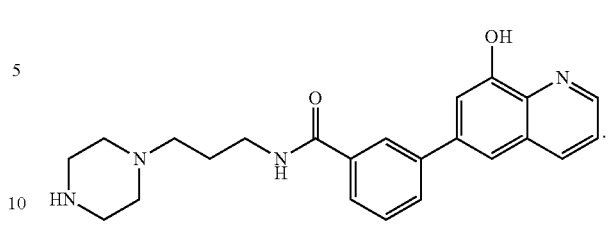

8. The method of claim 1, wherein the compound is

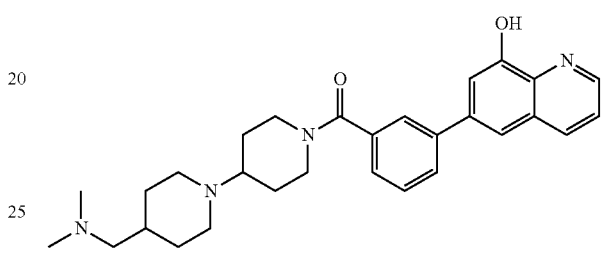

9. The method of claim 1, wherein the compound is

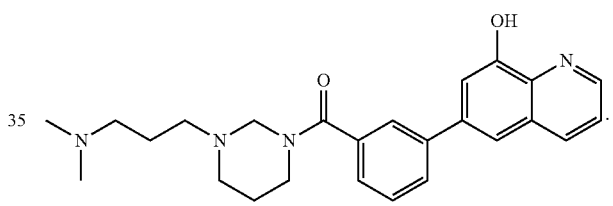

10. The method of claim 1, wherein the compound is

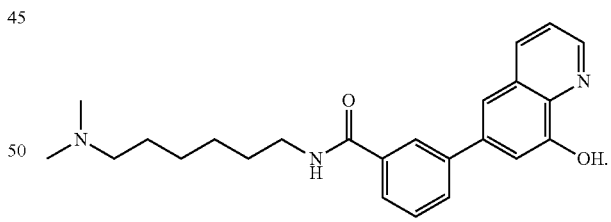

11. The method of claim 1, wherein the compound is

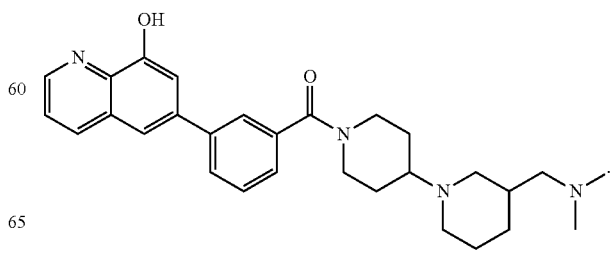

12. The method of claim 1, wherein the compound is

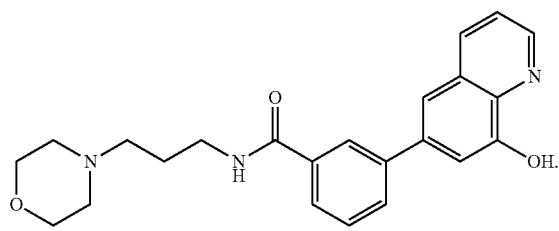 [SMILES: O=C(NCCCN1CCOCC1)c1cccc(-c2cc(O)c3ncccc3c2)c1]

13. The method of claim 1, wherein the compound is

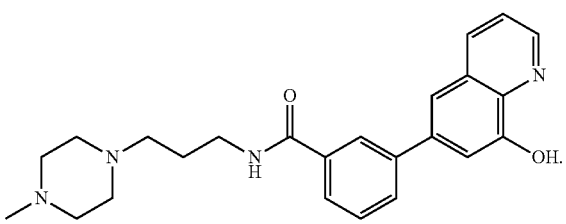 [SMILES: CN1CCN(CCCNC(=O)c2cccc(-c3cc(O)c4ncccc4c3)c2)CC1]

14. The method of claim 2, wherein the compound is

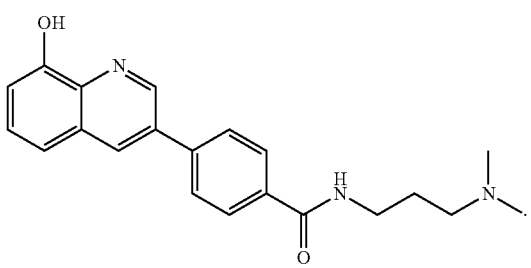

15. The method of claim 2, wherein the compound is

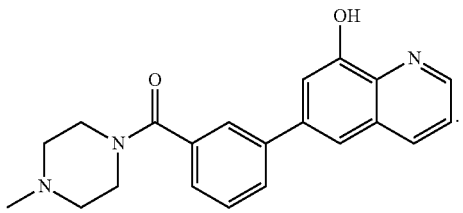 [SMILES: CN1CCN(C(=O)c2cccc(-c3cc(O)c4ncccc4c3)c2)CC1]

16. The method of claim 2, wherein the compound is

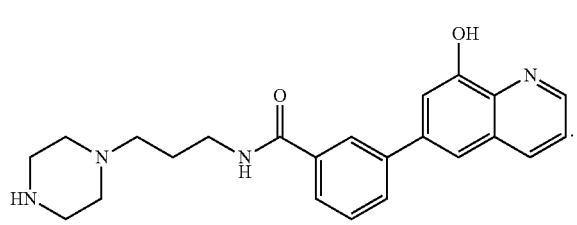 [SMILES: O=C(NCCCN1CCNCC1)c1cccc(-c2cc(O)c3ncccc3c2)c1]

17. The method of claim 2, wherein the compound is

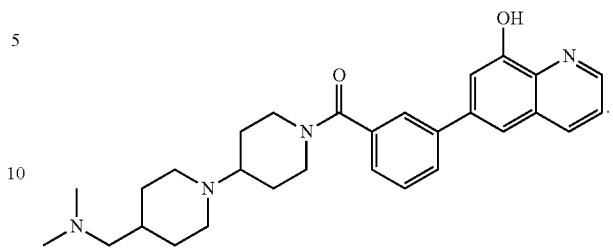

18. The method of claim 2, wherein the compound is

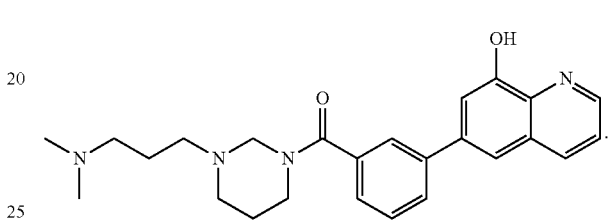

19. The method of claim 2, wherein the compound is

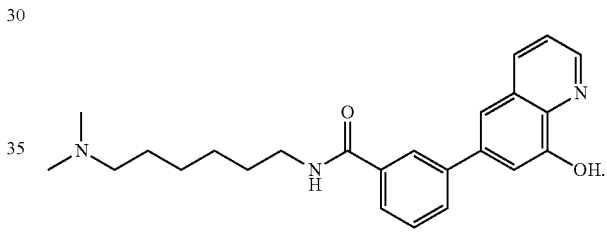

20. The method of claim 2, wherein the compound is

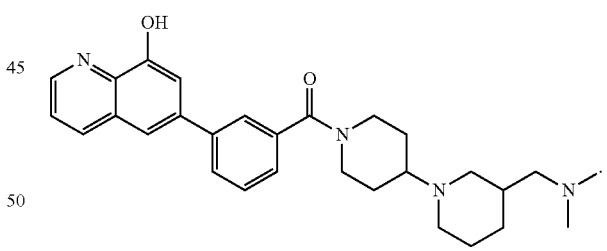

21. The method of claim 2, wherein the compound is

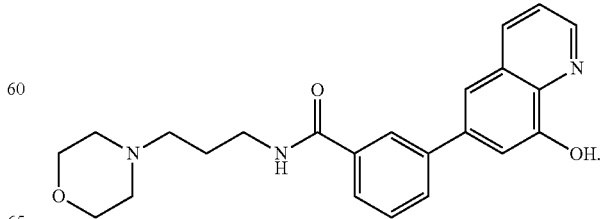

22. The method of claim 2, wherein the compound is

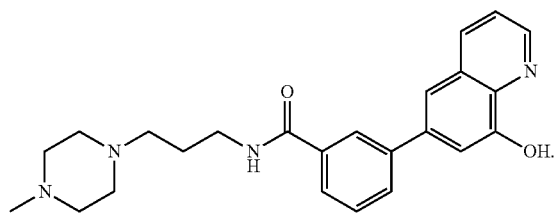

23. A method of treating herpesvirus infection of a host, the method comprising administering to the host an effective amount of a substance, wherein the substance is an inhibitor of a JMJD2 protein and is a pharmaceutically acceptable salt of a compound of

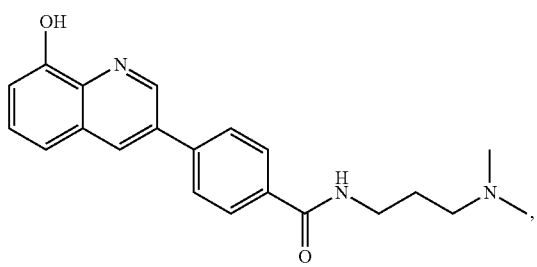

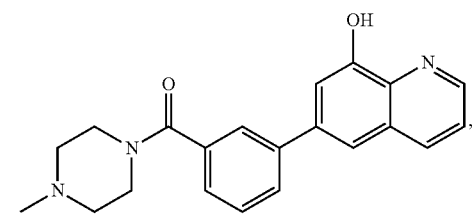

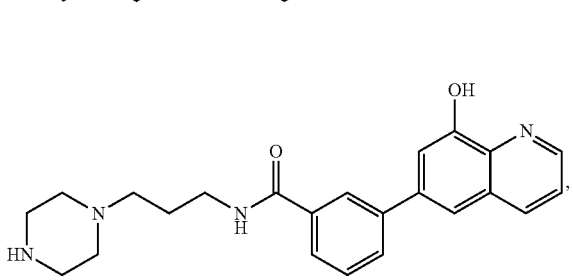

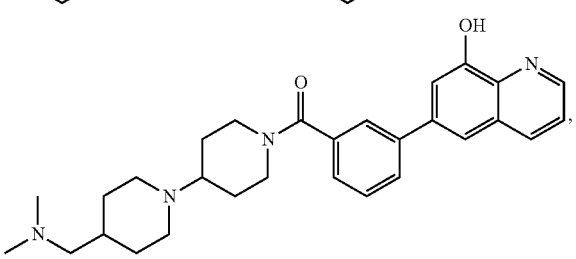

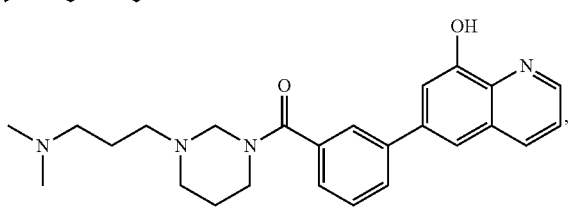

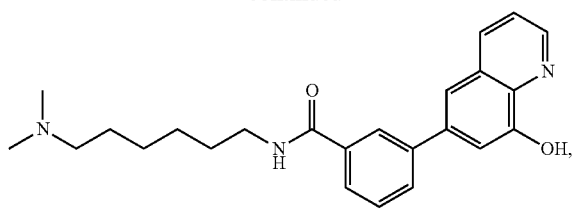 [SMILES: CN(C)CCCCCCNC(=O)c1cccc(-c2cc(O)c3ncccc3c2)c1]

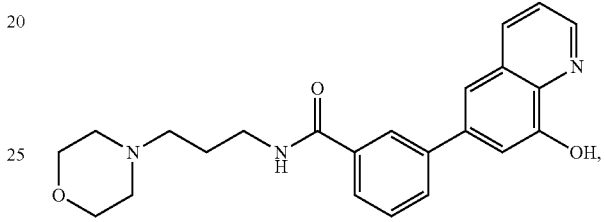

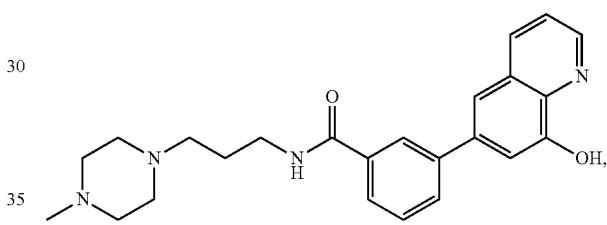

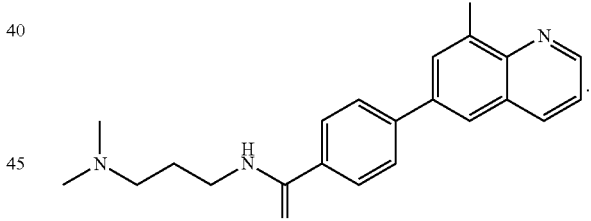

or

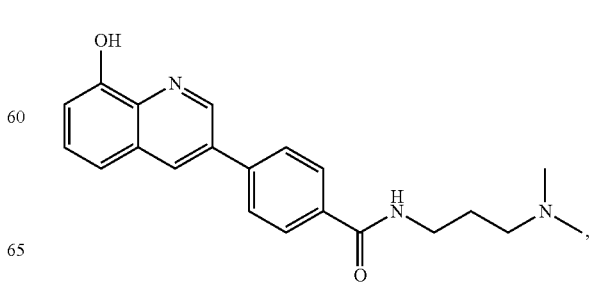

24. A method of inhibiting a member of the JMJD2 family of histone demethylases in a herpesvirus-infected host, the method comprising administering to the host an effective amount of a substance, wherein the substance is a pharmaceutically acceptable salt of a compound of

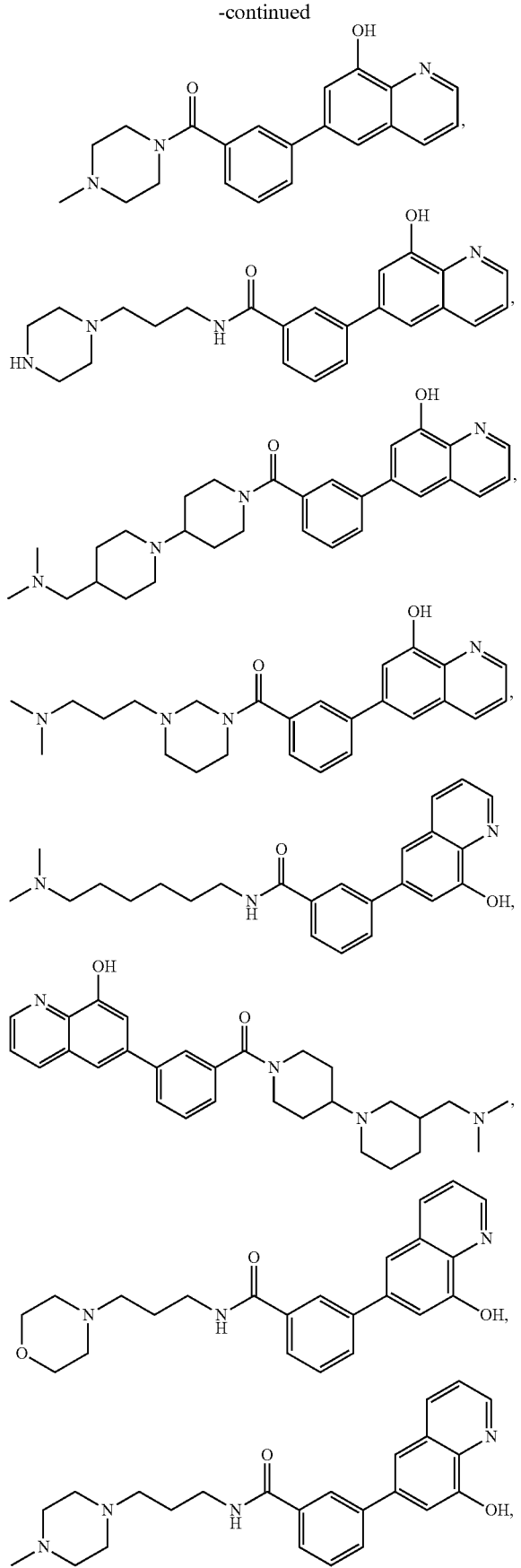
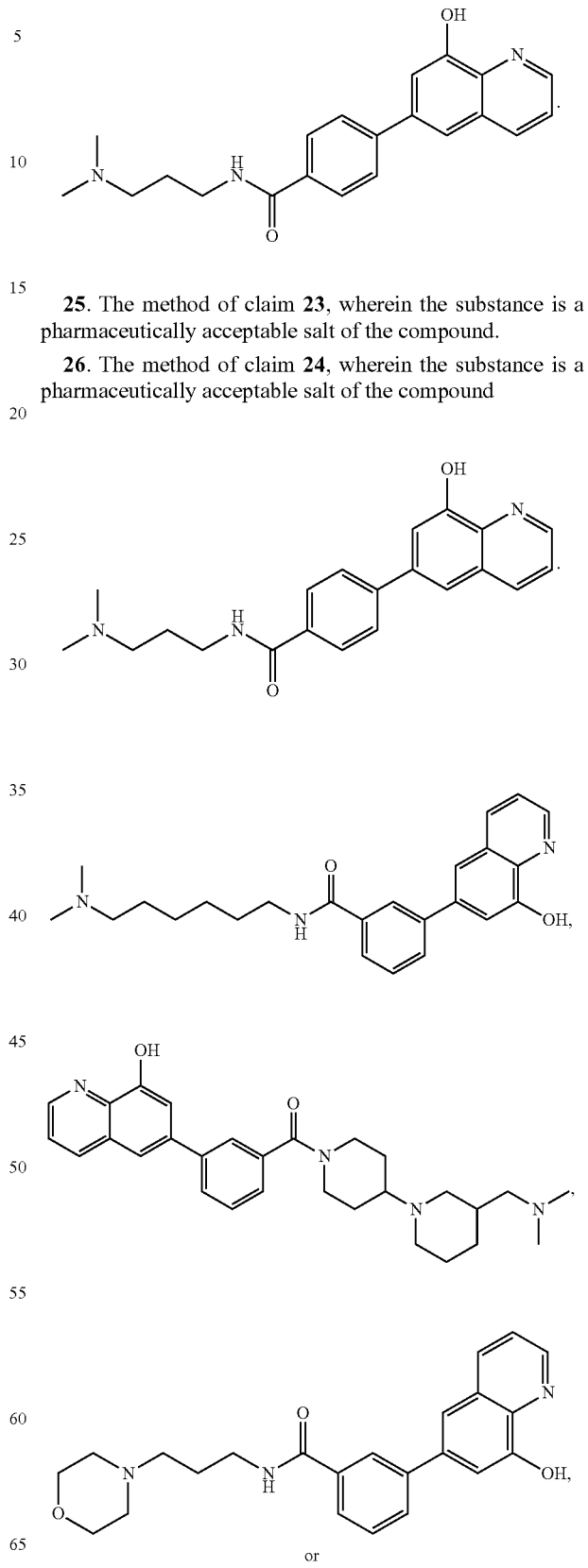
25. The method of claim 23, wherein the substance is a pharmaceutically acceptable salt of the compound.
26. The method of claim 24, wherein the substance is a pharmaceutically acceptable salt of the compound -continued
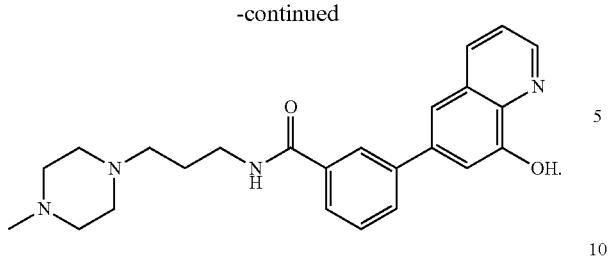
* * * * *

UNITED STATES PATENT AND TRADEMARK OFFICE
CERTIFICATE OF CORRECTION

| | | |
|---|---|---|
| PATENT NO. | : 8,871,789 B2 | Page 1 of 1 |
| APPLICATION NO. | : 13/747406 | |
| DATED | : October 28, 2014 | |
| INVENTOR(S) | : Kristie et al. | |

It is certified that error appears in the above-identified patent and that said Letters Patent is hereby corrected as shown below:

Title Page, Item (72), Under Inventors, please delete:

"David J. Maloney, Point of Rocks, MD (US); Ganesha Rai Bantukallu, Arlington, VA (US); Anton Simeonov, Bethesda, MD (US); Ajit Jadhav, Chantilly, VA (US)"

Title Page, Item (72), Under Inventors, please add:

--Jesse Arbuckle, Rockville, MD (US)--

Signed and Sealed this
Tenth Day of March, 2015

Michelle K. Lee
*Deputy Director of the United States Patent and Trademark Office*